(12) United States Patent
Kelly et al.

(10) Patent No.: US 7,432,281 B2
(45) Date of Patent: Oct. 7, 2008

(54) AMIDE DERIVATIVES AS ION-CHANNEL LIGANDS AND PHARMACEUTICAL COMPOSITIONS AND METHODS OF USING THE SAME

(75) Inventors: Michael G. Kelly, Thousand Oaks, CA (US); Satyanarayana Janagani, Santa Clara, CA (US); Ravindra B. Upasani, San Jose, CA (US)

(73) Assignee: Renovis, Inc., South San Franciso, CA (US)

( * ) Notice: Subject to any disclaimer, the term of this patent is extended or adjusted under 35 U.S.C. 154(b) by 449 days.

(21) Appl. No.: 10/961,483

(22) Filed: Oct. 7, 2004

(65) Prior Publication Data

US 2005/0222200 A1    Oct. 6, 2005

Related U.S. Application Data

(60) Provisional application No. 60/508,884, filed on Oct. 7, 2003.

(51) Int. Cl.
*A61K 31/44* (2006.01)
*A61K 31/47* (2006.01)
*C07D 213/02* (2006.01)
*C07D 217/02* (2006.01)

(52) U.S. Cl. .................. 514/310; 514/352; 546/143; 546/308; 544/256; 544/319

(58) Field of Classification Search ................ 546/310; 514/352
See application file for complete search history.

(56) References Cited

U.S. PATENT DOCUMENTS

| | | | |
|---|---|---|---|
| 3,346,584 A | 10/1967 | Manning et al. |
| 3,798,226 A | 3/1974 | Kanji et al. |
| 4,393,225 A | 7/1983 | Hayashi et al. |
| 4,430,423 A | 2/1984 | Aoki et al. |
| 4,579,866 A | 4/1986 | Stevenson et al. |
| 4,760,161 A | 7/1988 | Durette et al. |
| 5,559,141 A | 9/1996 | Karjalainen et al. |
| 5,693,672 A | 12/1997 | Weichert et al. |
| 6,034,107 A | 3/2000 | Hirai et al. |
| 6,083,987 A | 7/2000 | Nishino et al. |
| 6,221,865 B1 | 4/2001 | Sebti et al. |
| 6,262,104 B1 | 7/2001 | Dondio et al. |
| 6,331,640 B1 | 12/2001 | Fotouhi et al. |
| 6,414,145 B1 | 7/2002 | Boyle et al. |
| 6,486,156 B1 | 11/2002 | Arnould et al. |
| 6,656,971 B2 | 12/2003 | Wu et al. |
| 6,803,384 B2 | 10/2004 | Fotouhi et al. |
| 6,831,175 B2 | 12/2004 | Li et al. |
| 7,217,728 B2 | 5/2007 | Fotouhi et al. |
| 2002/0052512 A1 | 5/2002 | Fotouhi et al. |
| 2002/0165275 A1 | 11/2002 | Wu et al. |
| 2003/0199511 A1 | 10/2003 | Li et al. |
| 2003/0220495 A1 | 11/2003 | Boyle et al. |
| 2004/0006236 A1 | 1/2004 | Fotouhi et al. |
| 2004/0110802 A1 | 6/2004 | Thorarensen et al. |
| 2004/0116399 A1 | 6/2004 | Zhu et al. |
| 2004/0142953 A1 | 7/2004 | DeLorme et al. |
| 2004/0157919 A1 | 8/2004 | Wu et al. |
| 2004/0235888 A1 | 11/2004 | Yamamori et al. |
| 2005/0080119 A1 | 4/2005 | Fotouhi et al. |
| 2005/0165028 A1 | 7/2005 | Norman et al. |
| 2006/0020131 A1 | 1/2006 | Raeppel et al. |
| 2006/0111353 A1 | 5/2006 | Weichert et al. |
| 2006/0154988 A1 | 7/2006 | Andersen et al. |
| 2006/0194801 A1 | 8/2006 | Kelly et al. |
| 2007/0099956 A1 | 5/2007 | Kikuchi et al. |
| 2007/0105943 A1 | 5/2007 | Nakamoto et al. |

FOREIGN PATENT DOCUMENTS

| | | |
|---|---|---|
| EP | 0172083 | 2/1986 |
| JP | 11171848 | 6/1999 |
| JP | 2001139550 | 5/2001 |
| JP | 2002-055409 | 2/2002 |
| JP | 2005314347 | 11/2005 |
| WO | WO 96/32015 | 10/1996 |
| WO | WO 97/14681 | 4/1997 |
| WO | WO 97/29079 | 8/1997 |
| WO | WO 97/45402 | 12/1997 |
| WO | WO 97/48694 A1 | 12/1997 |
| WO | WO 98/50029 | 11/1998 |
| WO | WO 98/50030 | 11/1998 |
| WO | WO 98/50031 A1 | 11/1998 |

(Continued)

OTHER PUBLICATIONS

Baston et al., "Cyclohex-l-ene Carboxylic Acids: Synthesis and Biological Evaluation of Novel Inhibitors of Human 5α Reductase," Arch. Pharm. Pharm. Med. Chem., 1:31-38 (2003).

(Continued)

*Primary Examiner*—Zinna N Davis
(74) *Attorney, Agent, or Firm*—Jones Day

(57) ABSTRACT

Compounds are disclosed that have a formula represented by the following:

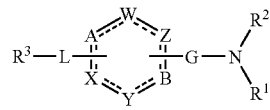

The compounds may be prepared as pharmaceutical compositions, and may be used for the prevention and treatment of a variety of conditions in mammals including humans, including by way of non-limiting example, pain, inflammation, traumatic injury, and others.

37 Claims, 4 Drawing Sheets

FOREIGN PATENT DOCUMENTS

| | | |
|---|---|---|
| WO | WO 99/02497 | 1/1999 |
| WO | WO 99/041235 | 8/1999 |
| WO | WO 99/48492 | 9/1999 |
| WO | WO 00/015213 | 3/2000 |
| WO | WO 00/54759 | 9/2000 |
| WO | WO 01/10380 A2 | 2/2001 |
| WO | WO 01/10381 A2 | 2/2001 |
| WO | WO 01/19798 | 3/2001 |
| WO | WO 01/21160 A2 | 3/2001 |
| WO | WO 01/21615 | 3/2001 |
| WO | WO 01/51456 A2 | 7/2001 |
| WO | WO 01/55115 | 8/2001 |
| WO | WO 01/64642 A2 | 9/2001 |
| WO | WO 01/82916 A2 | 11/2001 |
| WO | WO 02/44126 A2 | 6/2002 |
| WO | WO 02/51397 | 7/2002 |
| WO | WO 02/53101 | 7/2002 |
| WO | WO 02/59080 | 8/2002 |
| WO | WO 02/64547 | 8/2002 |
| WO | WO 02/64568 | 8/2002 |
| WO | WO 02/70494 | 9/2002 |
| WO | WO 02/94766 | 11/2002 |
| WO | WO 03/13516 | 2/2003 |
| WO | WO 03/15774 | 2/2003 |
| WO | WO 03/16254 | 2/2003 |
| WO | WO 03/18536 | 3/2003 |
| WO | WO 03/24448 | 3/2003 |
| WO | WO 03/40174 A2 | 5/2003 |
| WO | WO 03/51366 | 6/2003 |
| WO | WO 03/68749 | 8/2003 |
| WO | WO 2004/002481 | 1/2004 |
| WO | WO 2004/009549 | 1/2004 |
| WO | WO 2004/022536 | 3/2004 |
| WO | WO 2004/062601 | 7/2004 |
| WO | WO 2004/069792 A2 | 8/2004 |
| WO | WO 2004/069792 A3 | 8/2004 |
| WO | WO 2004/096784 | 11/2004 |
| WO | WO 2005/009962 | 2/2005 |
| WO | WO 2005/016277 | 2/2005 |
| WO | WO 2005/019176 | 3/2005 |
| WO | WO 2005/033079 | 4/2005 |
| WO | WO 2005/046683 | 5/2005 |
| WO | WO 2005/115977 | 12/2005 |

OTHER PUBLICATIONS

Dorsett et al., "Aminoalkenylbenzenesulfonamides with Hypotensive and Histamine-Releasing Properties," J. Med. Chem., 13(6):895-900 (1970).

Fu et al., "Peptidyl Aldehydes as Reversible Covalent Inhibitors of Protein Tyrosine Phosphatases," Biochemistry, 41:10700-10709 (2002).

Hutter et al., "QSAR of Human Steroid 5α-Reductase Inhibitors: Where are the Differences Between Isoenzyme Type 1 and 2?" QSAR Comb. Sci., 23:406-415 (2004).

Ikeda et al., "Cobalt-Catalyzed Heck-Type Reaction of Alkyl Halides with Styrenes," J. Am. Chem. Soc., 124:6514-6515 (2002).

Marchand et al., "Synthesis and Electrochemical Behaviour of New Polythiophenes Branched with Sulfonamides for Solid Phase Synthesis," New J. Chem., 23:869-875 (1999).

AMIDE DERIVATIVES AS ION-CHANNEL LIGANDS AND PHARMACEUTICAL COMPOSITIONS AND METHODS OF USING THE SAME

CROSS REFERENCE TO RELATED APPLICATIONS

The present application claims the priority of provisional applications U.S. Ser. No. 60/508,884, filed on Oct. 7, 2003, and the disclosure of this application is incorporated by reference herein its entirety. Applicants claim the benefits of this application under 35 U.S.C. §119(e).

FIELD OF THE INVENTION

This invention relates to novel compounds and to pharmaceutical compositions containing such compounds. This invention also relates to methods for preventing and/or treating pain and inflammation-related conditions in mammals, such as (but not limited to) arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders, using the compounds and pharmaceutical compositions of the invention.

BACKGROUND OF THE INVENTION

Studies of signaling pathways in the body have revealed the existence of ion channels and sought to explain their role. Ion channels are integral membrane proteins with two distinctive characteristics: they are gated (open and closed) by specific signals such as membrane voltage or the direct binding of chemical ligands and, once open, they conduct ions across the cell membrane at very high rates.

There are many types of ion channels. Based on their selectivity to ions, they can be divided into calcium channel, potassium channel, sodium channel, etc. The calcium channel is more permeable to calcium ions than other types of ions, the potassium channel selects potassium ions over other ions, and so forth. Ion channels may also be classified according to their gating mechanisms. In a voltage-gated ion channel, the opening probability depends on the membrane voltage, whereas in a ligand-gated ion channel, the opening probability is regulated by the binding of small molecules (the ligands). Since ligand-gated ion channels receive signals from the ligand, they may also be considered as "receptors" for ligands.

Examples of ligand-gated ion channels include nAChR (nicotinic acetylcholine receptor) channel, GluR (glutamate receptor) channel, ATP-sensitive potassium channel, G-protein activated channel, cyclic-nucleotide-gated channel, etc.

Transient receptor potential (TRP) channel proteins constitute a large and diverse family of proteins that are expressed in many tissues and cell types. This family of channels mediates responses to nerve growth factors, pheromones, olfaction, tone of blood vessels and metabolic stress et al., and the channels are found in a variety of organisms, tissues and cell types including nonexcitable, smooth muscle and neuronal cells. Furthermore, TRP-related channel proteins are implicated in several diseases, such as several tumors and neurodegenerative disorders and the like. See, for example, Minke, et al., *APStracts* 9:0006P (2002).

Nociceptors are specialized primary afferent neurons and the first cells in a series of neurons that lead to the sensation of pain. The receptors in these cells can be activated by different noxious chemical or physical stimuli. The essential functions of nociceptors include the transduction of noxious stimuli into depolarizations that trigger action potentials, conduction of action potentials from primary sensory sites to synapses in the central nervous system, and conversion of action potentials into neurotransmitter release at presynaptic terminals, all of which depend on ion channels.

One TRP channel protein of particular interest is the vanilloid receptor. Also known as VR1, the vanilloid receptor is a non-selective cation channel which is activated or sensitized by a series of different stimuli including capsaicin, heat and acid stimulation and products of lipid bilayer metabolism (anandamide), and lipoxygenase metabolites. See, for example Smith, et al., *Nature,* 418:186-190 (2002). VR1 does not discriminate among monovalent cations, however, it exhibits a notable preference for divalent cations with a permeability sequence of $Ca^{2+}>Mg^{2+}>Na^+=K+=Cs^+$. $Ca^{2+}$ is especially important to VR1 function, as extracellular $Ca^{2+}$ mediates desensitization, a process which enables a neuron to adapt to specific stimuli by diminishing its overall response to a particular chemical or physical signal. VR1 is highly expressed in primary sensory neurons in rats, mice and humans, and innervates many visceral organs including the dermis, bones, bladder, gastrointestinal tract and lungs. It is also expressed in other neuronal and non-neuronal tissues including the CNS, nuclei, kidney, stomach and T-cells. The VR1 channel is a member of the superfamily of ion channels with six membrane-spanning domains, with highest homology to the TRP family of ion channels.

VR1 gene knockout mice have been shown to have reduced sensory sensitivity to thermal and acid stimuli. See, for example, Caterina, et al. *Science,* 14:306-313 (2000). This supports the concept that VR1 contributes not only to generation of pain responses but also to the maintenance of basal activity of sensory nerves. VR1 agonists and antagonists have use as analgesics for the treatment of pain of various genesis or etiology, for example acute, inflammatory and neuropathic pain, dental pain and headache (such as migraine, cluster headache and tension headache). They are also useful as anti-inflammatory agents for the treatment of arthritis, Parkinson's Disease, Alzheimer's Disease, stroke, uveitis, asthma, myocardial infarction, the treatment and prophylaxis of pain syndromes (acute and chronic [neuropathic]), traumatic brain injury, spinal cord injury, neurodegenerative disorders, alopecia (hair loss), inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

Compounds, such as those of the present invention, which interact with the vanilloid receptor can thus play a role in treating or preventing or ameliorating these conditions.

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (Tetrahedron, 53, 1997, 4791) and olvanil or —N-(4-hydroxy-3-methoxybenzyl)oleamide (J. Med. Chem., 36, 1993, 2595).

International Patent Application, Publication Number WO 02/08221 discloses diaryl piperazine and related compounds which bind with high selectivity and high affinity to vanilloid receptors, especially Type I Vanilloid receptors, also known as capsaicin or VR1 receptors. The compounds are said to be useful in the treatment of chronic and acute pain conditions, itch and urinary incontinence.

International Patent Application, Publication Numbers WO 02/16317, WO 02/16318 and WO 02/16319 suggest that compounds having a high affinity for the vanilloid receptor are useful for treating stomach-duodenal ulcers.

U.S. Pat. No. 3,424,760 and U.S. Pat. No. 3,424,761 both describe a series of 3-Ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively. International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fluorophenyl)-N-isoquinolin-5-yl-5-methyl-1H-pyrazole-3-carboxamide, 1-(2-chloro-5-trifluoromethylphenyl)-N-isoquinolin-5-yl-5-methyl-IN-pyrazole-3-carboxamide, 5-methyl-N-(3-methylisoquinolin-5-yl)-1-[3-(trifluoromethyl)phenyl]-1N-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino)ethyl]-1,2-dihydro-4-methyl-2-oxo-7-quinolinyl]-4-phenyl-1-piperazinecarboxamide.

We have now discovered that certain compounds have surprising potency and selectivity as VR-1 antagonists. The compounds of the present invention are considered to be particularly beneficial as VR-1 antagonists as certain compounds exhibit improved aqueous solubility and metabolic stability.

SUMMARY OF THE INVENTION

It has now been found that compounds such as those set forth herein, are capable of modifying mammalian ion channels such as the VR1 cation channel. This finding leads to novel compounds having therapeutic value. It also leads to pharmaceutical compositions having the compounds of the present invention as active ingredients and to their use to treat, prevent or ameliorate a range of conditions in mammals such as but not limited to pain of various genesis or etiology, for example acute, chronic, inflammatory and neuropathic pain, dental pain and headache (such as migraine, cluster headache and tension headache).

Accordingly, in a first aspect of the invention, compounds are disclosed that are capable of modifying ion channels, in vivo, having a formula I:

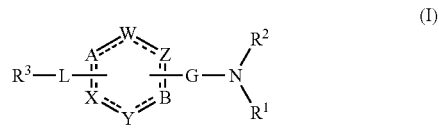

wherein:

A is N, $CR^4$, a carbon atom bound to L, or is not an atom;

one of W, Z, B, Y and X is a carbon atom bound to L if A is not an atom, another of W, Z, B, Y and X is a carbon atom bound to G, and each of the remaining W, Z, B, Y and X is independently N or $CR^4$;

L is substituted or unsubstituted —(C—C)—, —($CR^5$=$CR^6$)— or —(C≡C)—;

G is C=O, C=S or $SO_2$;

$R^1$ is substituted or unsubstituted aliphatic, alkyl, heteroalkyl, aryl, heteroaryl, aralkyl, or heteroaralkyl;

$R^2$ is hydrogen or substituted or unsubstituted alkyl;

$R^3$ is substituted or unsubstituted aliphatic, alkyl, heteroalkyl, aryl, heteroaryl, aralkyl, or heteroaralkyl; and each $R^4$ is independently hydrogen, alkyl, substituted or unsubstituted alkyl, acyl, acylamino, alkylamino, alkylthio, alkoxy, alkoxycarbonyl, alkylarylamino, arylalkyloxy, amino, aryl, arylalkyl, sulfoxide, sulfone, sulfanyl, aminosulfonyl, arylsulfonyl, sulfuric acid, sulfuric acid ester, dihydroxyphosphoryl, aminohydroxyphosphoryl, azido, carboxy, carbamoyl, carboxyl, cyano, cycloheteroalkyl, dialkylamino, halo, heteroaryloxy, heteroaryl, heteroalkyl, hydroxyl, nitro or thio; and each of $R^5$ and $R^6$ is independently H, halo, or substituted or unsubstituted aliphatic, alkyl, heteroalkyl, aryl, heteroaryl, aralkyl, or heteroaralkyl;

or a pharmaceutically acceptable salt, solvate or prodrug thereof;

and isomers and stereoisomers thereof.

In a further embodiment of the invention, compounds are capable of modifying ion channels, in vivo, having a formula IA:

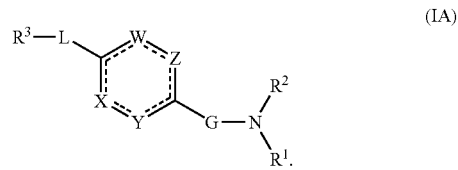

In a particular embodiment of the compounds of formula IA, L is substituted or unsubstituted —(C—C)—, —($CR^5$=$CR^6$)—or —(C≡C)—, G is C=O, $R^1$ is substituted or unsubstituted aliphatic, alkyl, heteroalkyl, aryl, heteroaryl, aralkyl, or heteroaralkyl, $R^2$ is hydrogen, and $R^3$ is substituted or unsubstituted aliphatic or alkyl.

In another particular embodiment of compounds of formula IA, hereinafter referred to as compounds of formula IA', $R^3$-L represents the moiety: $CR^3R^6$=$CR^5$

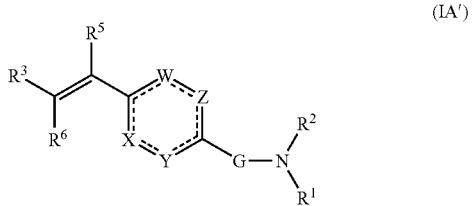

(IA')

wherein R³ is as defined for compounds of formula I and R⁵ and R⁶ are independently selected from hydrogen, halo, substituted or unsubstituted aliphatic, alkyl, heteroalkyl, aryl, heteroaryl, aralkyl and heteroaralkyl.

In certain specific compounds R³ is selected from substituted or unsubstituted C1-6 alkyl, substituted or unsubstituted C1-6 cycloalkyl, substituted or unsubstituted aryl and substituted or unsubstituted aralkyl; and each R⁵ and R⁶ are independently selected from hydrogen, halo and substituted and unsubstituted C1-6alkyl; and 0-3 groups selected from W, Z, X and Y represent NR⁴.

In compounds of formula IA', R⁵ and R⁶ may, for example, independently represent hydrogen, halo or substituted or unsubstituted C1-6 alkyl. Preferably R⁵ and R⁶ represent hydrogen.

In another particular embodiment of compounds of formula IA hereinafter referred to as compounds of formula IA", R³—L represents the moiety R³C≡C—.

In compounds of formula I, IA, IA' and IA", preferably G represents CO. Alternatively G may represent SO₂.

In compounds of formula I, IA, IA' and IA", W, Z, X and Y may for example each represent CR⁴ especially CH. Alternatively X may represent N and W, Z and Y may each represent CR⁴. In another example set of compounds each of X, Y and Z represents CR⁴ especially CH. In another example set of compounds W is N.

Generally in compounds of formula I and IA L is preferably —(C=C)— or —C≡C—. Thus in one example set of compounds L represents —(C=C)—. In another example set of compounds L represents —C≡C—.

In compounds of formula I, IA, IA' and IA", R1 may for example represent substituted or unsubstituted aryl e.g. substituted phenyl. Example of substituents include alkyl, alkyl (OH), —COOH, C(Me)₃, CH(Me)₂, halo, CF₃, cyano and methoxy. Alternatively it may represent substituted or unsubstituted pyridyl.

In compounds of formula I, IA, IA' and IA", R² preferably represents hydrogen.

In compounds of formula I, IA, IA' and IA", R³ may for example represent CR⁶'R⁷R⁸ wherein R⁶' represents hydrogen, halo or substituted or unsubstituted C1-6alkyl; each of R⁷ and R⁸ is independently halo or substituted or unsubstituted C1-6 alkyl; or R⁷ and R⁸ together form a substituted or unsubstituted C3-8 cycloalkyl ring. For example R⁷ may represent lower alkyl (eg methyl). For example R⁸ may represent lower alkyl (e.g. methyl). In particular examples, R⁶' may represent hydrogen and R⁷ and R⁸ may represent methyl. Alternatively each of R⁶', R⁷ and R⁸ may represent methyl. Alternatively each of R⁶', R⁷ and R⁸ may represent fluoro. Alternatively R⁶' may represent hydrogen and R⁷ and R⁸ together form a cyclohexyl ring.

In further embodiment of the compounds of formula I, IA, IA' and IA", R³ may for example represent substituted or unsubstituted aryl or heteroaryl.

In a first alternative embodiment of the compounds of formula IA, R³ is CF₃, n-propyl, or a group of the formula

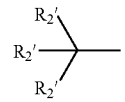

wherein R²' is hydrogen or alkyl; and wherein two R²' may join together to form a cycloalkyl or cycloheteroalkyl ring of 3-8 atoms; provided at least two of R²' are alkyl.

With respect to the compounds of formula IA, R¹ may be substituted phenyl, or alternatively, substituted or unsubstituted naphthyl. Further, R¹ may also be substituted or unsubstituted heteroaryl, and in a particular embodiment, the heteroaryl may be selected from the group consisting of pyrimidinyl, thiazolyl, and pyrazolyl. More particularly, the heteroaryl may be 2-pyridyl, 3-pyridyl or 4-pyridyl. In a particular embodiment, the substitution on the heteroaryl is selected from the group consisting of hydrogen, alkyl, trifluoromethyl, halo, methoxy, trifluoromethoxy, amino and carboxy. In a yet further particular embodiment, the substitution on heteroaryl is selected from the group consisting of tert-butyl, cyano, trifluoroalkyl, halo, nitro, methoxy, amino and carboxy.

In a still further aspect of the invention derived from the compounds of formula IA, and in a second alternative embodiment thereof, additional compounds are disclosed that are capable of modifying ion channels, in vivo, having a formula II:

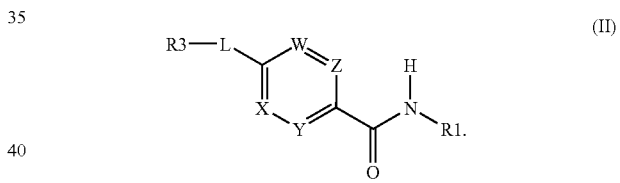

(II)

wherein L, W, X, Y, Z, R¹ are as defined with respect to formula IA, and R³ is as defined with respect to the first alternative embodiment of formula IA. In a particular embodiment of this second alternative embodiment, R¹ may be substituted alkyl or —(CR²₂)x-R⁴'. If R¹ is —(CR²₂)x-R⁴', R² is hydrogen or alkyl; R⁴' is R⁴ and R⁴ is as described with respect to formula 1, and n is an integer of from 1-3. In this same embodiment, R⁴' may be selected from t-butyl, aryl, cycloalkyl, cycloheteroalkyl and heteroaryl; and alternately, R⁴' may be selected from substituted or unsubstituted phenyl, or naphthalenyl; further alternately, R⁴' may be selected from the group consisting of cyclopropyl, cyclopentyl, or cyclohexyl; yet further, R⁴' may be selected from substituted or unsubstituted pyrrolidinyl, piperidinyl, or morpholinyl; still further, R⁴' may be selected from substituted or unsubstituted pyridinyl or pyrimidinyl; and in addition, R⁴' may be selected from substituted or unsubstituted furanyl, imidazolyl, thiophenyl, pyrazolyl, or thiazolyl. R⁴' may also be selected from substituted or unsubstituted benzodioxanyl, benzopyranyl, indolyl, indazolyl, methylenedioxyphenyl, quinolinyl, isoquinolinyl, tetrahydroquinolinyl, tetrahydroisoquinolinyl, dihydroquinolinyl, or dihydroisoquinolinyl. In a particular embodiment, R⁴' is t-Bu. With respect to all of the foregoing variants within this embodiment, x is 1 or 2.

In a further embodiment in accordance with the compound of formula 2 wherein $R^1$ is substituted alkyl, $R^1$ may be t-Bu, or may be substituted or unsubstituted cycloalkyl, cycloheteroalkyl or heteroaryl, and may particularly be substituted or unsubstituted cyclopropyl, or cyclopentyl. $R^1$ may also be substituted or unsubstituted pyrrolidinyl, piperidinyl, or morpholinyl, or may also be substituted or unsubstituted pyridinyl or pyrimidinyl, or further, may be substituted or unsubstituted furanyl, imidazolyl, thiophenyl, pyraxolyl, or thiazolyl. In a further embodiment, $R^1$ may also be substituted or unsubstituted benzodioxanyl, benzopyranyl, indolyl, indazolyl, methylenedioxyphenyl, quinolinyl, isoquinolinyl, tetrahydroquinolinyl, tetrahydroisoquinolinyl, dihydroquinolinyl, or dihydroisoquinolinyl. In a still further embodiment, $R^1$ may be substituted or unsubstituted aryl, and particularly, may be substituted or unsubstituted phenyl, naphthalenyl, 2-biphenyl, or 4-biphenyl.

In a still further aspect of the invention derived from the compounds of formula II, additional compounds are disclosed that are capable of modifying ion channels, in vivo, having a formula III, as follows:

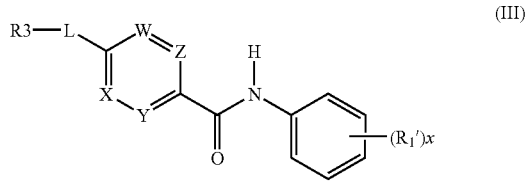

(III)

wherein $R^{1'}$ is $R^4$; and x is selected from 1-5. In this embodiment, x may be 1; $R^{1'}$ may be selected from the group consisting of methyl, isopropyl, t-butyl, cyano, trifluoroalkyl, halo, nitro, methoxy, trifluoromethoxy, amino, alkylamino, dialkylamino, phenyl, $SO_2Me$, $SO_2CF_3$, $SO_2NMe_2$, and carboxy; the $R^{1'}$ substitution may be at the 4-position.

In a further aspect of the invention and with reference to the compounds of formulas II and III, W, X, Y and Z may be $CR^4$, and one or more thereof may be N. Particularly, W and Y may each be N with the remainder being $CR^4$, and any two of the four positions may be N, also with the remainder of the positions being $CR^4$. In this particularly described embodiment, L may be —($CR^5$=$CR^6$)—, with $R^5$ and $R^6$ both being hydrogen, and with each alternatively being methyl with the other being hydrogen. Further, L can be —(C≡C)—, and $R^3$ can be t-Bu, I—Pr or $CF_3$.

In a further embodiment of the invention, other compounds are capable of modifying ion channels, in vivo, herein after referred to as compounds of formula IB, in which B is a carbon atom joined to $GNR^1R^2$; W is a carbon atom joined to $LR^3$; and A, X, Y, Z are as defined for compounds of formula I and preferably each represent $CR^4$ especially CH; G is as defined for compounds of formula I and is preferably CO; and $R^3$, L, $R^1$ and $R^2$ are each as defined for compounds of formula I and are preferably as defined for compounds of formula IA, IA' and IA".

In yet further particular embodiments, the compounds of the invention are set forth and may be selected from a comprehensive listing of such compounds, set forth later on herein in Table 1. The Table contains in excess of 440 compounds that have been synthesized and have as a group, demonstrated activity in their capacity of modifying ion channels, in vivo, and thereby functioning in the therapeutic applications set forth herein in relation to capsaicin and the vanilloid receptor.

The compounds of the present invention are useful for the treatment of inflammatory pain and associated hyperalgesia and allodynia. They are also useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, Alzheimer's Disease, stroke, uveitis, asthma, myocardial infarction, traumatic brain injury, spinal cord injury, neurodegenerative disorders, alopecia (hair loss), inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides compounds which are capable of modifying ion channels, in vivo. Representative ion channels so modified include voltage-gated channels and ligand-gated channels, including cation channels such as vanilloid channels.

In a further aspect, the present invention provides pharmaceutical compositions comprising a compound of the invention, and a pharmaceutical carrier, excipient or diluent. In this aspect of the invention, the pharmaceutical composition can comprise one or more of the compounds described herein.

In a further aspect of the invention, a method is disclosed for treating mammals, including humans, as well as lower mammalian species, susceptible to or afflicted with a condition from among those listed herein, and particularly, such condition as may be associated with e.g. arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description, in conjunction with the following illustrative drawings.

DETAILED DESCRIPTION OF THE INVENTION

Definitions

Figure 1:
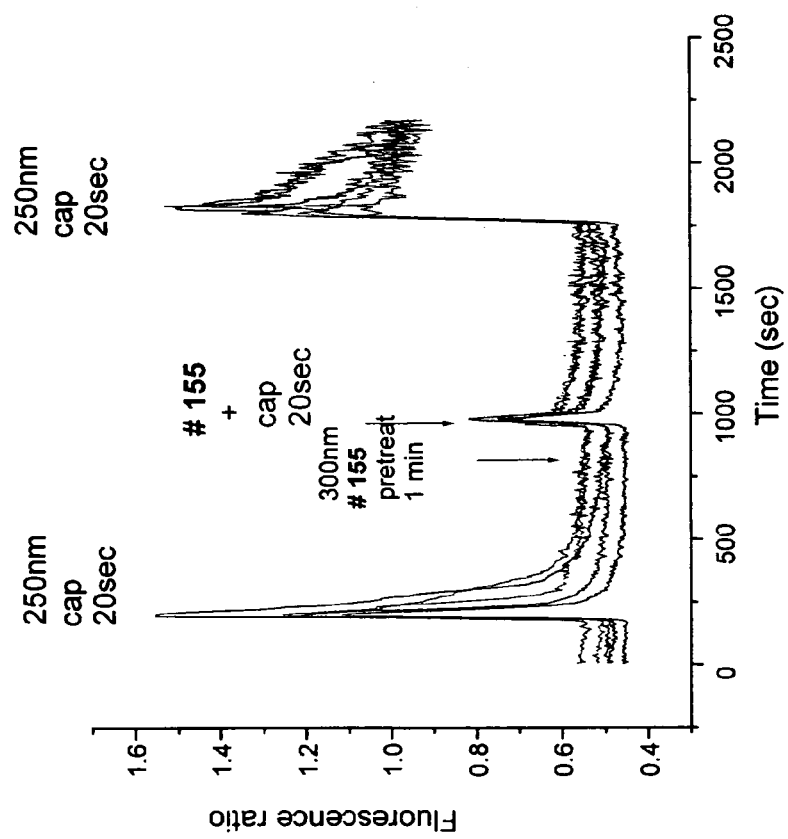
FIG. 1: A graph demonstrating the activity of compound 155 in inhibiting a capsaicin induced intracellular calcium current. Calcium ion flux is reflected by fluorescence.

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, C$_{2-6}$ alkenyl, C$_{3-6}$ alkynyl, C$_{1-6}$ alkoxy, aryl and di-C$_{1-6}$ alkylamino.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R where R is hydrogen, alkyl, aryl or cycloalkyl.

"Substituted alkenyl" includes those groups recited in the definition of "substituted" herein, and particularly refers to an alkenyl group having I or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having I or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NRC(O)OR' where R is hydrogen, alkyl, aryl or cycloalkyl, and R' is alkyl or cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=$CH_2$), n-propenyl (—$CH_2$CH=$CH_2$), isopropenyl (—C($CH_3$)=$CH_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=$CHCH_2$— and —C($CH_3$)=CH— and —CH=C($CH_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—$CH_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R—C(O)—, where R is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR'R", wherein each of R' and R" are independently selected from hydrogen and alkyl.

"Arylamino" refers to the group aryl-NR'R", wherein each of R' and R" are independently selected from hydrogen, aryl and heteroaryl.

"Alkoxyamino" refers to a radical —N(H)OR where R represents an alkyl or cycloalkyl group as defined herein.

"Alkoxycarbonyl" refers to a radical —C(O)-alkoxy where alkoxy is as defined herein.

"Alkylarylamino" refers to a radical —NRR' where R represents an alkyl or cycloalkyl group and R' is an aryl as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to, methylthio, ethylthio, propylthio, butylthio, and the like.

"Amino" refers to the radical —$NH_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Aminocarbonyl" refers to the group —C(O)NRR where each R is independently hydrogen, alkyl, aryl and cycloalkyl, or where the R groups are joined to form an alkylene group.

"Aminocarbonylamino" refers to the group —NRC(O) NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NHR where R represents an aryl group as defined herein.

"Aryloxycarbonyl" refers to a radical —C(O)—O-aryl where aryl is as defined herein.

"Arylsulfonyl" refers to a radical —S(O)$_2$R where R is an aryl or heteroaryl group as defined herein.

"Azido" refers to the radical —N$_3$.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having I or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having I or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{14}$, —O—, =O, —OR$^4$, —SR$^{14}$, —S, S, —NR$^{14}$R$^{15}$, =NR$^{14}$, —CX$_3$, —CF$_3$, —CN, —OCN, —SCN, —NO, —NO$_2$, =N$_2$, —N$_3$, —S(O)$_2$—O—, —S(O)$_2$OH, —S(O)$_2$R$^{14}$, —OS(O$_2$)O$^-$, —OS(O)$_2$R$^{14}$, —P(O)(O—)$_2$, —P(O)(OR$^{14}$)(O—), —OP(O)(OR$^{14}$)(OR$^{15}$), —C(O)R$^{14}$, —C(S)R$^4$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(R$^{16}$)NR$^{14}$R$^{15}$ and —C(NR$^{16}$)NR$^{14}$R$^{15}$ where each X is independently a halogen; each R$^{14}$, R$^{15}$, R$^{16}$ and R$^{17}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{18}$R$^{19}$, —C(O)R$^{18}$ or —S(O)$^y$R$^{18}$ or optionally R$^{18}$ and R$^{19}$ together with the atom to which they are both attached form a cycloheteroalkyl or substituted cycloheteroalkyl ring; and R$^{18}$ and R$^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

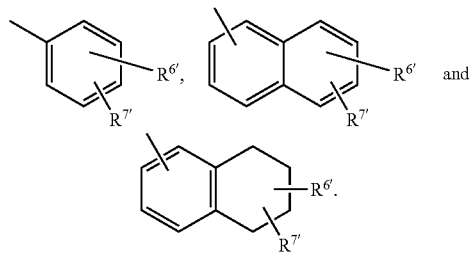

In these formulae one of R$^{6'}$ and R$^{7'}$ may be hydrogen and at least one of R$^{6'}$ and R$^{7'}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{10}$COR$^{11}$, NR$^{10}$SOR$^{11}$, NR$^{10}$SO$_2$R$^{14}$, COOalkyl, COOaryl, CONR$^{10}$R$^{11}$, CONR$^{10}$OR$^{10}$, NR$^{10}$R$^{11}$, SO$_2$NR$^{10}$R$^{11}$, S-alkyl, S-alkyl, SOalkyl, SO$_2$alkyl, Saryl, SOaryl, SO$_2$aryl; or R$^{6'}$ and R$^{7'}$ may be joined to form a cyclic ring (saturated or unsaturated) from 5 to 8 atoms, optionally containing one or more heteroatoms selected from the group N, O or S. R$^{10}$, R$^{11}$, and R$^{12}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

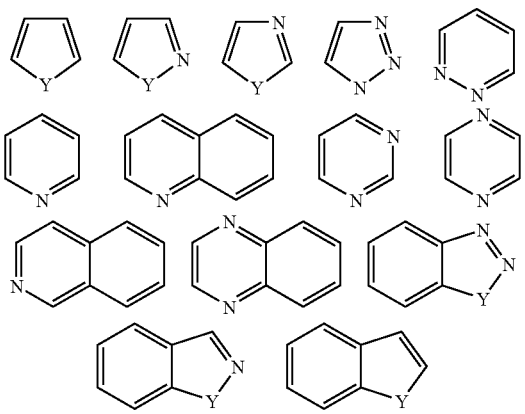

wherein each Y is selected from carbonyl, N, $NR^4$, O, and S.

Examples of representative cycloheteroalkyls include the following

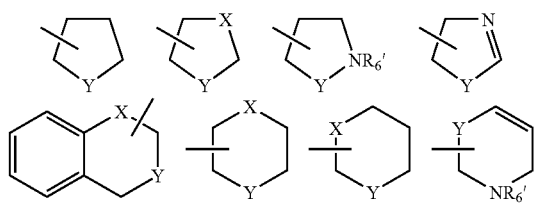

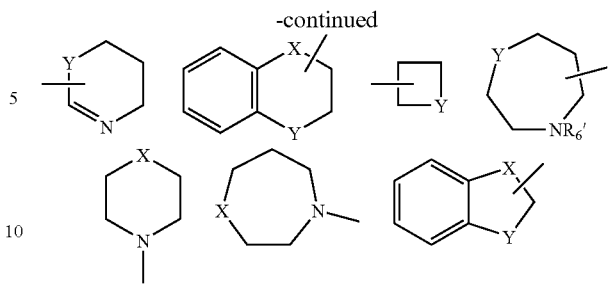

wherein each X is selected from $CR^4_2$, $NR^4$, O and S; and each Y is selected from $NR^4$, O and S, and where $R^{6'}$ is $R^2$.

Examples of representative cycloheteroalkenyls include the following:

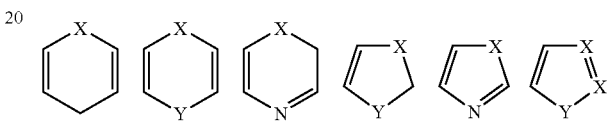

wherein each X is selected from $CR^4$, $NR^4$, O and S; and each Y is selected from carbonyl, N, $NR^4$, O and S.

Examples of representative aryl having hetero atoms containing substitution include the following:

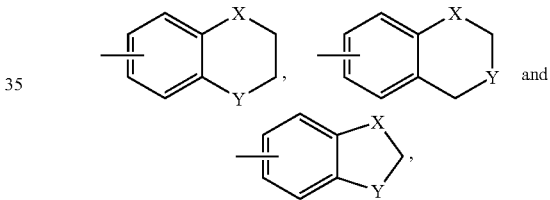

wherein each X is selected from C—$R^4$, $CR^4_2$, $NR^4$, O and S; and each Y is selected from carbonyl, $NR^4$, O and S.

"Hetero substituent" refers to a halo, O, S or N atom-containing functionality that may be present as an $R^4$ in a $R^4C$ group present as substituents directly on A, B, W, X, Y or Z of the compounds of this invention or may be present as a substituent in the "substituted" aryl and aliphatic groups present in the compounds.

Examples of hetero substituents include:
-halo,
—$NO_2$, —$NH_2$, —NHR, —$N(R)_2$,
—NRCOR, —NRSOR, —$NRSO_2R$, OH, CN, $CO_2R$,
—$CO_2H$,
—R—OH, —O—R, —COOR,
—$CON(R)_2$, —CONROR,
—$SO_2H$, —R—S, —$SO_2N(R)_2$,
—S(O)R, —$S(O)_2R$, wherein each R is independently an aryl or aliphatic, optionally with substitution. Among hetero substituents containing R groups, preference is given to those materials having aryl and alkyl R groups as defined herein. Preferred hetero substituents are those listed above.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

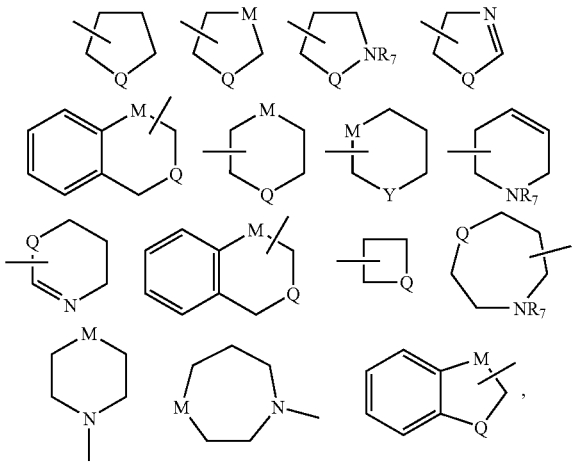

optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. In the examples, M is $CR^7$, $NR^2$, O, or S; Q is O, $NR^2$ or S. $R^7$ and $R^8$ are independently selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR where R is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R—(O$_2$)S— wherein R is any substituent described herein. "Aminosulfonyl" or "Sulfonamide" refers to the radical H$_2$N(O$_2$)S—, and "substituted aminosulfonyl" "substituted sulfonamide" refers to a radical such as R$_2$N(O$_2$)S— wherein each R is independently any substituent described herein.

"Sulfone" refers to the group —SO$_2$R. In particular embodiments, R is selected from H, lower alkyl, alkyl, aryl and heteroaryl.

"Thioaryloxy" refers to the group —SR where R is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (I) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

As set forth earlier herein, the compounds of the present invention are useful for preventing and/or treating a broad range of conditions, among them, arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders or conditions in mammals.

In order that the invention described herein may be more fully understood, the following structures representing compounds typical of the invention are set forth. It should be understood that these examples are for illustrative purposes only and are not to be construed as limiting this invention in any manner.

Accordingly, additional groups of particular compounds are provided. Thus, and as discussed earlier herein, suitable compounds capable of modifying ion channels in vivo, may be selected from those listed in Table 1, below, and may be prepared either as shown or in the form of a pharmaceutically acceptable salt, solvate or prodrug thereof; and isomers and stereoisomers thereof. All such variants are contemplated herein and are within the scope of the present invention.

In certain aspects, the present invention provides prodrugs and derivatives of the compounds according to the formulae above. Prodrugs are derivatives of the compounds of the invention, which have cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the amide compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including by way of non limiting example, oral, rectal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1

Tablets

A compound of formula I is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2

Capsules

A compound of formula I is admixed as a dry powder with a starch diluent in an approximate 1:1 weight ratio. The mixture is filled into 250 mg capsules (125 mg of active compound per capsule).

Formulation 3

Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4

Tablets

The compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

The compound of formula I is dissolved or suspended in a buffered sterile saline injectable aqueous medium to a concentration of approximately 5 mg/ml.

Formulation 6

Topical

Stearyl alcohol (250 g) and a white petrolatum (250 g) are melted at about 75° C. and then a mixture of a compound of formula I (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals. Accordingly, the compounds and pharmaceutical compositions of this invention find use as therapeutics for preventing and/or treating neurodegenerative, autoimmune and inflammatory conditions in mammals including humans.

In a method of treatment aspect, this invention provides a method of treating a mammal susceptible to or afflicted with a condition associated with arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds or their derivatives of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active derivatives.

General Synthetic Procedures

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The target compounds are synthesized by known reactions outlined in the following schemes. The products are isolated and purified by known standard procedures. Such procedures include (but are not limited to) recrystallization, column chromatography or HPLC. The target compounds, for example, may be prepared by the reaction of an appropriately substituted halopyridine with an appropriately functionalized carboxy boronic acid to obtain the desired biaryl carboxylic acid. The carboxylic acid intermediate thus obtained can be conveniently converted to its corresponding amide by activation followed by reacting with an appropriately substituted amine. The products are isolated and purified by known standard procedures. Such procedures include (but are not limited to) recrystallization, column chromatography or HPLC.

Preparation of Substituted Benzoic Acids

Intermediate 1

4-((E)-3,3-Dimethyl-but-1-enyl)-benzoic acid

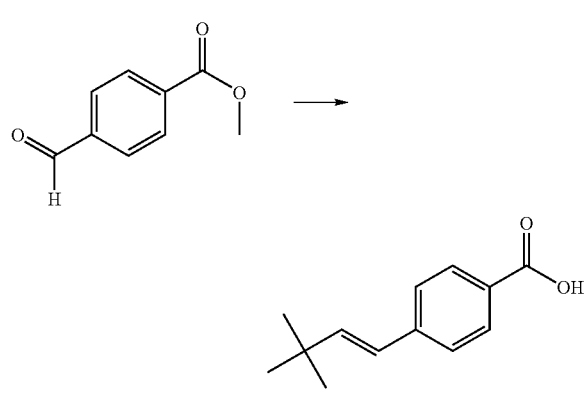

To a cooled (0° C.) and well stirred suspension of 4-carboxy benzaldehyde (2.0 g, 13.32 mmol) in anhydrous THF (90 mL) is added 33.3 mmol of neopentyl magnesium chloride in hexane during 20 minutes and the mixture is stirred at the same temperature for an additional two hours before being quenched with satyrated ammonium chloride solution. Most of the THF is evaporated and the aqueous mixture is treated with conc. HCl (50 mL) and the mixture is heated to reflux for 2 hours. The mixture is then cooled to ambient temperature and extracted with methylene chloride (2×100 mL), the organic layer is dried over sodium sulfate and concentrated to obtain the desired 4-(3,3-dimethyl-but-1-enyl)-benzoic acid.

Intermediate 2

((E)-4-Pent-1-enyl)-benzoic acid

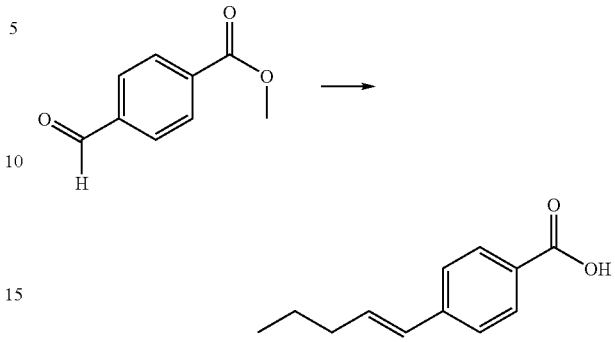

To a stirred solution of 4-formyl-benzoic acid (1.5 g, 10 mmol) in THF at −78° C., was added 2.5 eq. of n-butyllithium in hexan and the mixture was slowly warmed to ambient temperature. After stirring for an additional 2 hrs, the reaction was quenched with sat. $NH_4Cl$ solution and extracted with EtOAc (2×100 mL). The combined organic extracts were dried ($Na_2SO_4$) and concentrated to give the crude carbinol which was treated with 30% $H_2SO_4$ for 30 min at ambient temperature. The reaction mixture was then quenched with cold water and the precipitate formed was filtered, washed with water and vacuum dried to obtain the title compound (1.1 g, 57.9%).

Intermediate 3

6-(3,3-Dimethylbut-1-ynyl)nicotinic acid

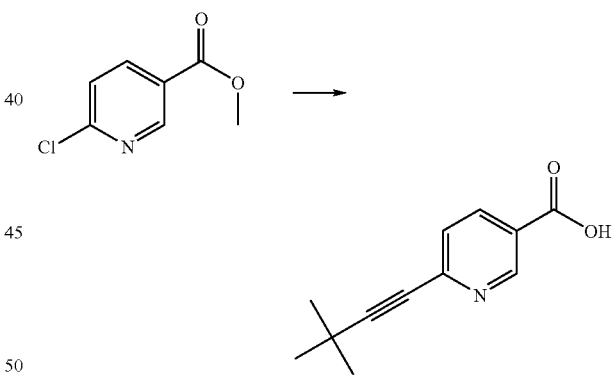

6-Chloronicotinic acid methyl ester (500 mg; 2.93 mmol) was suspended in 1,4-dioxane (3 ml) in a 5 ml reaction vial. To the vessel was added dichlorobis(triphenylphosphine)palladium(II) (70 mg; 3 mol %), copper iodide (12 mg), N,N-diisopropylethylamine (0.63 ml; 3.5 mmol) and 3,3-dimethylbut-1-yne (0.44 ml; 3.5 mmol). The vessel was sealed and the mixture was heated at 80° C. for 24 hrs. The solvents were evaporated to dryness and 20 ml of tetrahydrofuran and 20 ml of 10N NaOH was added. The mixture was stirred at room temperature for 30 minutes and the solvent was evaporated. The basic layer was acidified with concentrated HCl and extracted three times with EtOAc. The organic layers were washed with brine and dried over $Na_2SO_4$, filtered and evaporated to give the desired product as a brown powder (590 mg; 99%).

MS: MH+=204

Intermediate 4

4-(3,3-Dimethylbut-1-ynyl)benzoic acid

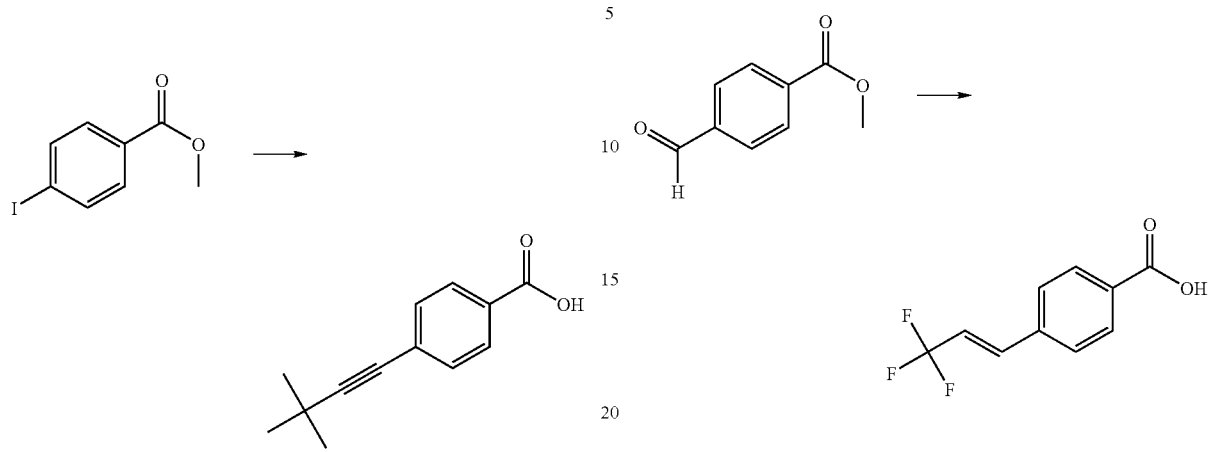

The 4-iodobenzoic acid methyl ester (500 mg; 1.9 mmol) was suspended in 1,4-dioxane (3 ml) in a 5 ml reaction vial. To the vessel was added dichlorobis(triphenylphosphine)palladium(II) (44 mg; 3 mol %), copper iodide (7.5 mg), N,N-diisopropylethylamine (0.39 ml; 3.5 mmol) and 3,3-dimethylbut-1-yne (0.275 ml; 3.5 mmol). The vessel was sealed and the mixture was heated at 80° C. for 24 hrs. The solvents were evaporated to dryness and 20 ml of tetrahydrofuran and 20 ml of 10N NaOH was added. The mixture was stirred at room temperature for 30 minutes and the solvent was evaporated. The basic layer was acidified with concentrated HCl and extracted three times with EtOAc. The organic layers were washed with brine and dried over $Na_2SO_4$, filtered and evaporated to give the desired product as a brown powder (210 mg; 28%).

MS: MH+=203

Intermediate 5

2,2,2-Trifluoroethyldiphenylphosphine Oxide

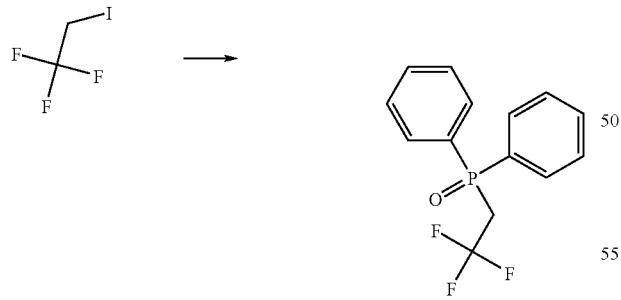

A mixture of ethyl diphenylphosphonite (1.98 g; 5.8 mmol) and 2,2,2-trifluoroethyl iodide (6.1 g; 29 mmol) was stirred at room temperature under nitrogen for 24 hrs. The excess reagents were removed under vacuum. The residue was purified on silica gel using a 0-100% hexane-ethyl acetate gradient to give the target as a white powder (800 mg; 49%).

MS: MH+=286

4-(3,3,3-Trifluoropropenyl)benzoic acid

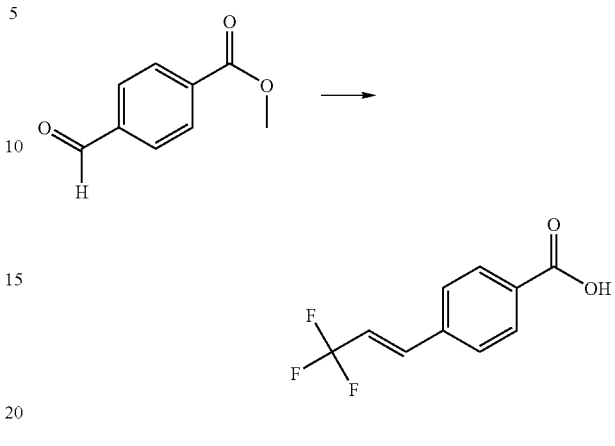

4A Molecular sieves (7 g; activated powder) was suspended in 8.8 ml of 1.0M TBAF in THF and stirred overnight at room temperature under nitrogen. To the solution was added methyl 4-formylbenzoate (160 mg; 0.97 mmol) and 2,2,2-trifluoroethyldiphenylphosphine oxide (415 mg; 1.46 mmol) in 10 ml of anhydrous THF. After stirring overnight, the solvents were evaporated to dryness. The residue was dissolved in EtOAc and washed with water and brine. The organic dried over $Na_2SO_4$, filtered and evaporated. The residue was dissolved in 10 ml of THF and 10 ml of 1N NaOH and refluxed for 30 minutes. The mixture was acidified with concentrated HCl and extracted three times with EtOAc. The organic layers were washed with brine and dried over $Na_2SO_4$, filtered and evaporated to give the desired product as a brown powder (125 mg; 60%).

MS: MH+=217

In addition to the benzoic acids listed above other benzoic acids, which were employed or can be employed to prepare amide compounds of this invention, were synthesized following the procedures described above for Intermediate 1-6 and the appropriate reagents, starting materials and purification methods known to those skilled in the art. (David, please revise as appropriate)

Amidation of Carboxylic Acids

EXAMPLE 1

A Representative Synthesis of Benzamide

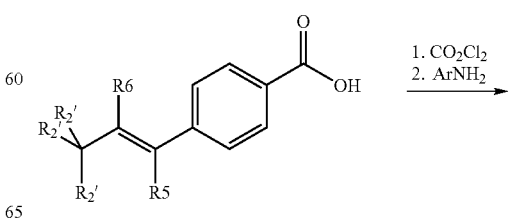

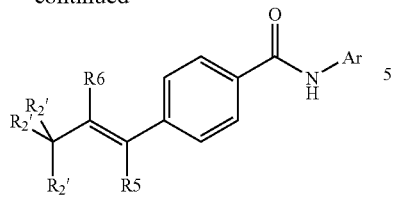

4-((E)-3,3-Dimethyl-but-1-enyl)-N-(3-methoxy-phenyl)-benzamide

To a cooled (0° C.) and well stirred suspension of 4-(3,3-dimethyl-but-1-enyl)-benzoic acid (1.5 g, 7.34 mMol) in a mixture of EtOAc and DMF (1:1, 25 mL) is added oxalyl chloride (0.364 g, 4.04 mMol) slowly drop-wise and the mixture is agitated for one hour. m-Anisidine (1.36 g, 11.01 mMol) is then added in EtOAc (5 mL) and the mixture is stirred for 6.0 hours before being quenched with saturated potassium carbonate solution. The precipitate is filtered, washed with water and vacuum dried to obtain the title compound.

EXAMPLE 3

A Representative Synthesis of Benzamides Using Automated Parallel Synthesis Method The appropriate benzoic acid (2 mmol) was dissolved or suspended in 15 ml of chloroform and treated with 20 mmol of thionyl chloride. The reaction mixture was refluxed for fifteen minutes and the solvents were removed under vacuum. The residue was dissolved in 4 ml of anhydrous chloroform and 60 µl (30 µmole) of this solution was added to each well of the 96 well glass plates. Appropriate amine was then added to the corresponding well (60 µmole), followed by N,N-diisopropylethylamine (120 µmole). The plate was then heated at 65° C. for 15 minutes. The solvents were removed using an HT-12 Genevac centrifugal evacuator and 100 µl of DMSO was added to each well and the compounds were transferred to a 96-well polypropylene reaction plate. The plates were then sealed using an ABgene plate sealer and submitted to LC-MS purification.

General Method for Automated Parallel LC-MS Purification of Libraries

The libraries were purified using a Perkin Elmer API100 mass spectrometer coupled to Shimadzu LC pumps. The chromatographic method employed was 10-100% gradient of acetonitrile to water over 8 minutes at a flow rate of 6 ml per minute. The column used was a 10×50 mm YMC C18 and the compounds were collected using a Gilson 204 fraction collector.

Following the procedure described above for Example 1 or 2 and the appropriate reagents, starting materials and purification methods known to those skilled in the art, the amide compounds of this invention were prepared.

The following synthetic and biological examples are offered to illustrate this invention and are not to be construed in any way as limiting the scope of this invention. In the examples below, all temperatures are in degrees Celsius (unless otherwise indicated). The compounds that have been prepared in accordance with the invention, are presented in tabular form below. The syntheses of these representative compounds were carried out in accordance with the methods set forth above.

Exemplary Compounds of the Invention

The following compounds have been prepared according to the methods of the invention and are set forth in Table 1, below. For purposes of this Table, the biological activity of each compound is expressed as noted in the following legend, which should be consulted in the review of the Table:

"+" compound exhibited 0-25% inhibition of calcium ion influx induced by capsaicin stimulation.

"++" compound exhibited 25-50% inhibition of calcium ion influx induced by capsaicin stimulation.

"+++" compound exhibited 50-75% inhibition of calcium ion influx induced by capsaicin stimulation.

"++++" compound exhibited 75% or greater inhibition of calcium ion influx induced by capsaicin stimulation.

Compounds with a percent inhibition represented by "++++" are of particular interest.

TABLE 1

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 1 | 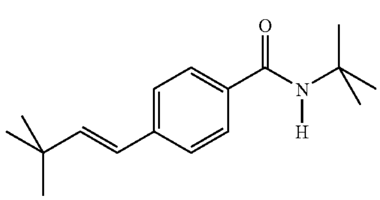 | 259.39 | 260.22 | 3.99 | 3.89 | 4.88 | |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 2 | 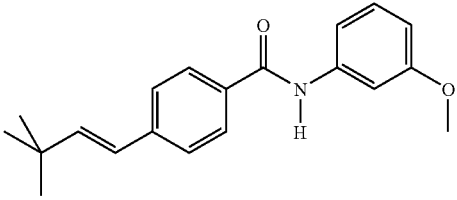 | 309.41 | 310.41 | 4.08 | 3.94 | 4.48 | ++++ |
| 3 | 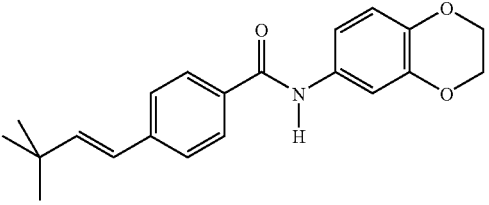 | 337.42 | 338.29 | 3.96 | 3.85 | 4.39 | ++++ |
| 4 | 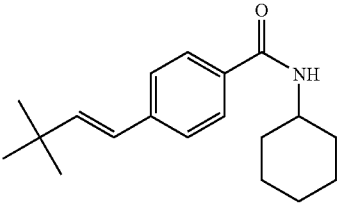 | 285.43 | 286.25 | 4.11 | 3.94 | 4.44 | |
| 5 | 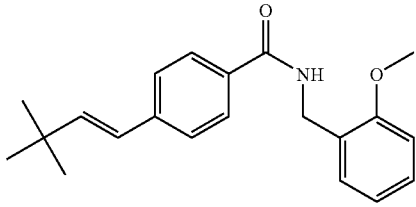 | 323.44 | 324.37 | 4.01 | 3.86 | 4.58 | ++ |
| 6 | 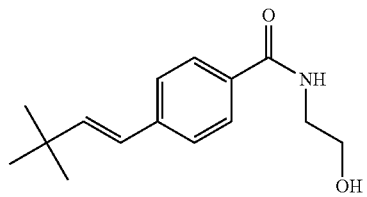 | 247.34 | 248.19 | 3.00 | 2.79 | 3.36 | + |
| 7 | 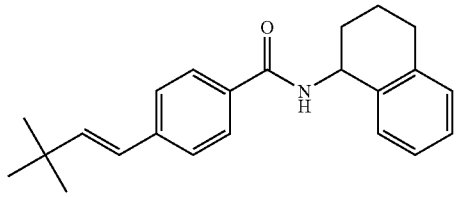 | 333.48 | 334.38 | 4.29 | 4.16 | 4.58 | ++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 8 | 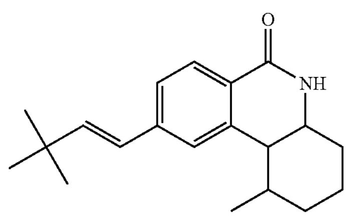 | 313.49 | 314.24 | 4.36 | 4.24 | 4.84 | +++ |
| 9 | 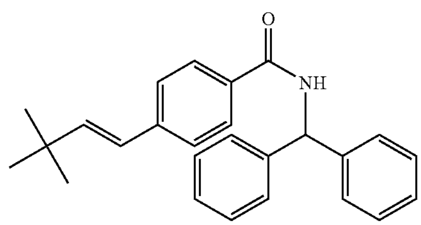 | 369.51 | 370.20 | 4.36 | 4.24 | 4.69 | + |
| 10 | 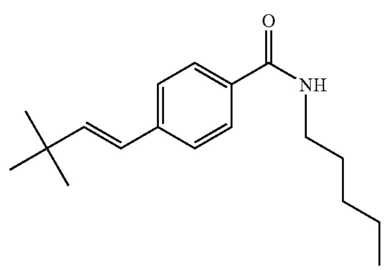 | 273.42 | 274.26 | 4.11 | 3.98 | 4.55 | |
| 11 | 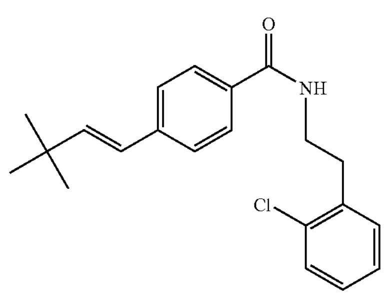 | 341.88 | 342.21 | 4.19 | 3.99 | 4.65 | ++++ |
| 12 | 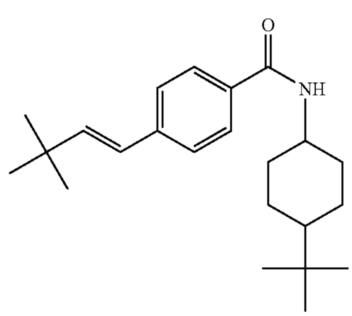 | 341.54 | 342.29 | 4.81 | 4.36 | 5.14 | + |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 13 | 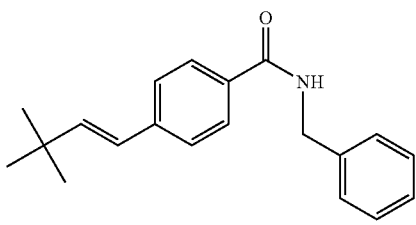 | 293.41 | 294.23 | 3.93 | 3.85 | 4.41 | + |
| 14 | 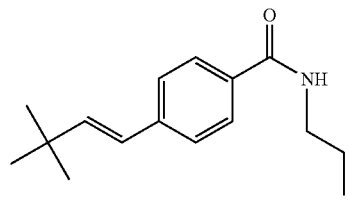 | 245.37 | 246.25 | 3.69 | 3.58 | 4.05 | + |
| 15 | 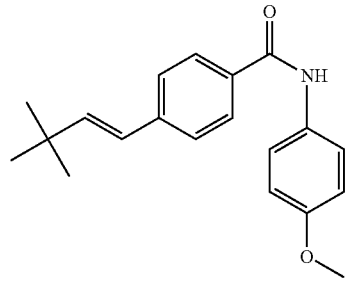 | 309.41 | 310.39 | 3.99 | 3.89 | 4.29 | + |
| 16 | 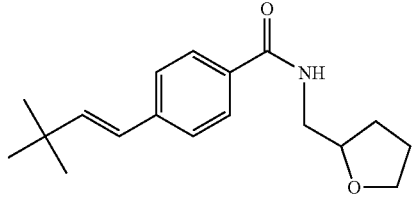 | 287.41 | 288.07 | 3.51 | 3.42 | 3.96 | + |
| 17 | 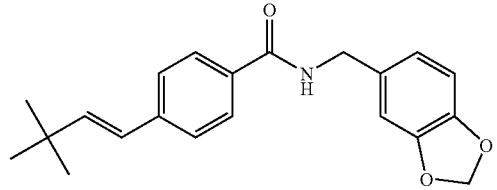 | 337.42 | 338.29 | 3.85 | 3.75 | 4.24 | + |
| 18 | 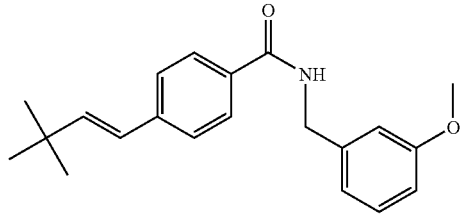 | 323.44 | 324.38 | 3.92 | 3.83 | 4.26 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 19 | 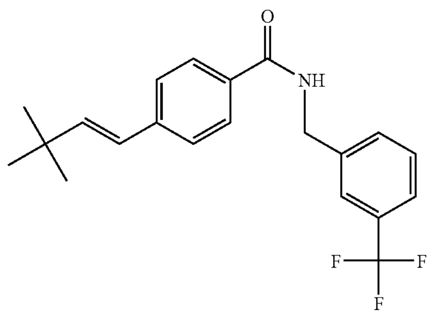 | 361.41 | 362.35 | 4.29 | 4.14 | 4.66 | |
| 20 | 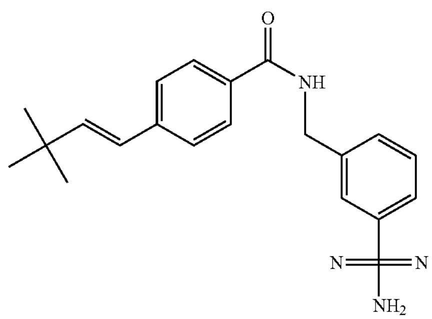 | 386.52 | 387.24 | 3.41 | 3.32 | 3.69 | + |
| 21 | 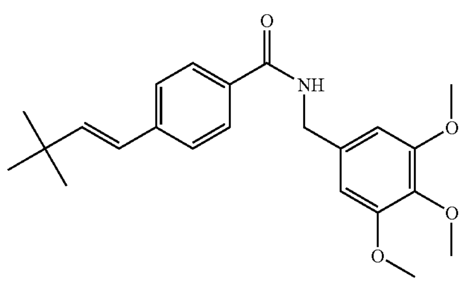 | 383.49 | 384.23 | 3.82 | 3.75 | 4.25 | |
| 22 | 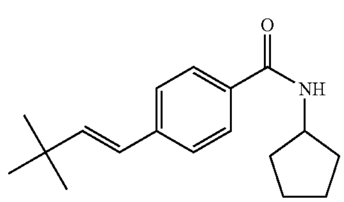 | 271.41 | 272.27 | 3.92 | 3.78 | 4.28 | |
| 23 | 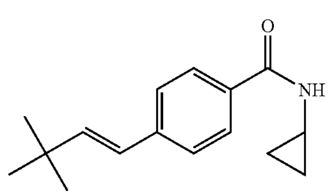 | 243.35 | 244.26 | 3.51 | 3.42 | 3.86 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 24 | 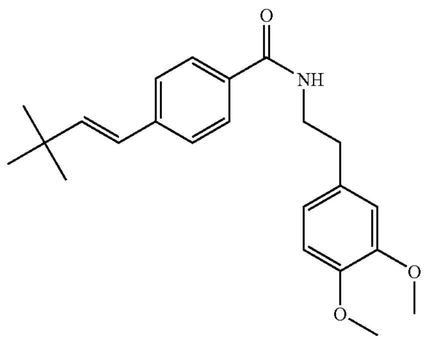 | 367.49 | 368.25 | 3.78 | 3.61 | 4.19 | + |
| 25 | 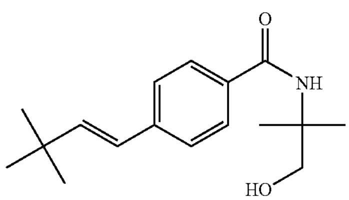 | 275.39 | 276.27 | 3.45 | 3.35 | 3.81 | |
| 26 | 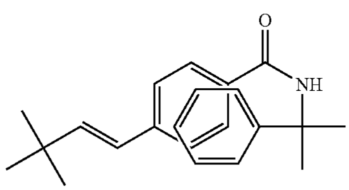 | 321.47 | 322.35 | 4.19 | 4.04 | 4.58 | + |
| 27 | 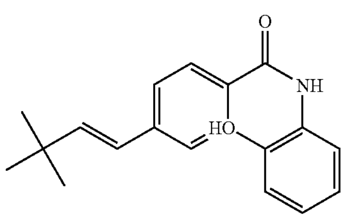 | 295.38 | 296.29 | 3.93 | 3.79 | 4.36 | |
| 28 | 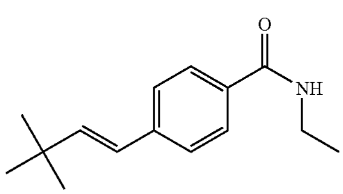 | 231.34 | 232.25 | 3.51 | 3.38 | 4.12 | |
| 29 | 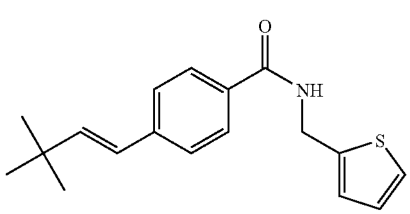 | 299.44 | 300.24 | 3.89 | 3.71 | 4.17 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 30 | 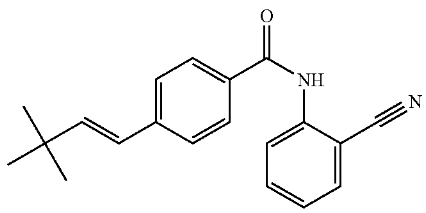 | 304.40 | 305.35 | 3.89 | 3.81 | 4.29 | ++ |
| 31 | 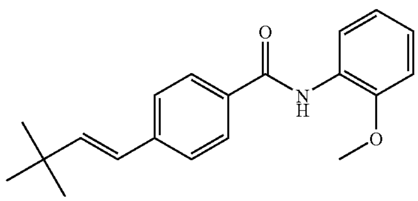 | 309.41 | 310.41 | 4.32 | 4.19 | 4.69 | + |
| 32 | 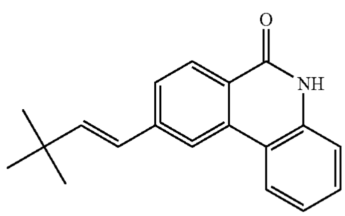 | 321.47 | 322.35 | 4.34 | 4.21 | 4.82 | + |
| 33 | 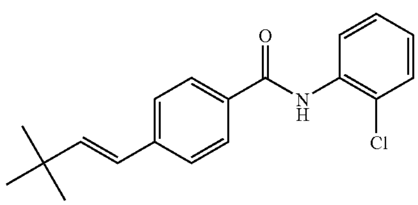 | 313.83 | 314.13 | 4.44 | 4.21 | 4.87 | + |
| 34 | 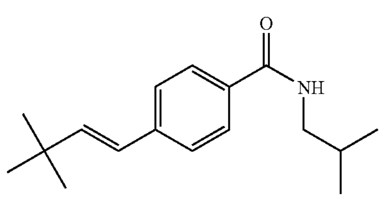 | 259.39 | 260.26 | 3.86 | 3.78 | 4.21 | |
| 35 | 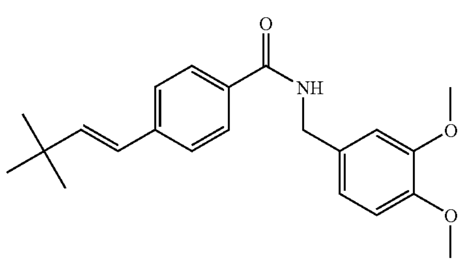 | 353.47 | 354.26 | 3.72 | 3.62 | 4.16 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 36 | 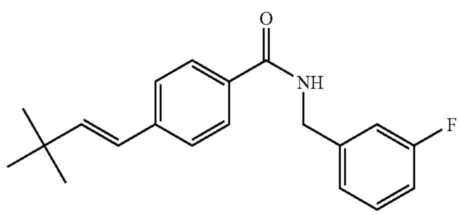 | 311.40 | 312.21 | 3.98 | 3.78 | 4.38 | |
| 37 | 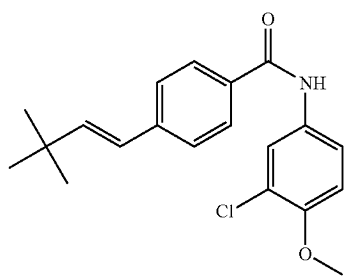 | 343.86 | 344.17 | 4.22 | 4.07 | 4.64 | + |
| 38 | 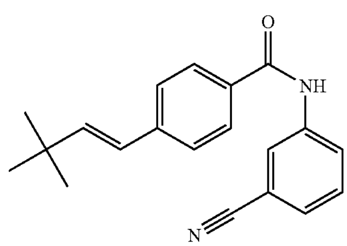 | 304.40 | 305.33 | 4.08 | 3.95 | 4.48 | + |
| 39 | 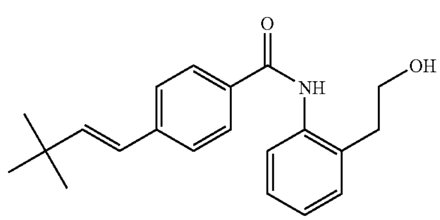 | 323.44 | 324.37 | 3.75 | 3.66 | 4.24 | ++++ |
| 40 | 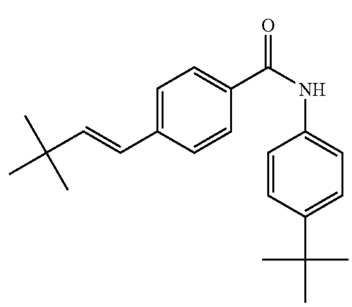 | 335.49 | 336.49 | 4.61 | 4.48 | 5.12 | +++ |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 41 | 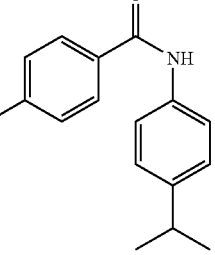 | 321.47 | 322.36 | 4.49 | 4.38 | 4.97 | ++ |
| 42 | 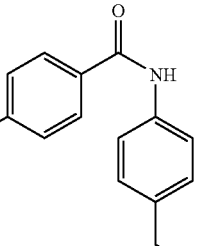 | 335.49 | 336.50 | 4.69 | 4.39 | 5.05 | + |
| 43 | 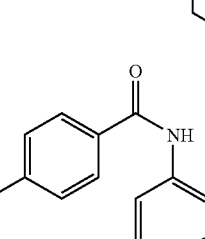 | 361.53 | 362.46 | 4.88 | 4.76 | 5.21 | + |
| 44 | 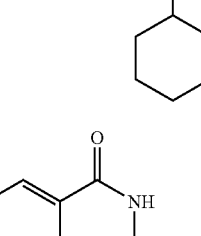 | 377.41 | 378.30 | 4.52 | 4.35 | 4.81 | ++++ |
| 45 | 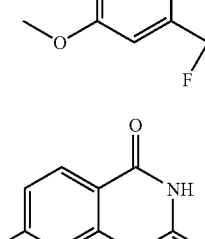 | 307.44 | 308.40 | 4.19 | 3.92 | 4.64 | ++++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 46 | 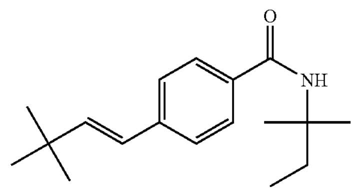 | 273.42 | 274.27 | 4.16 | 4.06 | 4.64 | |
| 47 | 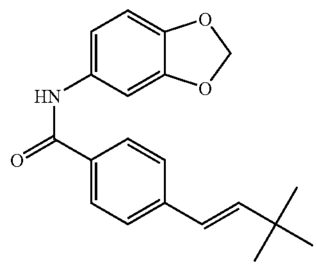 | 323.40 | 324.33 | 4.01 | 3.86 | 4.39 | ++++ |
| 48 | 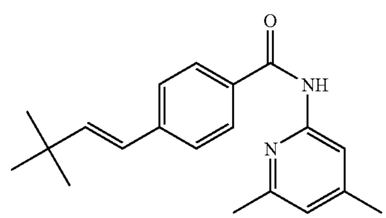 | 308.43 | 309.36 | 3.19 | 3.01 | 3.75 | ++ |
| 49 | 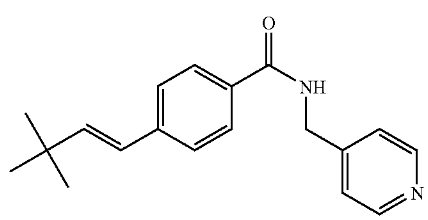 | 294.40 | 295.28 | 2.73 | 2.60 | 3.19 | ++++ |
| 50 | 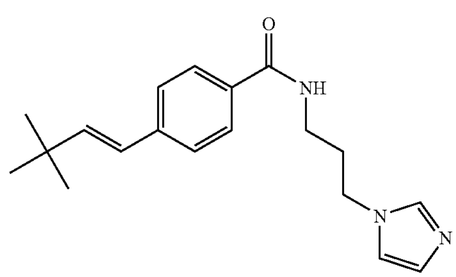 | 311.43 | 312.24 | 2.75 | 2.60 | 3.16 | |
| 51 | 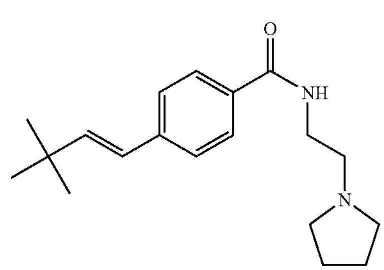 | 300.45 | 301.34 | 2.76 | 2.66 | 3.23 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 52 | 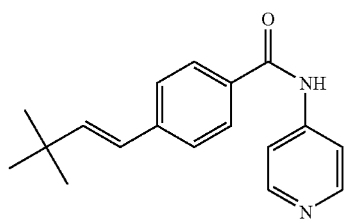 | 280.37 | 281.31 | 2.98 | 2.79 | 3.39 | ++++ |
| 53 | 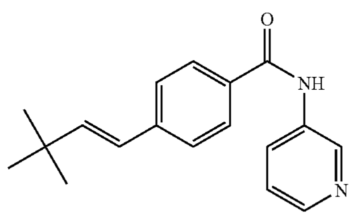 | 280.37 | 281.30 | 2.88 | 2.72 | 3.31 | ++++ |
| 54 | 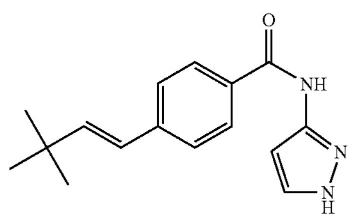 | 269.35 | 270.27 | 3.22 | 3.06 | 3.63 | + |
| 55 | 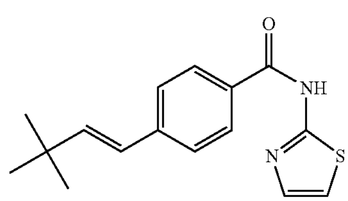 | 286.40 | 287.10 | 3.83 | 3.72 | 4.09 | + |
| 56 | 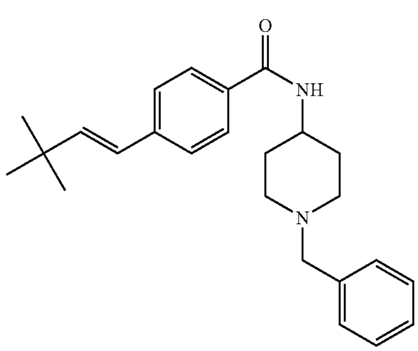 | 376.55 | 377.40 | 3.12 | 3.00 | 3.42 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 57 | 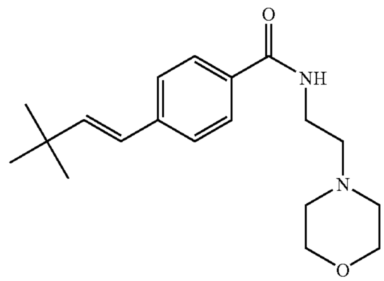 | 316.45 | 317.25 | 2.72 | 2.40 | 3.08 | |
| 58 | 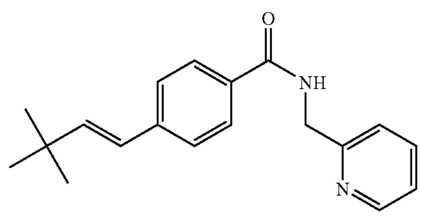 | 294.40 | 295.28 | 2.72 | 2.48 | 3.31 | |
| 59 | 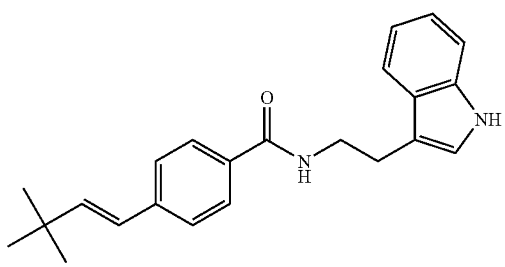 | 346.48 | 347.27 | 3.92 | 3.74 | 4.30 | |
| 60 | 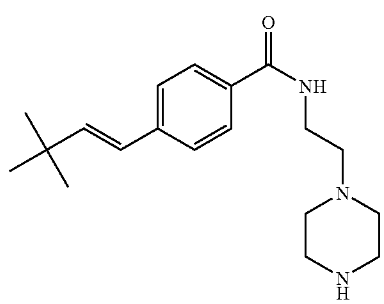 | 315.46 | 316.28 | 2.45 | 2.19 | 2.63 | + |
| 61 | 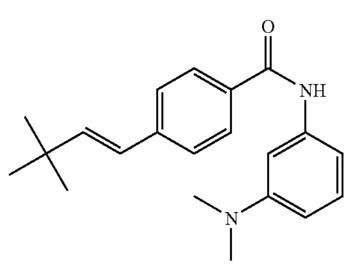 | 322.45 | 323.24 | 3.06 | 2.72 | 3.46 | ++++ |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 62 | 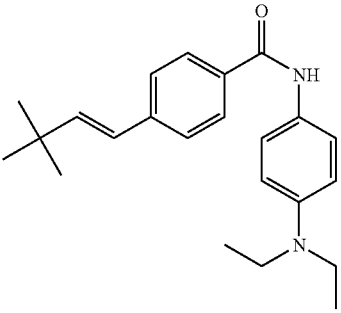 | 350.51 | 351.42 | 3.18 | 3.05 | 3.53 | ++++ |
| 63 | 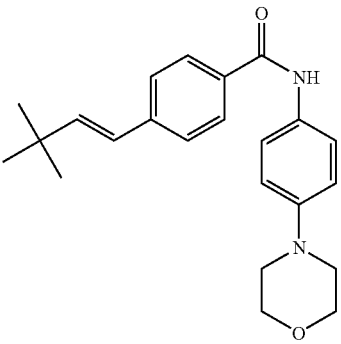 | 364.49 | 365.26 | 3.31 | 3.19 | 3.54 | |
| 64 | 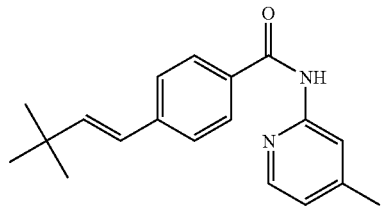 | 294.40 | 295.30 | 3.08 | 2.91 | 3.48 | + |
| 65 | 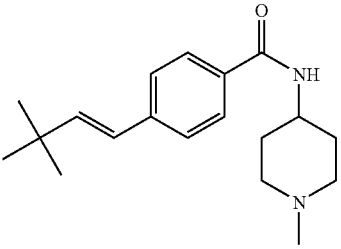 | 300.45 | 301.34 | 2.75 | 2.68 | 3.06 | + |
| 66 | 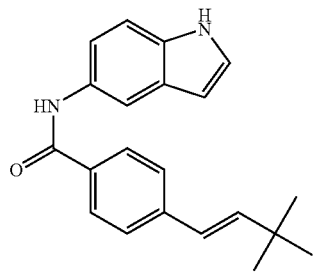 | 318.42 | 319.08 | 3.82 | 3.73 | 4.24 | ++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 67 | 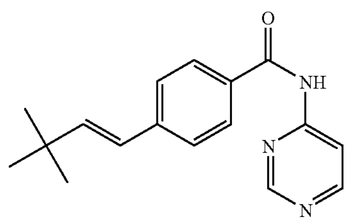 | 281.36 | 282.29 | 3.29 | 3.22 | 3.65 | + |
| 68 | 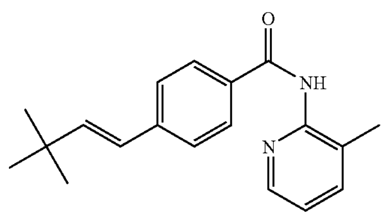 | 294.40 | 295.28 | 3.00 | 2.52 | 3.39 | +++ |
| 69 | 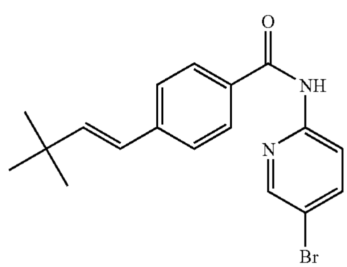 | 359.27 | 359.14 | 4.39 | 4.21 | 4.82 | + |
| 70 | 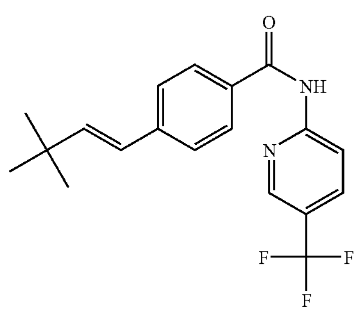 | 348.37 | 349.28 | 4.46 | 4.19 | 4.79 | + |
| 71 | 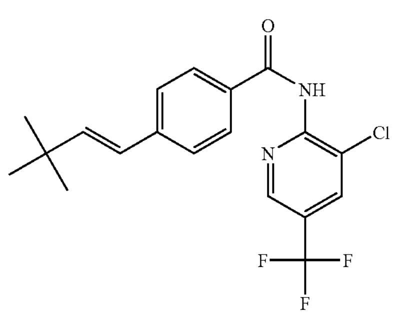 | 382.82 | 383.15 | 4.21 | 4.02 | 4.48 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 72 | 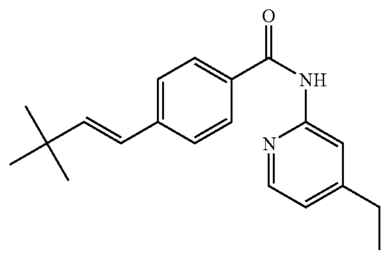 | 308.43 | 309.39 | 3.23 | 2.95 | 3.55 | + |
| 73 | 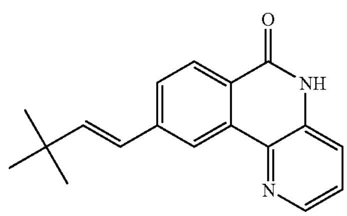 | 314.82 | 315.02 | 4.07 | 3.94 | 4.34 | |
| 74 | 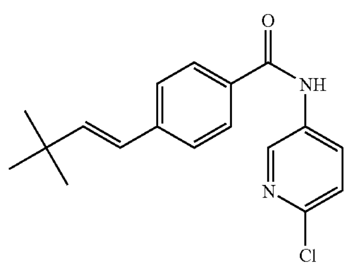 | 314.82 | 315.02 | 3.99 | 3.86 | 4.41 | +++ |
| 75 | 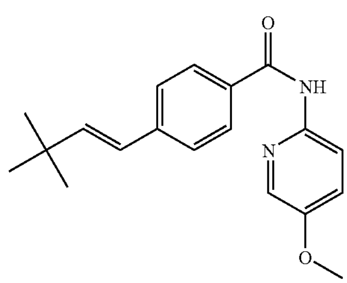 | 310.40 | 311.32 | 3.64 | 3.56 | 4.08 | ++ |
| 76 | 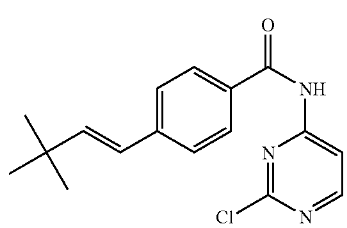 | 314.82 | 315.06 | 4.06 | 3.95 | 4.42 | ++++ |
| 77 | 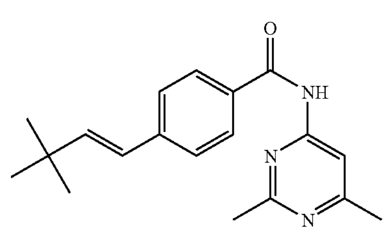 | 309.41 | 310.43 | 3.11 | 2.83 | 3.36 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 78 | 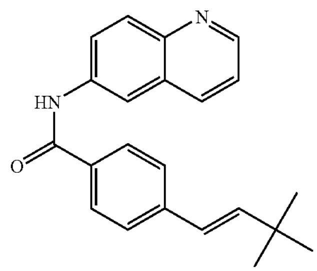 | 330.43 | 331.27 | 3.11 | 2.93 | 3.74 | ++++ |
| 79 | 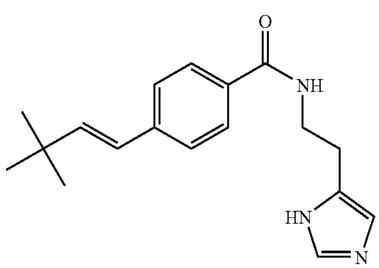 | 297.40 | 298.32 | 2.76 | 2.72 | 2.92 | |
| 80 | 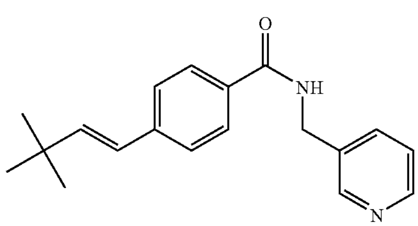 | 294.40 | 295.27 | 2.69 | 2.43 | 3.03 | + |
| 81 | 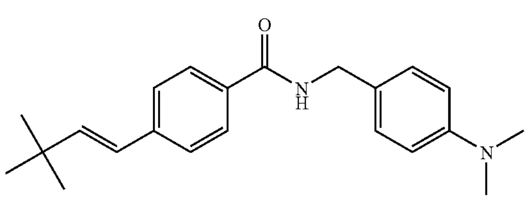 | 336.48 | 337.47 | 2.99 | 2.72 | 3.36 | + |
| 82 | 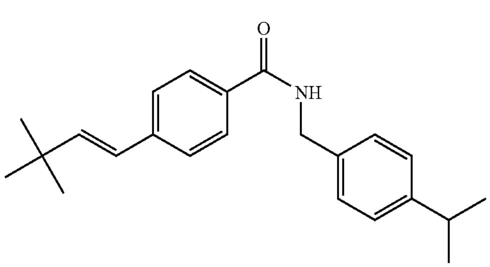 | 335.49 | 336.49 | 4.41 | 4.29 | 4.74 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 83 | 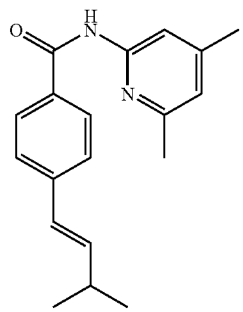 | 294.40 | 295.27 | 3.00 | 2.89 | 3.53 | |
| 84 | 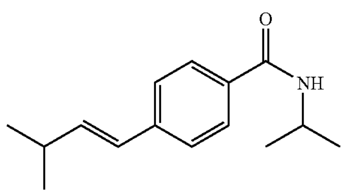 | 231.34 | 232.17 | 3.51 | 3.36 | 3.96 | |
| 85 | 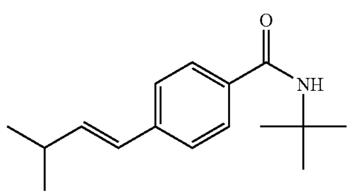 | 245.37 | 246.20 | 3.82 | 3.62 | 4.22 | |
| 86 | 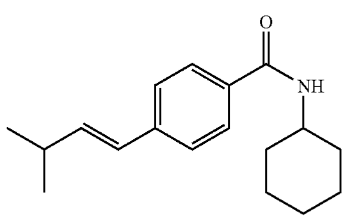 | 271.41 | 272.26 | 3.92 | 3.78 | 4.31 | |
| 87 | 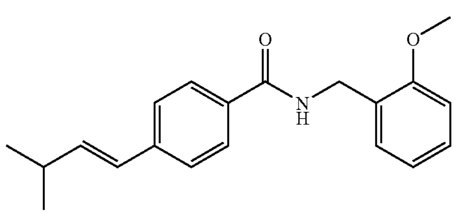 | 309.41 | 310.39 | 3.83 | 3.63 | 4.28 | + |
| 88 | 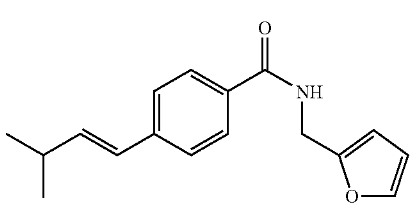 | 269.35 | 270.27 | 3.58 | 3.46 | 3.99 | ++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 89 | 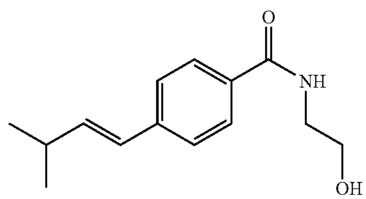 | 233.31 | 234.16 | 2.83 | 2.75 | 3.22 | |
| 90 | 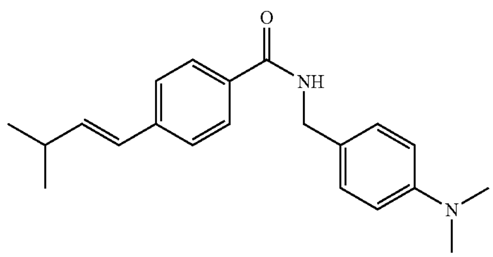 | 322.45 | 323.22 | 2.80 | 2.63 | 2.90 | |
| 91 | 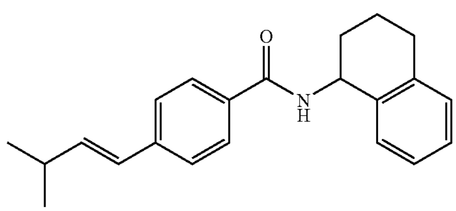 | 319.45 | 320.18 | 4.12 | 3.96 | 4.75 | |
| 92 | 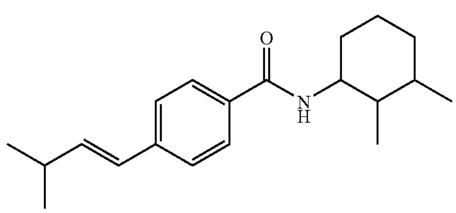 | 299.46 | 300.24 | 4.19 | 4.04 | 4.97 | |
| 93 | 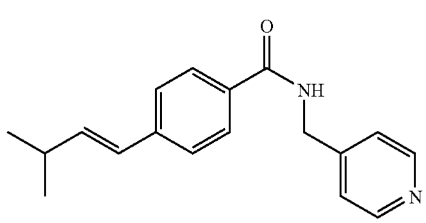 | 280.37 | 281.29 | 2.60 | 2.46 | 3.05 | + |
| 94 | 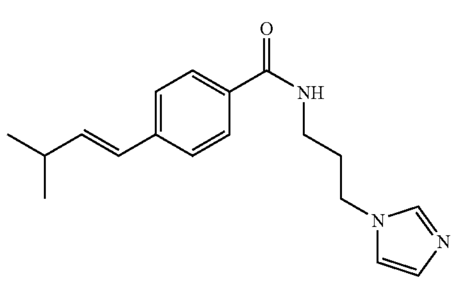 | 297.40 | 298.30 | 2.63 | 2.50 | 2.75 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 95 | 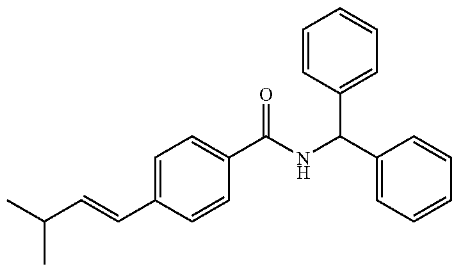 | 355.48 | 356.20 | 4.21 | 4.01 | 4.54 | ++ |
| 96 | 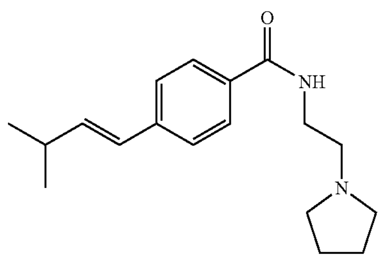 | 286.42 | 287.19 | 2.65 | 2.49 | 3.02 | |
| 97 | 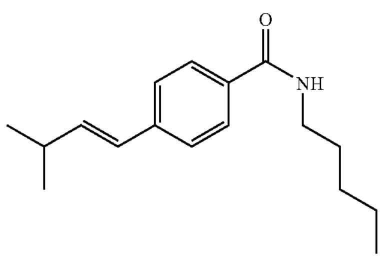 | 259.39 | 260.17 | 3.92 | 3.75 | 4.52 | |
| 98 | 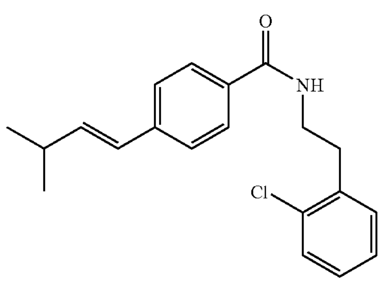 | 327.86 | 328.28 | 4.04 | 3.91 | 4.59 | + |
| 99 | 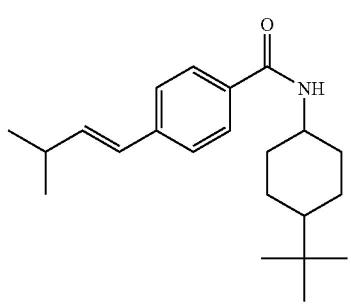 | 327.51 | 328.38 | 4.64 | 4.35 | 4.95 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 100 | 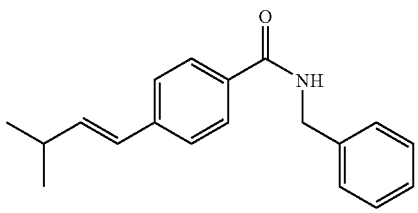 | 279.39 | 280.19 | 3.75 | 3.53 | 4.09 | |
| 101 | 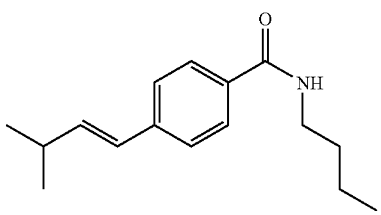 | 245.37 | 246.19 | 3.71 | 3.59 | 4.31 | |
| 102 | 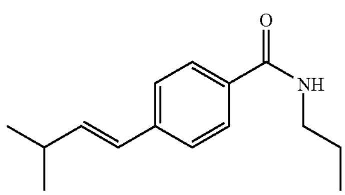 | 231.34 | 232.19 | 3.49 | 3.41 | 3.89 | |
| 103 | 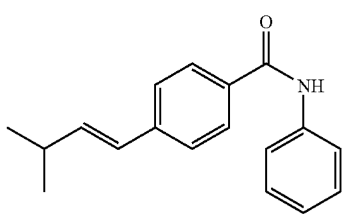 | 265.36 | 266.09 | 3.87 | 3.72 | 4.34 | |
| 104 | 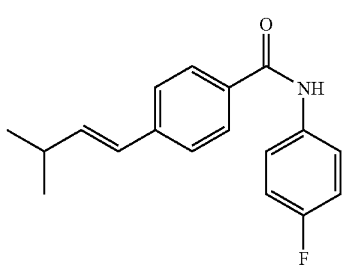 | 283.35 | 284.27 | 3.95 | 3.76 | 4.05 | |
| 105 | 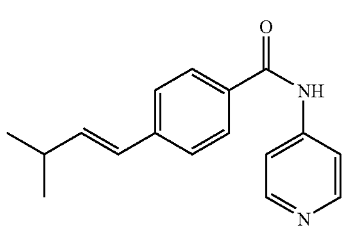 | 266.35 | 267.07 | 2.82 | 2.70 | 3.19 | ++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 106 | 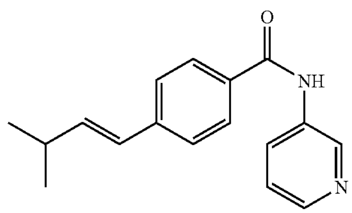 | 266.35 | 267.05 | 2.76 | 2.63 | 2.86 | ++ |
| 107 | 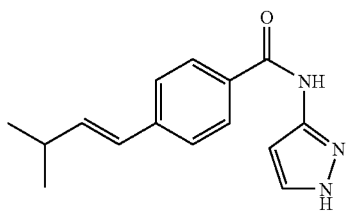 | 255.32 | 256.33 | 3.07 | 2.95 | 3.44 | |
| 108 | 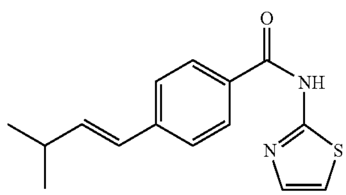 | 272.37 | 273.11 | 3.65 | 3.43 | 4.02 | |
| 109 | 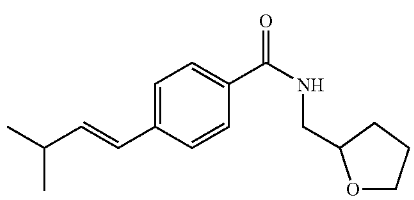 | 273.38 | 274.17 | 3.32 | 3.21 | 3.81 | ++ |
| 110 | 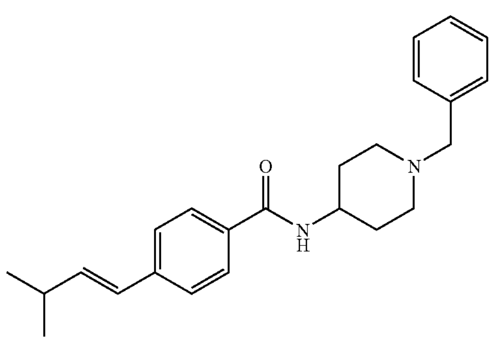 | 362.52 | 363.42 | 2.95 | 2.84 | 3.36 | |
| 111 | 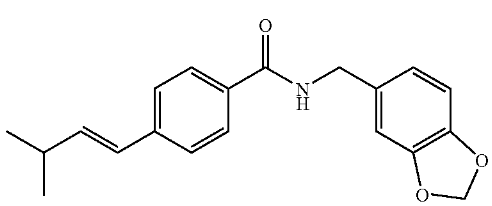 | 323.40 | 324.31 | 3.69 | 3.56 | 4.08 | +++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 112 | 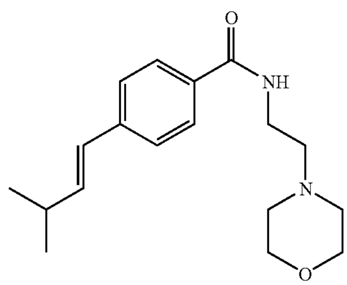 | 302.42 | 303.14 | 2.61 | 2.51 | 2.72 | ++ |
| 113 | 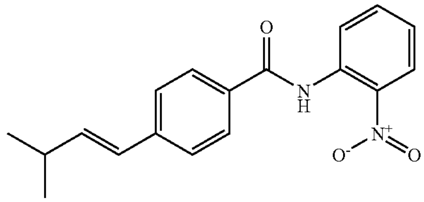 | 310.36 | 311.31 | 4.34 | 4.24 | 4.57 | |
| 114 | 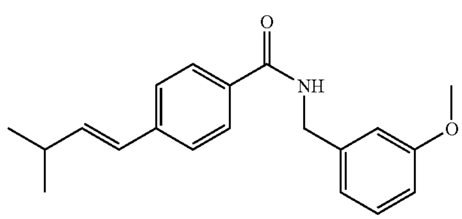 | 309.41 | 310.40 | 3.78 | 3.62 | 4.11 | |
| 115 | 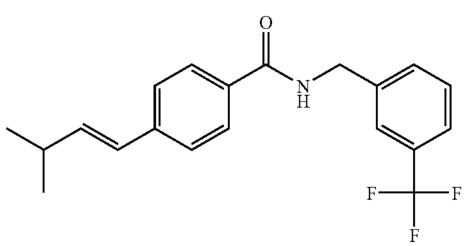 | 347.38 | 348.17 | 4.04 | 3.92 | 4.39 | |
| 116 | 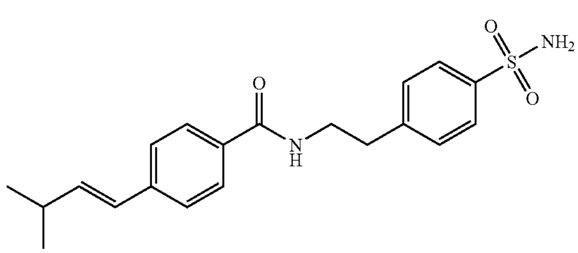 | 372.49 | 373.17 | 3.22 | 3.13 | 3.58 | + |

US 7,432,281 B2
TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 117 | 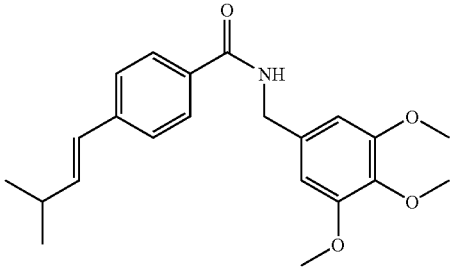 | 369.46 | 370.14 | 3.56 | 3.48 | 3.95 | + |
| 118 | 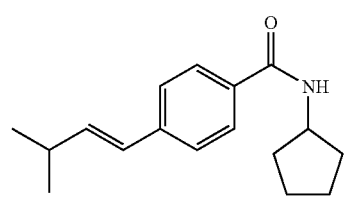 | 257.38 | 258.25 | 3.74 | 3.62 | 4.18 | |
| 119 | 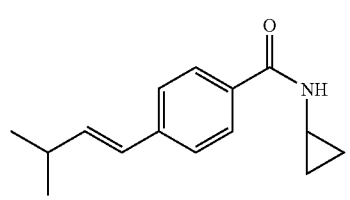 | 229.32 | 230.25 | 3.31 | 3.22 | 3.69 | |
| 120 | 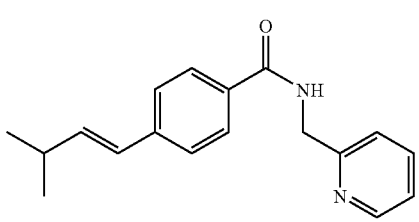 | 280.37 | 281.29 | 2.62 | 2.51 | 2.76 | + |
| 121 | 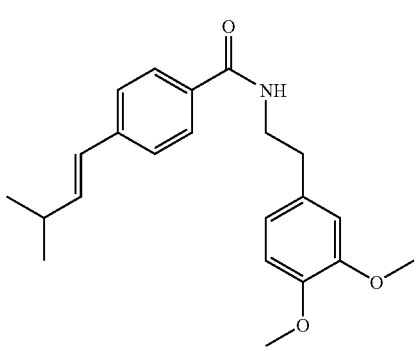 | 353.47 | 354.19 | 3.61 | 3.49 | 4.02 | +++ |
| 122 | 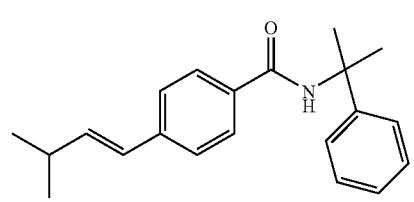 | 307.44 | 308.40 | 4.01 | 3.89 | 4.31 | |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 123 | 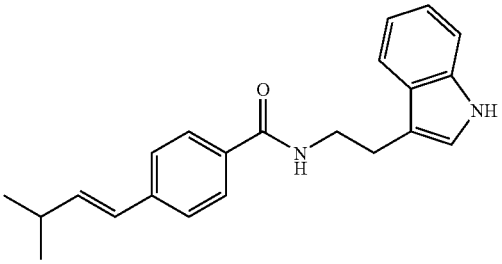 | 332.45 | 333.27 | 3.75 | 3.61 | 4.18 | + |
| 124 | 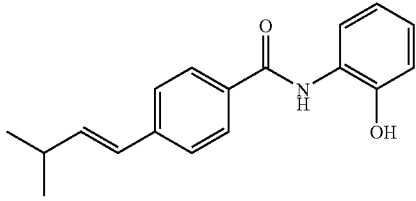 | 281.36 | 282.30 | 3.73 | 3.65 | 4.08 | |
| 125 | 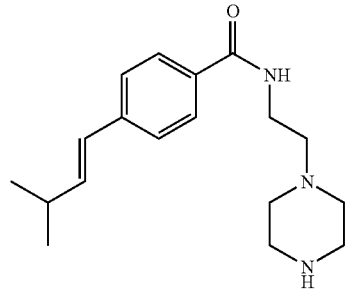 | 301.44 | 302.32 | 2.33 | 2.28 | 2.65 | ++++ |
| 126 | 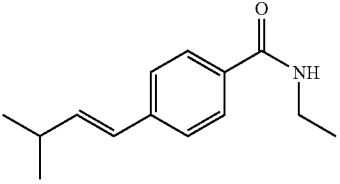 | 217.31 | 218.25 | 3.31 | 3.18 | 3.96 | ++ |
| 127 | 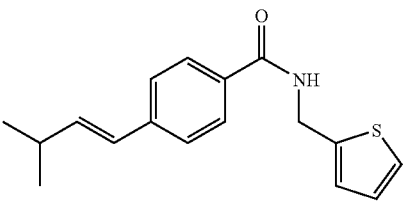 | 285.41 | 286.12 | 3.71 | 3.59 | 4.19 | ++ |
| 128 | 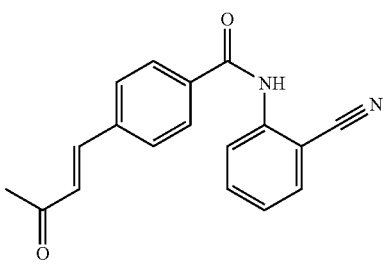 | 290.37 | 291.12 | 3.73 | 3.62 | 4.58 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 129 | 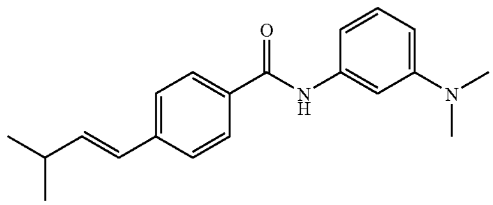 | 308.43 | 309.34 | 2.93 | 2.75 | 3.03 | |
| 130 | 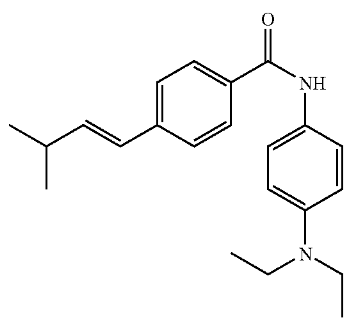 | 336.48 | 337.42 | 3.03 | 2.92 | 3.49 | +++ |
| 131 | 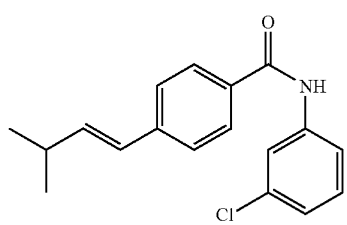 | 299.80 | 300.15 | 4.18 | 3.98 | 4.55 | |
| 132 | 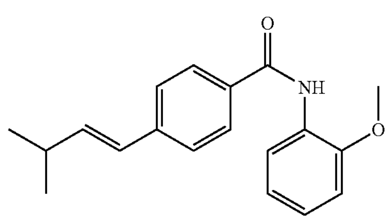 | 295.38 | 296.26 | 4.15 | 3.99 | 4.45 | + |
| 133 | 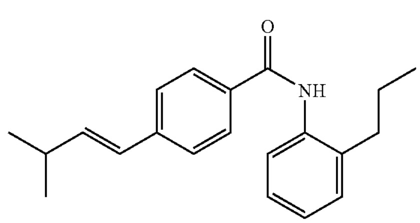 | 307.44 | 308.39 | 4.17 | 3.98 | 4.77 | |
| 134 | 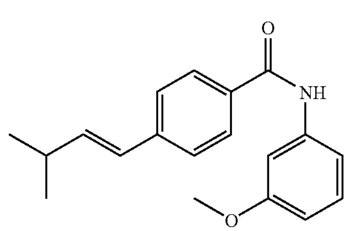 | 295.38 | 296.26 | 3.91 | 3.71 | 4.46 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 135 | 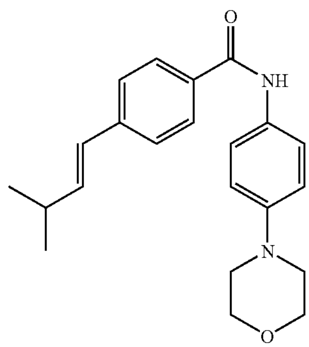 | 350.46 | 351.36 | 3.16 | 3.03 | 3.56 | |
| 136 | 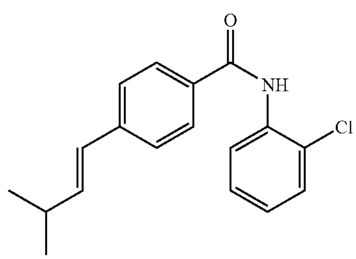 | 299.80 | 300.15 | 4.25 | 4.05 | 4.66 | + |
| 137 | 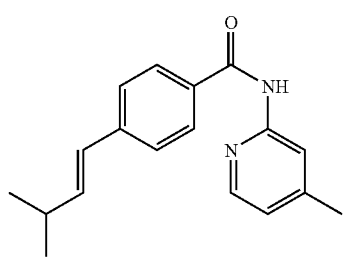 | 280.37 | 281.30 | 2.92 | 2.83 | 3.26 | |
| 138 | 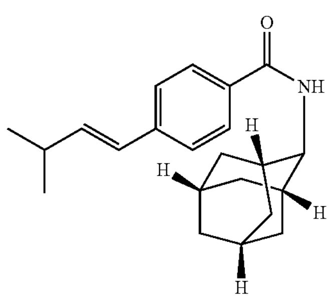 | 323.48 | 324.41 | 4.45 | 4.35 | 4.84 | |
| 139 | 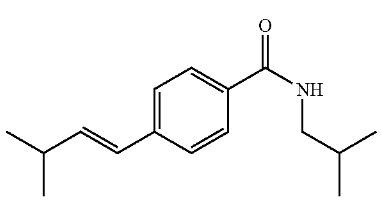 | 245.37 | 246.19 | 3.69 | 3.49 | 4.32 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 140 | 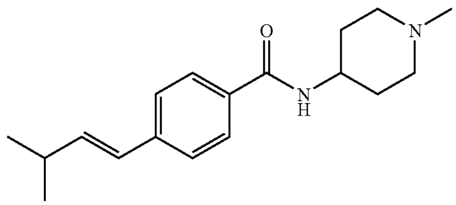 | 286.42 | 287.18 | 2.62 | 2.45 | 2.91 | |
| 141 | 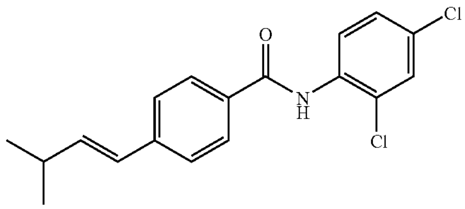 | 334.25 | 334.12 | 4.62 | 4.45 | 4.85 | |
| 142 | 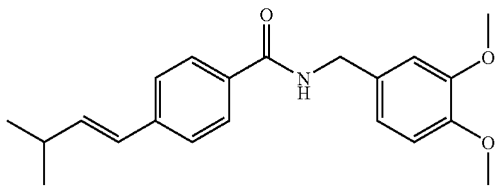 | 339.44 | 340.17 | 3.55 | 3.44 | 3.91 | + |
| 143 | 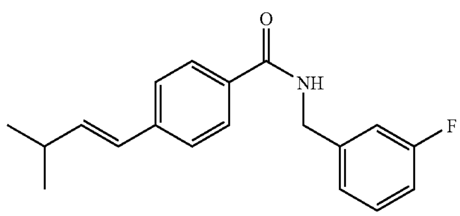 | 297.38 | 298.24 | 3.82 | 3.68 | 4.25 | + |
| 144 | 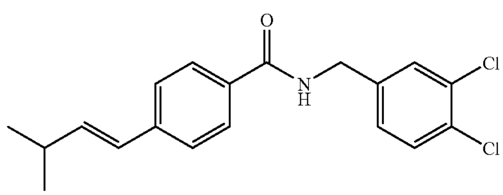 | 348.28 | 348.13 | 4.19 | 4.04 | 4.66 | |
| 145 | 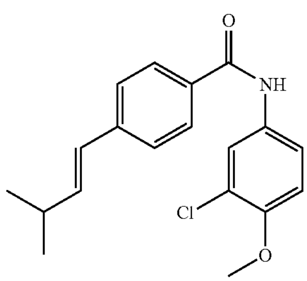 | 329.83 | 330.12 | 4.04 | 3.92 | 4.45 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 146 | 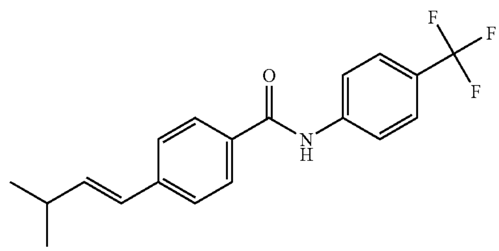 | 333.36 | 334.22 | 4.36 | 4.19 | 4.78 | |
| 147 | 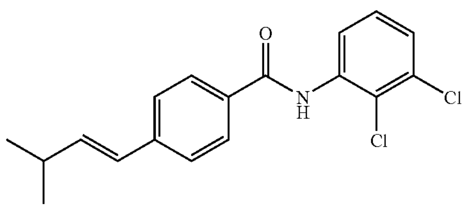 | 334.25 | 334.11 | 4.54 | 4.42 | 4.74 | |
| 148 | 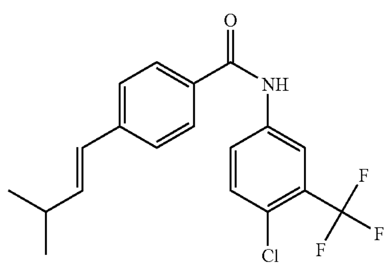 | 367.80 | 368.10 | 4.47 | 4.37 | 4.89 | + |
| 149 | 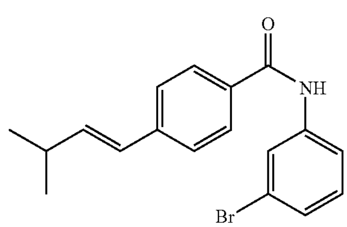 | 344.25 | 345.96 | 4.26 | 4.09 | 4.62 | |
| 150 | 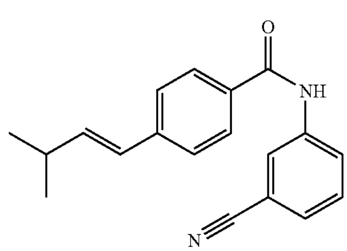 | 290.37 | 291.12 | 3.91 | 3.72 | 4.21 | ++ |
| 151 | 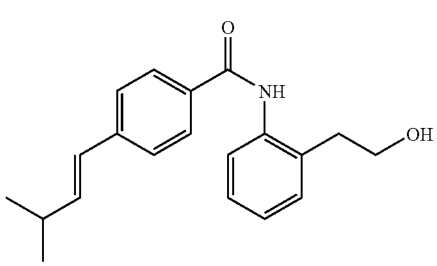 | 309.41 | 310.39 | 3.55 | 3.45 | 4.12 | +++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 152 | 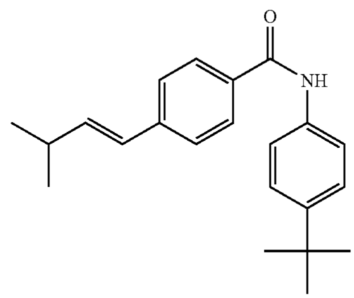 | 321.47 | 322.32 | 4.44 | 4.26 | 4.99 | |
| 153 | 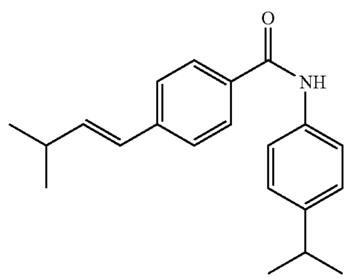 | 307.44 | 308.38 | 4.32 | 4.16 | 4.79 | ++++ |
| 154 | 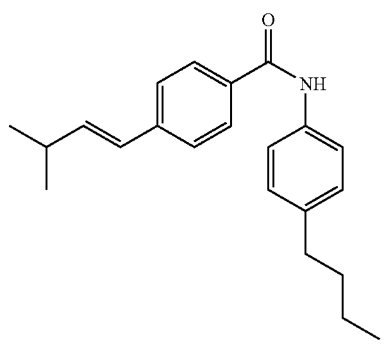 | 321.47 | 322.32 | 4.54 | 4.25 | 5.05 | |
| 155 | 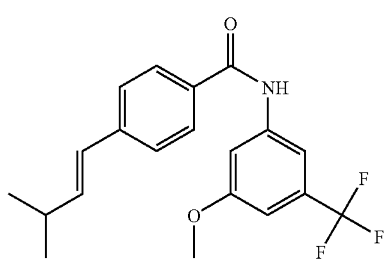 | 363.38 | 364.29 | 4.32 | 4.06 | 4.55 | |
| 156 | 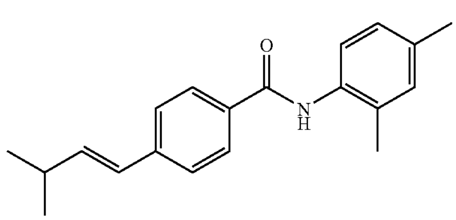 | 293.41 | 294.16 | 4.02 | 3.88 | 4.76 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 157 | 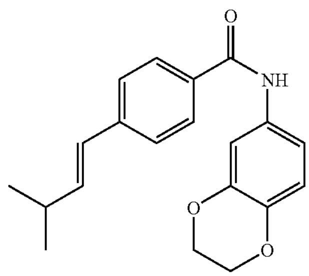 | 323.40 | 324.31 | 3.81 | 3.68 | 4.68 | |
| 158 | 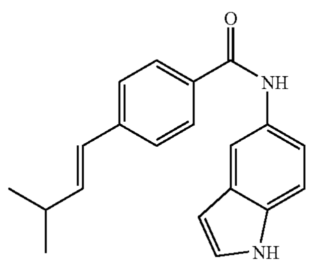 | 304.40 | 305.29 | 3.66 | 3.56 | 4.02 | ++ |
| 159 | 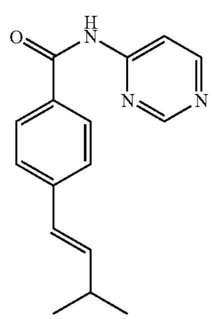 | 267.33 | 268.16 | 3.13 | 3.05 | 3.22 | |
| 160 | 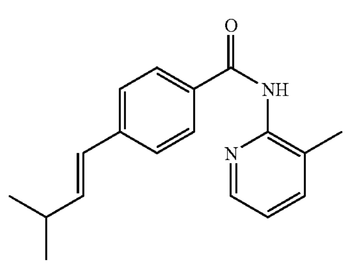 | 280.37 | 281.29 | 2.88 | 2.79 | 2.95 | |
| 161 | 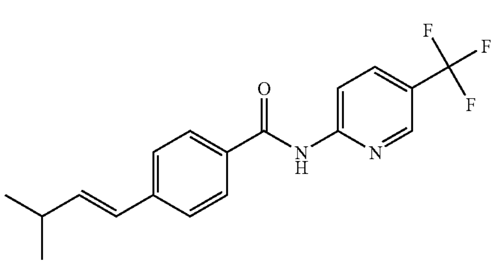 | 334.34 | 335.32 | 4.29 | 4.12 | 4.64 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 162 | 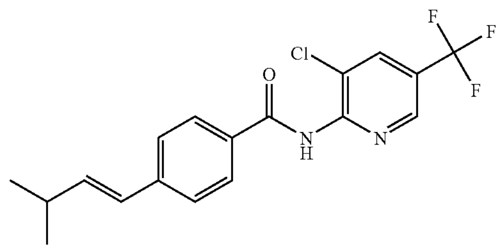 | 368.79 | 369.07 | 4.01 | 3.78 | 4.35 | |
| 163 | 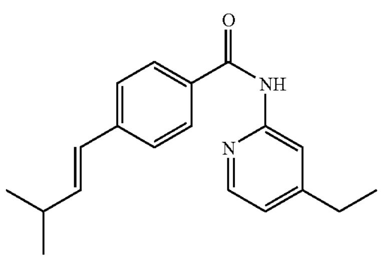 | 294.40 | 295.28 | 3.08 | 2.92 | 3.35 | |
| 164 | 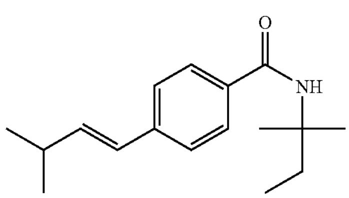 | 259.39 | 260.17 | 3.97 | 3.84 | 4.88 | + |
| 165 | 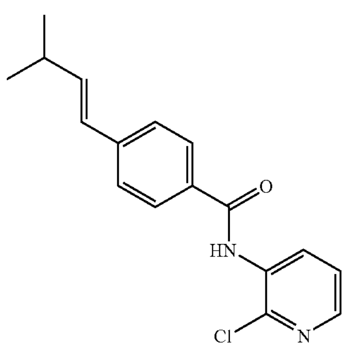 | 300.79 | 301.19 | 3.85 | 3.71 | 4.42 | |
| 166 | 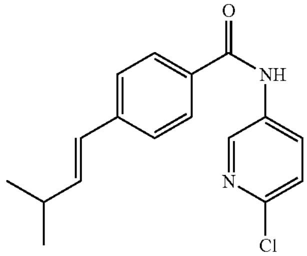 | 300.79 | 301.19 | 3.79 | 3.64 | 4.32 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 167 | 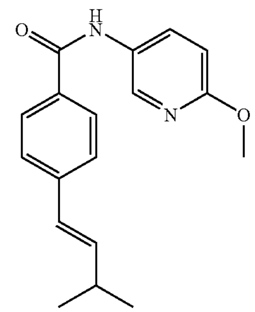 | 296.37 | 297.31 | 3.46 | 3.38 | 3.76 | |
| 168 | 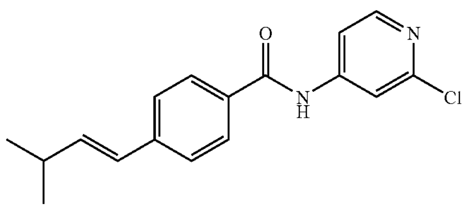 | 300.79 | 301.19 | 3.86 | 3.75 | 4.15 | + |
| 169 | 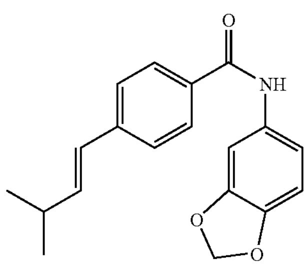 | 309.37 | 310.34 | 3.80 | 3.68 | 4.17 | +++ |
| 170 | 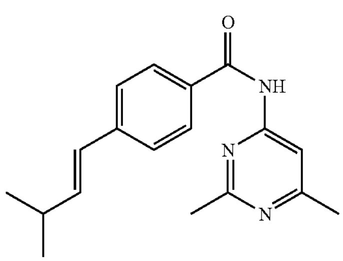 | 295.39 | 296.32 | 2.98 | 2.89 | 3.13 | |
| 171 | 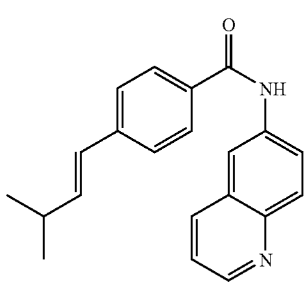 | 316.41 | 317.19 | 2.96 | 2.79 | 3.43 | ++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 172 | 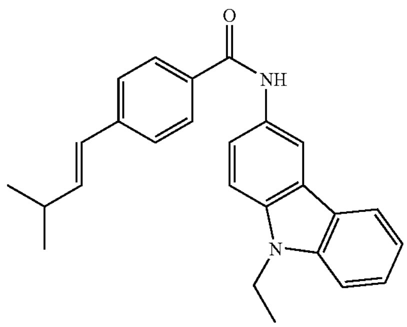 | 382.51 | 383.27 | 4.38 | 4.15 | 5.04 | ++ |
| 173 | 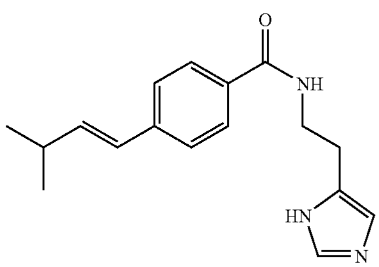 | 283.38 | 284.27 | 2.59 | 2.42 | 2.92 | |
| 174 | 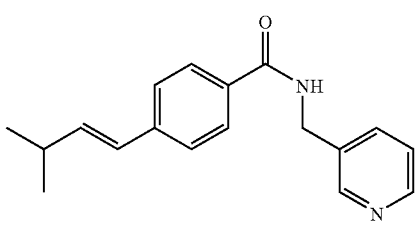 | 280.37 | 281.29 | 2.62 | 2.43 | 2.98 | |
| 175 | 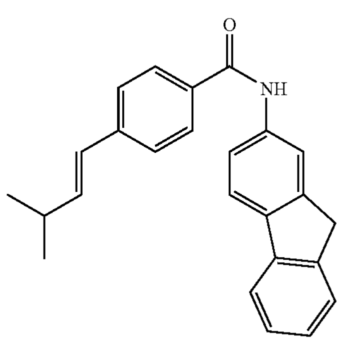 | 353.47 | 354.18 | 4.44 | 4.21 | 4.74 | + |
| 176 | 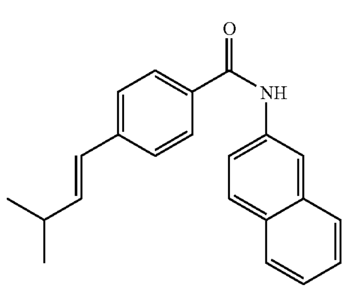 | 315.42 | 316.19 | 4.25 | 4.06 | 4.56 | |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 177 | 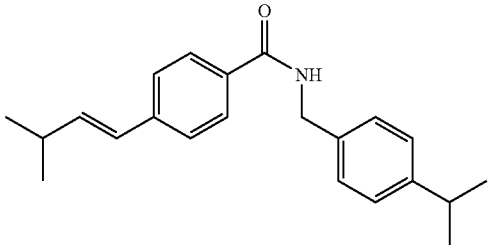 | 321.47 | 322.30 | 4.24 | 4.11 | 4.74 | |
| 178 | 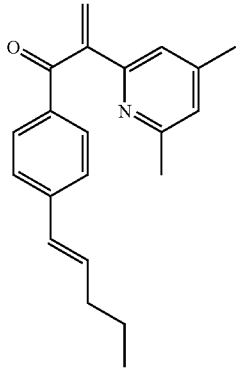 | 294.40 | 295.26 | 2.76 | 2.63 | 3.25 | |
| 179 | 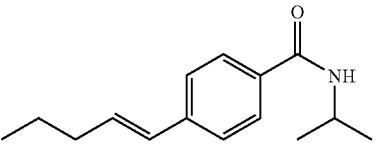 | 231.34 | 232.17 | 3.53 | 3.41 | 3.92 | + |
| 180 | 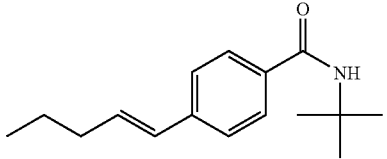 | 245.37 | 246.20 | 3.86 | 3.73 | 4.64 | |
| 181 | 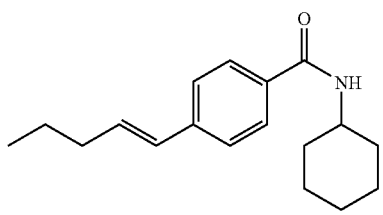 | 271.41 | 272.27 | 3.95 | 3.75 | 4.41 | + |
| 182 | 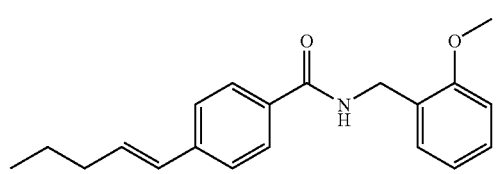 | 309.41 | 310.38 | 3.86 | 3.65 | 4.19 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 183 | 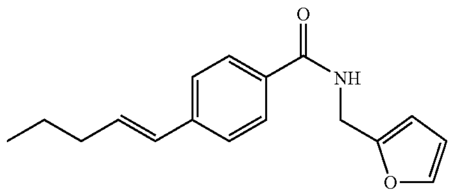 | 269.35 | 270.24 | 3.63 | 3.55 | 3.98 | + |
| 184 | 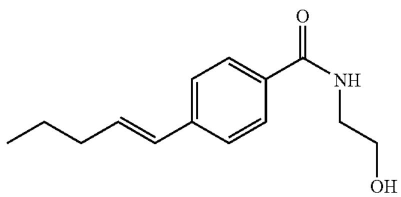 | 233.31 | 234.15 | 2.88 | 2.79 | 3.29 | |
| 185 | 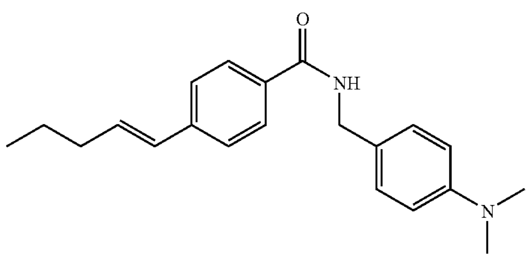 | 322.45 | 323.21 | 2.83 | 2.59 | 3.11 | + |
| 186 | 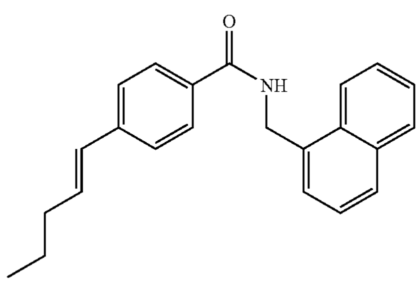 | 329.45 | 330.19 | 4.12 | 3.92 | 4.51 | |
| 187 | 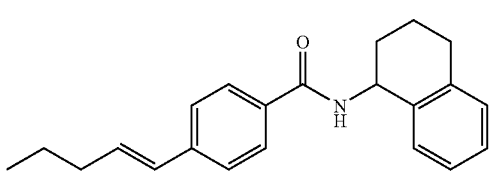 | 319.45 | 320.16 | 4.18 | 4.08 | 4.48 | |
| 188 | 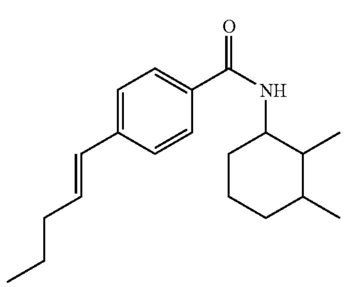 | 299.46 | 300.23 | 4.22 | 3.95 | 4.78 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 189 | 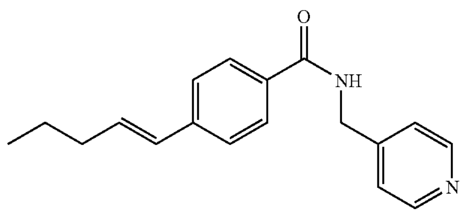 | 280.37 | 281.28 | 2.66 | 2.55 | 3.11 | |
| 190 | 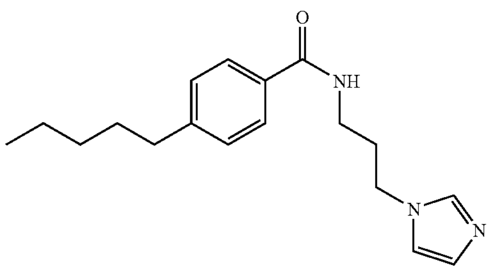 | 297.40 | 298.27 | 2.66 | 2.55 | 3.12 | + |
| 191 | 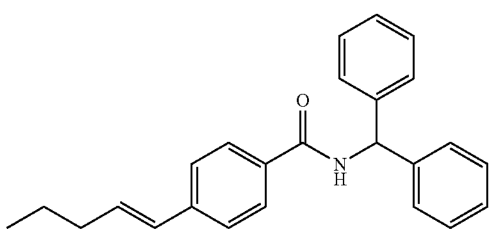 | 355.48 | 356.19 | 4.25 | 4.15 | 4.81 | + |
| 192 | 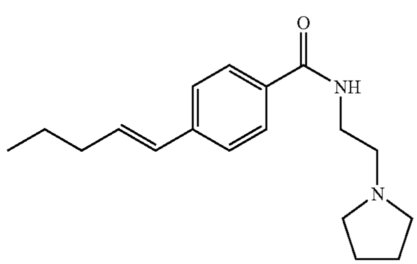 | 286.42 | 287.18 | 2.68 | 2.58 | 3.02 | + |
| 193 | 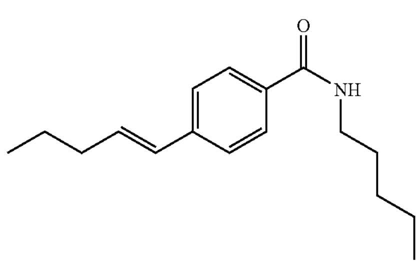 | 259.39 | 260.17 | 3.98 | 3.76 | 4.68 | ++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 194 | 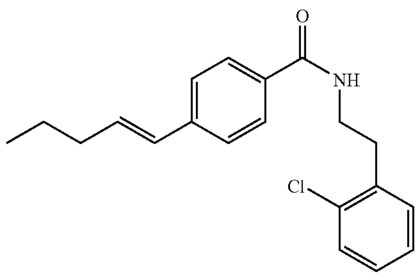 | 327.86 | 328.28 | 3.84 | 3.51 | 4.21 | + |
| 195 | 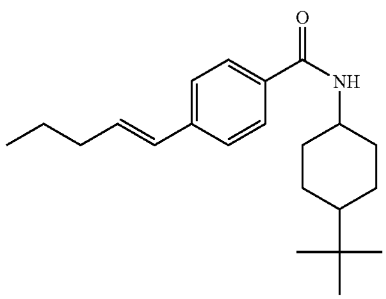 | 327.51 | 328.37 | 4.71 | 4.42 | 5.14 | |
| 196 | 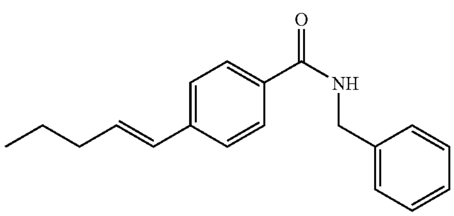 | 279.39 | 280.16 | 3.81 | 3.61 | 4.46 | + |
| 197 | 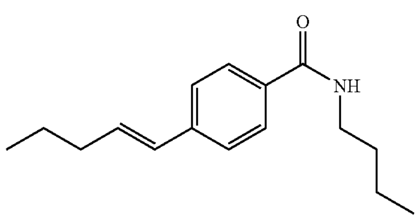 | 245.37 | 246.20 | 3.75 | 3.63 | 4.26 | + |
| 198 | 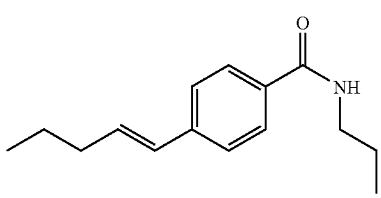 | 231.34 | 232.18 | 3.55 | 3.43 | 4.06 | ++ |
| 199 | 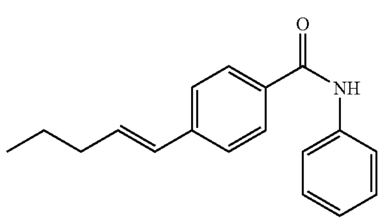 | 265.36 | 266.09 | 3.96 | 3.83 | 4.24 | |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 200 | 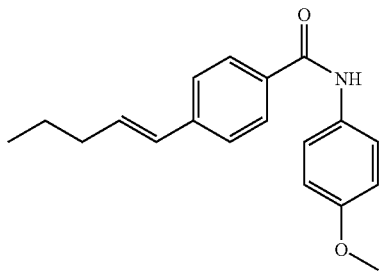 | 295.38 | 296.20 | 3.61 | 3.51 | 3.89 | |
| 201 | 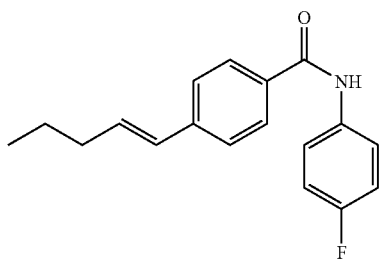 | 283.35 | 284.27 | 4.02 | 3.79 | 4.16 | |
| 202 | 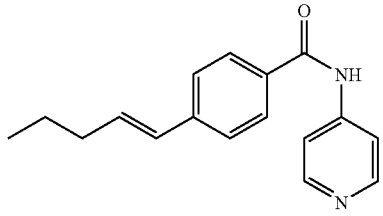 | 266.35 | 267.03 | 2.88 | 2.58 | 3.32 | + |
| 203 | 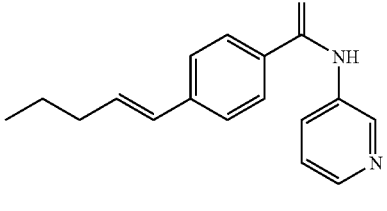 | 266.35 | 267.04 | 2.48 | 2.30 | 2.99 | + |
| 204 | 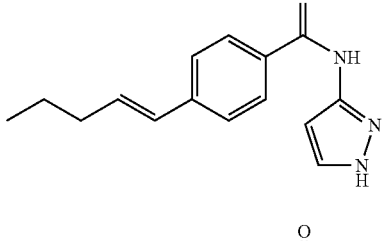 | 255.32 | 256.34 | 3.12 | 2.93 | 3.51 | + |
| 205 | 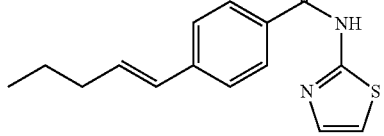 | 272.37 | 273.10 | 3.71 | 3.58 | 4.34 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 206 | 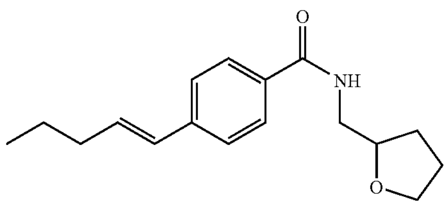 | 273.38 | 274.16 | 3.36 | 3.26 | 3.91 | + |
| 207 | 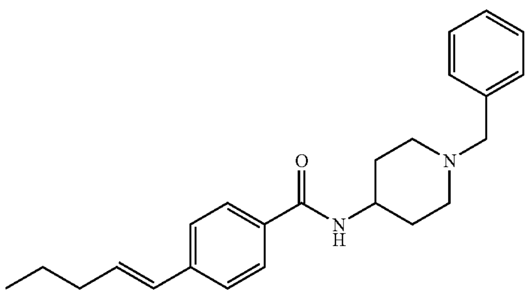 | 362.52 | 363.38 | 2.95 | 2.85 | 3.25 | ++ |
| 208 | 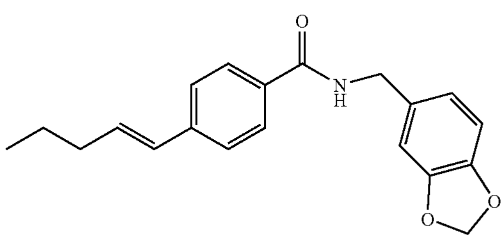 | 323.40 | 324.31 | 3.78 | 3.42 | 4.15 | + |
| 209 | 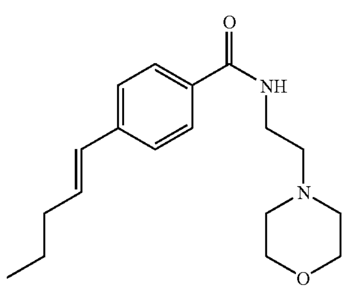 | 302.42 | 303.13 | 2.61 | 2.49 | 3.15 | + |
| 210 | 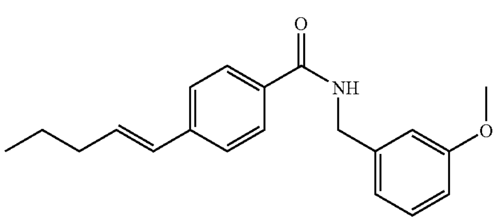 | 309.41 | 310.39 | 3.81 | 3.69 | 4.16 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 211 | 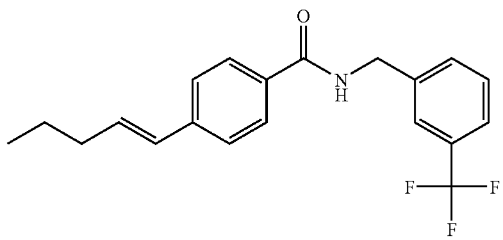 | 347.38 | 348.17 | 3.91 | 3.72 | 4.18 | + |
| 212 | 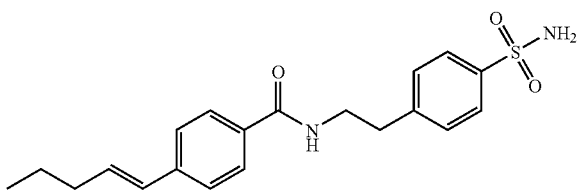 | 372.49 | 373.11 | 3.28 | 3.16 | 3.72 | |
| 213 | 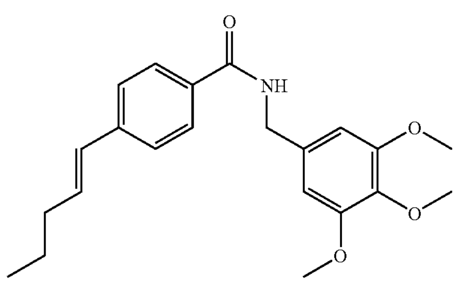 | 369.46 | 370.15 | 3.61 | 3.53 | 4.05 | + |
| 214 | 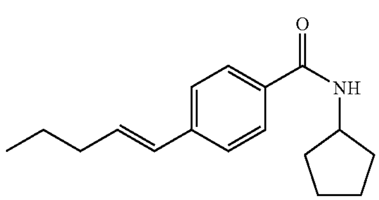 | 257.38 | 258.24 | 3.78 | 3.64 | 4.35 | + |
| 215 | 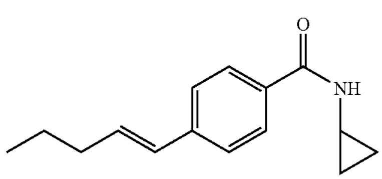 | 229.32 | 230.25 | 3.36 | 3.25 | 4.01 | |
| 216 | 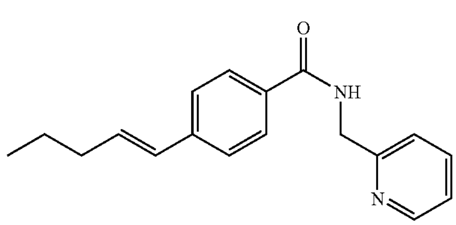 | 280.37 | 281.28 | 2.68 | 2.46 | 2.78 | + |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 217 | 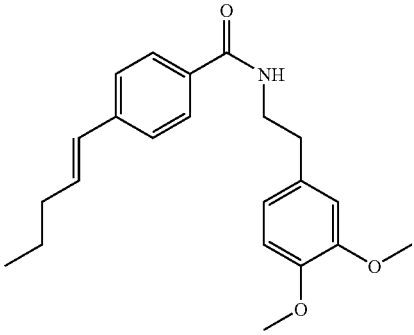 | 353.47 | 354.20 | 3.69 | 3.24 | 4.04 | + |
| 218 | 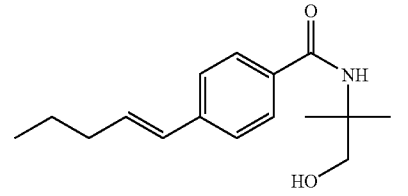 | 261.37 | 262.08 | 3.29 | 3.22 | 3.65 | + |
| 219 | 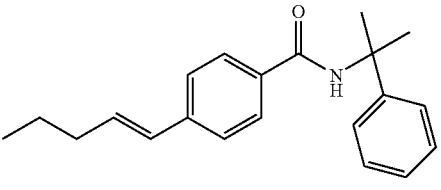 | 307.44 | 308.37 | 4.09 | 3.76 | 4.55 | + |
| 220 | 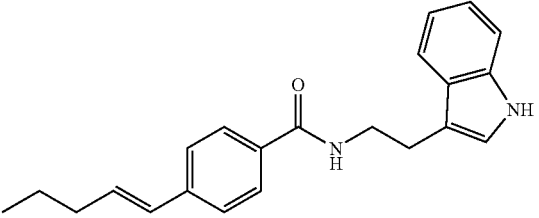 | 332.45 | 333.26 | 3.81 | 3.68 | 4.18 | |
| 221 | 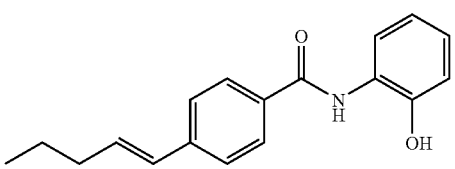 | 281.36 | 282.28 | 3.81 | 3.59 | 4.21 | |
| 222 | 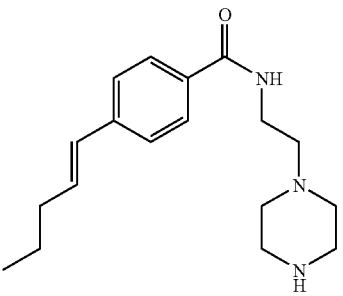 | 301.44 | 302.28 | 2.38 | 2.29 | 2.52 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 223 | *4-(pent-1-enyl)-N-ethylbenzamide* | 217.31 | 218.25 | 3.33 | 3.21 | 3.76 | +++ |
| 224 | *4-(pent-1-enyl)-N-(thiophen-2-ylmethyl)benzamide* | 285.41 | 286.10 | 3.76 | 3.59 | 4.15 | ++ |
| 225 | *4-(pent-1-enyl)-N-(2-cyanophenyl)benzamide* | 290.37 | 291.07 | 3.81 | 3.72 | 4.14 | + |
| 226 | *4-(pent-1-enyl)-N-(3-(dimethylamino)phenyl)benzamide* | 308.43 | 309.33 | 2.68 | 2.55 | 3.21 | +++ |
| 227 | *4-(pent-1-enyl)-N-(4-(diethylamino)phenyl)benzamide* | 336.48 | 337.41 | 2.79 | 2.64 | 3.19 | + |
| 228 | *4-(pent-1-enyl)-N-(3-chlorophenyl)benzamide* | 299.80 | 300.15 | 4.25 | 4.12 | 4.66 | +++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 229 | 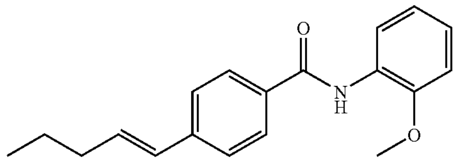 | 295.38 | 296.23 | 4.22 | 4.06 | 4.72 | |
| 230 | 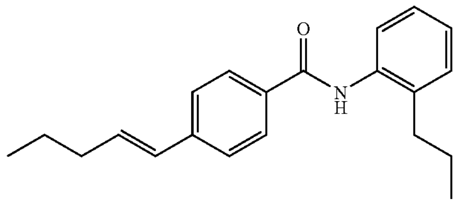 | 307.44 | 308.37 | 4.22 | 3.66 | 4.62 | + |
| 231 | 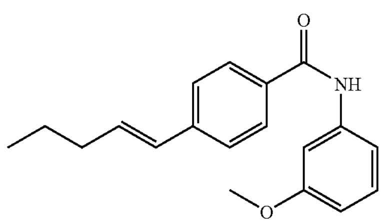 | 295.38 | 296.23 | 3.68 | 3.52 | 3.99 | |
| 232 | 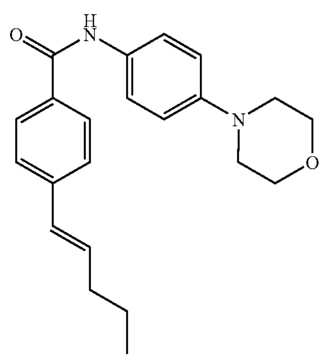 | 350.46 | 351.37 | 2.90 | 2.76 | 3.16 | |
| 233 | 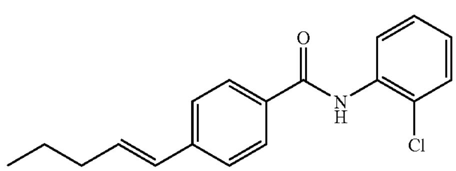 | 299.80 | 300.12 | 4.34 | 4.08 | 4.65 | + |
| 234 | 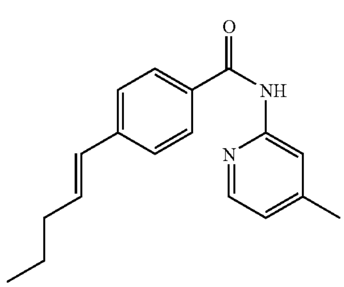 | 280.37 | 281.28 | 2.96 | 2.72 | 3.49 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 235 | 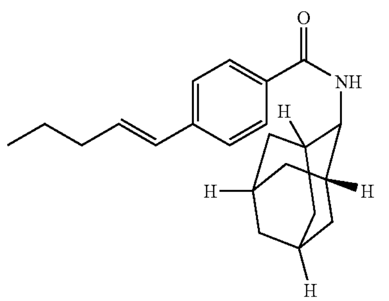 | 323.48 | 324.41 | 4.51 | 4.34 | 5.04 | |
| 236 | 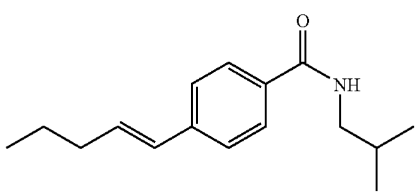 | 245.37 | 246.18 | 3.72 | 3.39 | 4.15 | + |
| 237 | 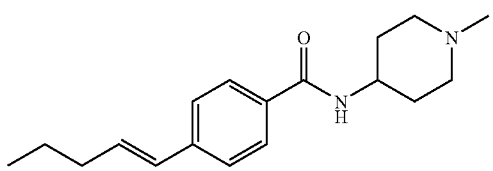 | 286.42 | 287.18 | 2.66 | 2.46 | 2.76 | + |
| 238 | 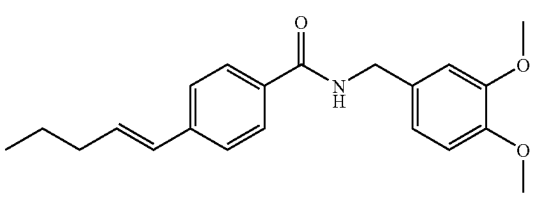 | 339.44 | 340.16 | 3.59 | 3.49 | 4.04 | + |
| 239 | 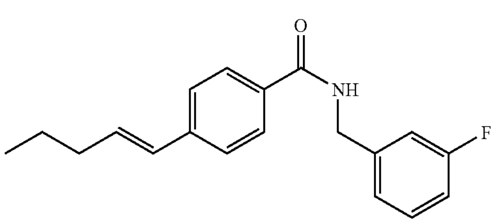 | 297.38 | 298.21 | 3.86 | 3.68 | 4.32 | ++ |
| 240 | 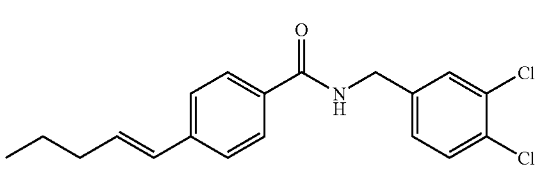 | 348.28 | 348.13 | 4.24 | 3.98 | 4.81 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 241 | 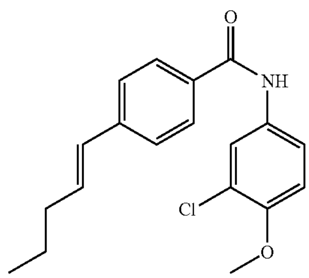 | 329.83 | 330.11 | 4.15 | 3.81 | 4.44 | |
| 242 | 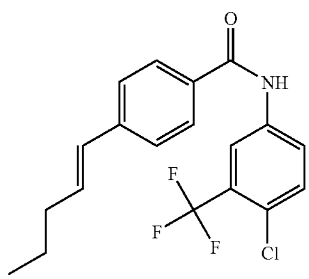 | 367.80 | 368.08 | 4.52 | 4.41 | 4.69 | ++ |
| 243 | 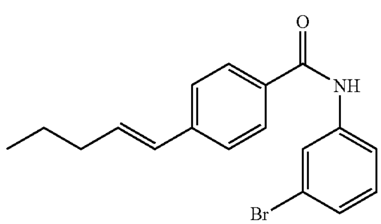 | 344.25 | 345.95 | 4.44 | 4.01 | 4.68 | |
| 244 | 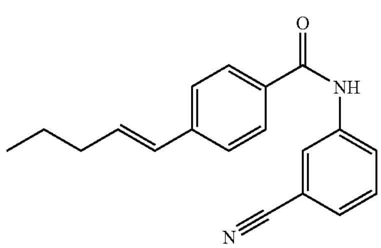 | 290.37 | 291.12 | 3.98 | 3.85 | 4.44 | ++ |
| 245 | 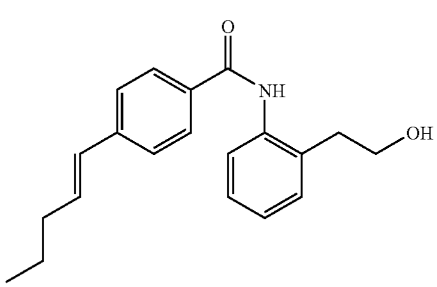 | 309.41 | 310.39 | 3.61 | 3.51 | 3.86 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 246 | 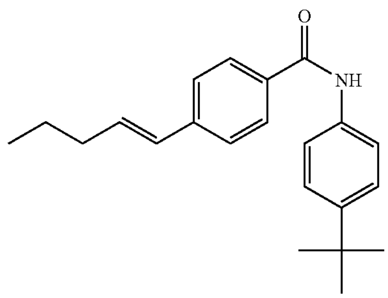 | 321.47 | 322.30 | 4.48 | 4.24 | 4.89 | + |
| 247 | 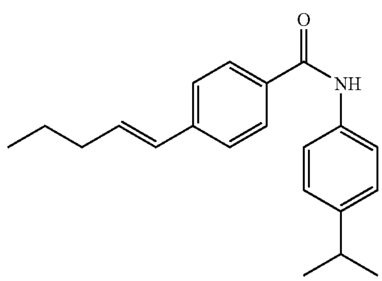 | 307.44 | 308.38 | 4.39 | 4.26 | 4.68 | + |
| 248 | 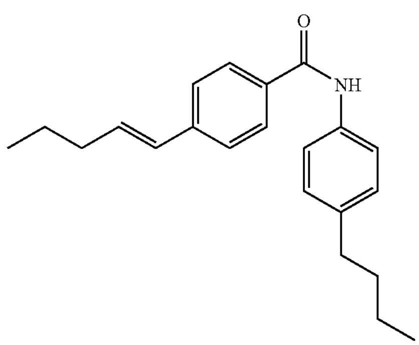 | 321.47 | 322.27 | 4.58 | 4.51 | 4.84 | +++ |
| 249 | 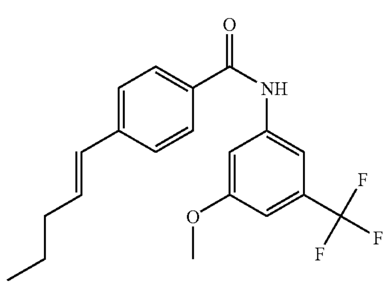 | 363.38 | 364.29 | 4.41 | 4.12 | 4.82 | + |
| 250 | 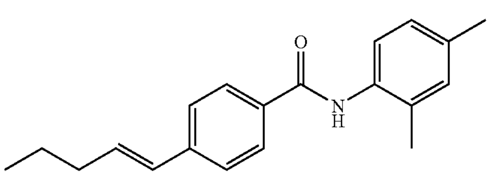 | 293.41 | 294.14 | 4.08 | 3.88 | 4.78 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 251 | 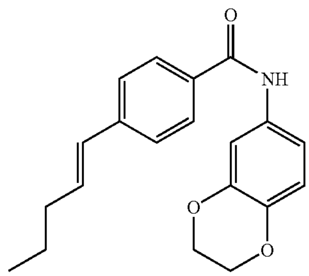 | 323.40 | 324.30 | 3.60 | 3.48 | 3.90 | |
| 252 | 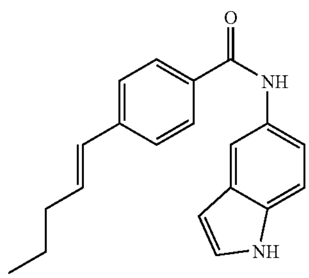 | 304.40 | 305.27 | 3.72 | 3.60 | 4.18 | + |
| 253 | 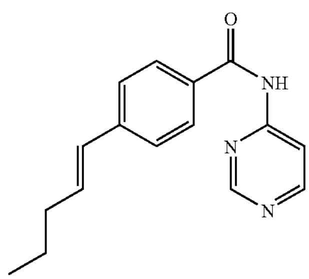 | 267.33 | 268.14 | 2.86 | 2.73 | 3.13 | |
| 254 | 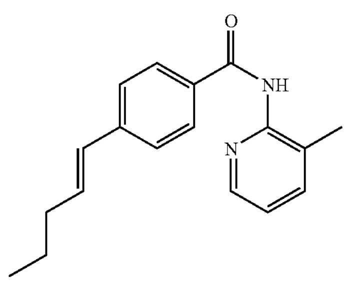 | 280.37 | 281.28 | 2.89 | 2.69 | 2.99 | |
| 255 | 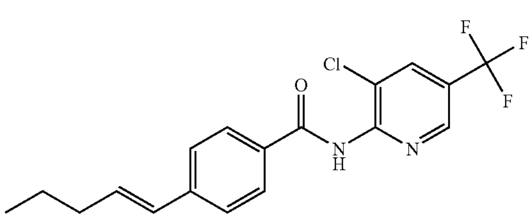 | 368.79 | 369.06 | 4.08 | 3.91 | 4.68 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 256 | 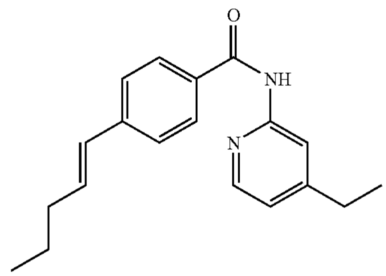 | 294.40 | 295.26 | 3.12 | 2.92 | 3.49 | + |
| 257 | 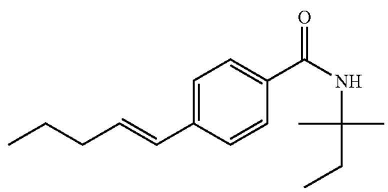 | 259.39 | 260.17 | 4.02 | 3.83 | 4.84 | |
| 258 | 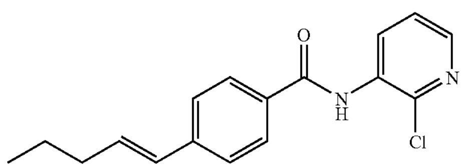 | 300.79 | 301.16 | 3.93 | 3.82 | 4.32 | |
| 259 | 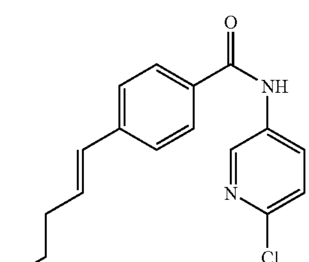 | 300.79 | 301.17 | 3.86 | 3.48 | 4.24 | + |
| 260 | 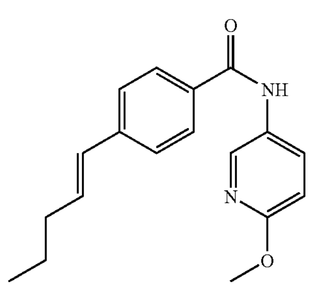 | 296.37 | 297.29 | 3.21 | 3.03 | 3.61 | + |
| 261 | 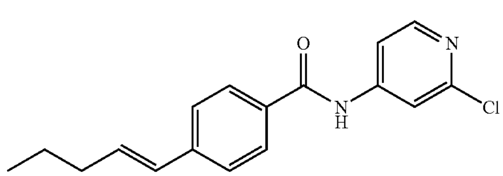 | 300.79 | 301.18 | 3.92 | 3.78 | 4.25 | + |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 262 | 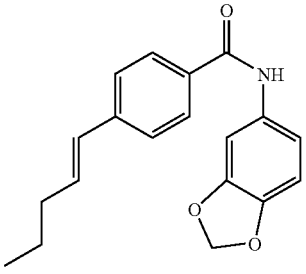 | 309.37 | 310.34 | 3.66 | 3.46 | 4.01 | |
| 263 | 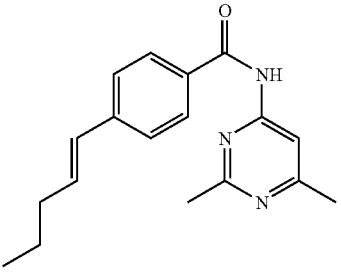 | 295.39 | 296.23 | 2.70 | 2.60 | 2.99 | |
| 264 | 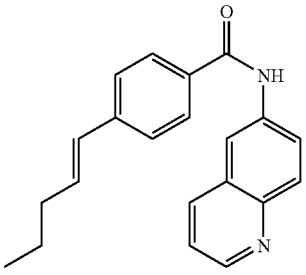 | 316.41 | 317.17 | 2.80 | 2.76 | 3.18 | |
| 265 | 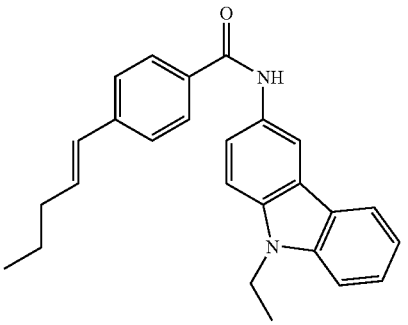 | 382.51 | 383.24 | 3.82 | 3.48 | 3.95 | |
| 266 | 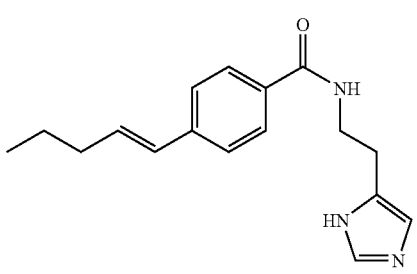 | 283.38 | 284.26 | 2.60 | 2.52 | 3.11 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 267 | 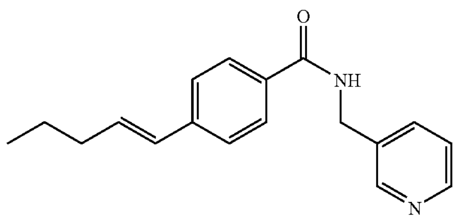 | 280.37 | 281.28 | 2.65 | 2.46 | 3.05 | + |
| 268 | 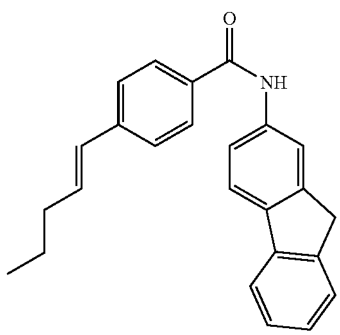 | 353.47 | 354.18 | 4.45 | 4.32 | 4.95 | |
| 269 | 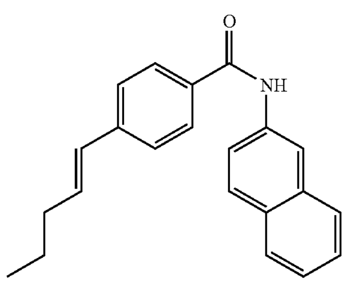 | 315.42 | 316.17 | 4.31 | 4.05 | 4.64 | |
| 270 | 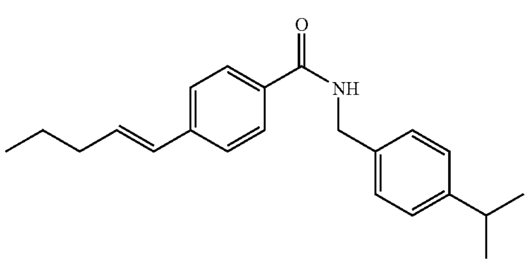 | 321.47 | 322.27 | 4.29 | 4.09 | 4.69 | |
| 271 | 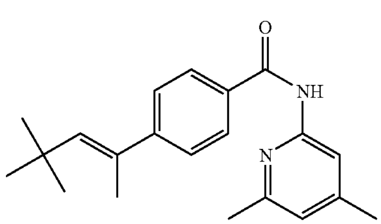 | 322.45 | 323.23 | 3.05 | 2.82 | 3.43 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 272 | 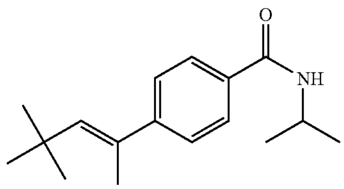 | 259.39 | 260.17 | 3.79 | 3.63 | 4.14 | |
| 273 | 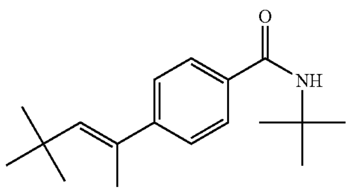 | 273.42 | 274.18 | 4.12 | 4.02 | 4.62 | |
| 274 | 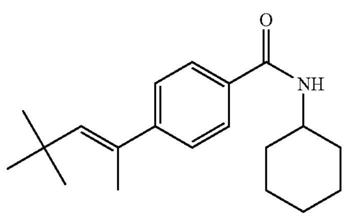 | 299.46 | 300.22 | 4.22 | 4.02 | 4.62 | |
| 275 | 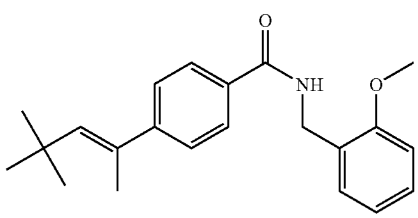 | 337.47 | 338.29 | 3.91 | 3.79 | 4.31 | + |
| 276 | 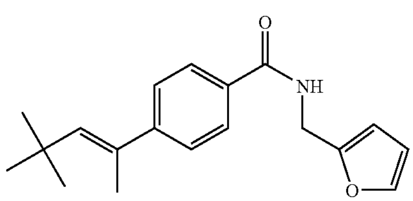 | 297.40 | 298.26 | 3.65 | 3.42 | 4.04 | |
| 277 | 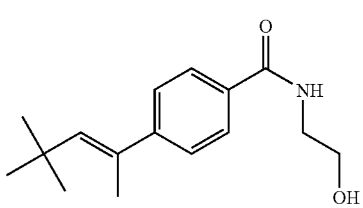 | 261.37 | 262.10 | 3.13 | 3.05 | 3.38 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 278 | 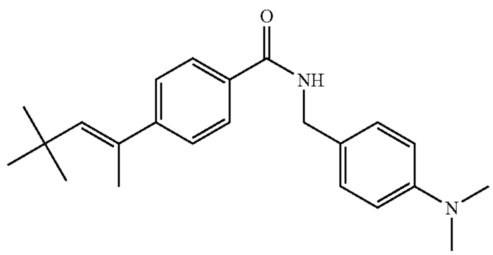 | 350.51 | 351.38 | 2.73 | 2.62 | 3.08 | |
| 279 | 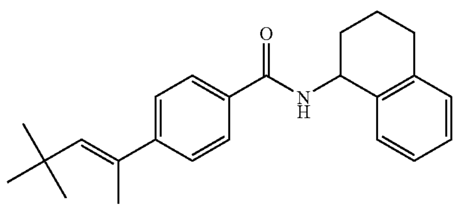 | 347.50 | 348.24 | 4.24 | 4.06 | 4.69 | |
| 280 | 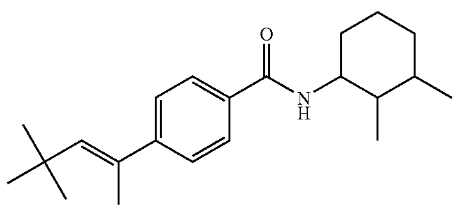 | 327.51 | 328.39 | 4.35 | 4.14 | 5.01 | |
| 281 | 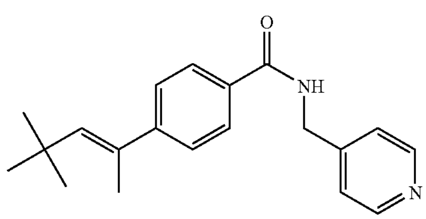 | 308.43 | 309.33 | 2.56 | 2.45 | 2.85 | + |
| 282 | 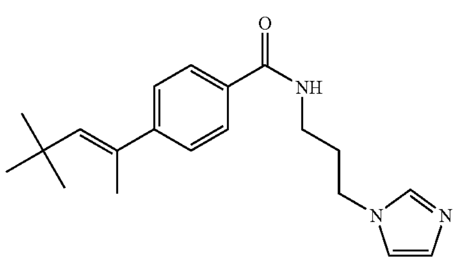 | 325.46 | 326.32 | 2.89 | 2.79 | 3.16 | |
| 283 | 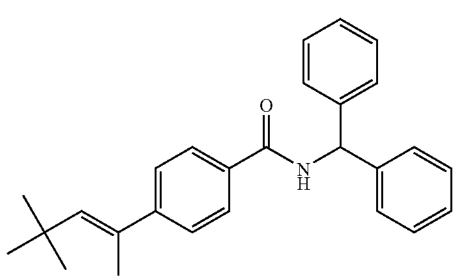 | 383.54 | 384.22 | 4.65 | 4.05 | 4.75 | + |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 284 | 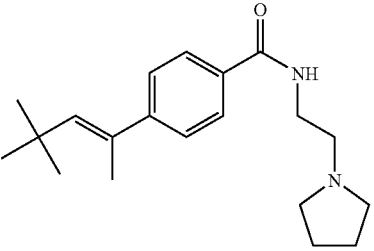 | 314.47 | 315.23 | 2.59 | 2.43 | 2.92 | |
| 285 | 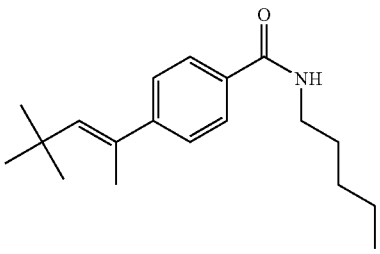 | 287.45 | 288.06 | 3.99 | 3.81 | 4.64 | |
| 286 | 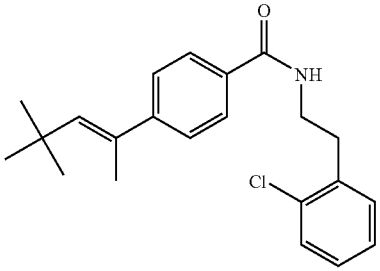 | 355.91 | 356.17 | 4.09 | 3.83 | 4.44 | + |
| 287 | 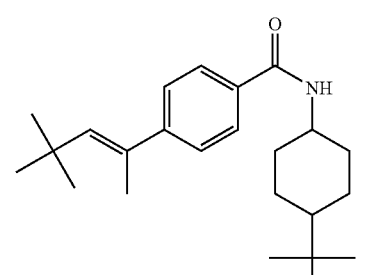 | 355.57 | 356.29 | 4.71 | 4.50 | 5.17 | + |
| 288 | 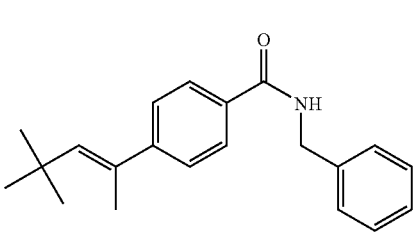 | 307.44 | 308.35 | 3.82 | 3.71 | 4.42 | |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 289 | 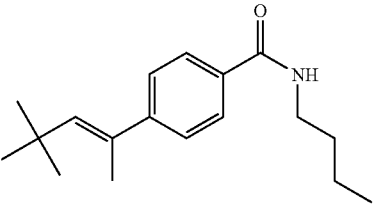 | 273.42 | 274.19 | 3.81 | 3.68 | 4.24 | |
| 290 | 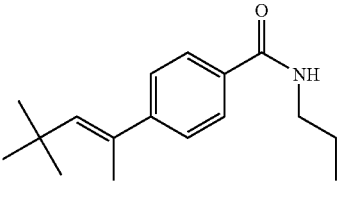 | 259.39 | 260.18 | 3.55 | 3.46 | 4.41 | |
| 291 | 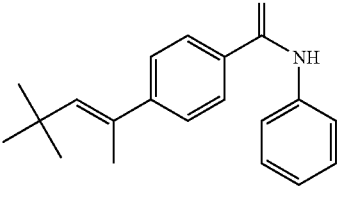 | 293.41 | 294.13 | 3.96 | 3.82 | 4.31 | |
| 292 | 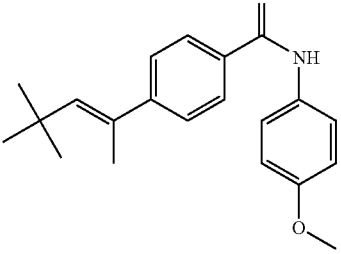 | 323.44 | 324.37 | 3.91 | 3.72 | 4.29 | |
| 293 | 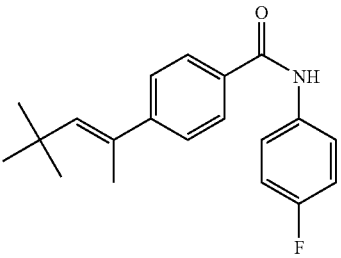 | 311.40 | 312.15 | 4.01 | 3.85 | 4.32 | |
| 294 | 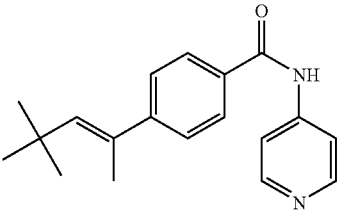 | 294.40 | 295.25 | 2.79 | 2.64 | 3.15 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 295 | 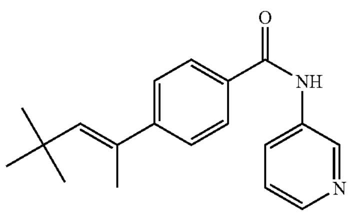 | 294.40 | 295.25 | 2.71 | 2.56 | 3.08 | |
| 296 | 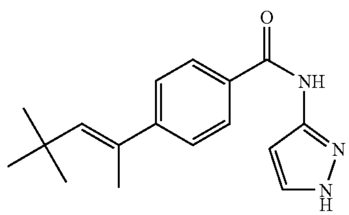 | 283.38 | 284.23 | 3.08 | 2.93 | 3.38 | |
| 297 | 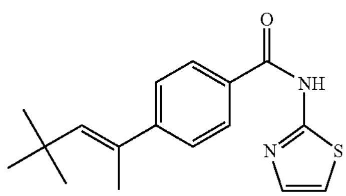 | 300.43 | 301.23 | 3.72 | 3.55 | 3.94 | |
| 298 | 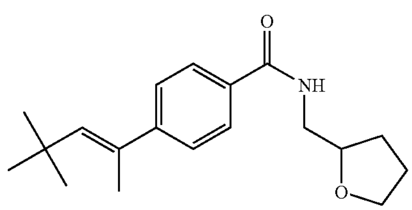 | 301.43 | 302.28 | 3.38 | 3.29 | 3.76 | |
| 299 | 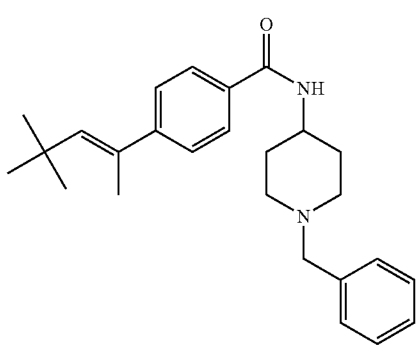 | 390.57 | 391.38 | 2.89 | 2.76 | 3.22 | |
| 300 | 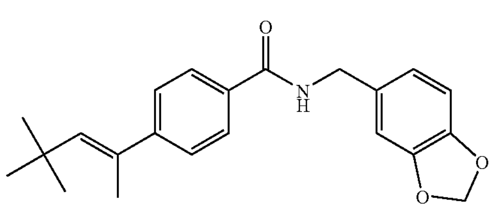 | 351.45 | 352.29 | 3.75 | 3.65 | 4.19 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 301 | 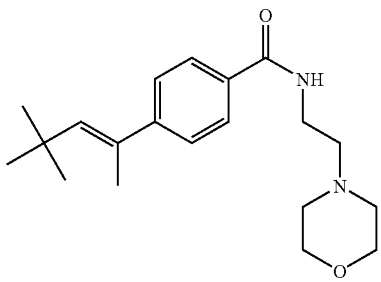 | 330.47 | 331.31 | 2.53 | 2.40 | 2.80 | |
| 302 | 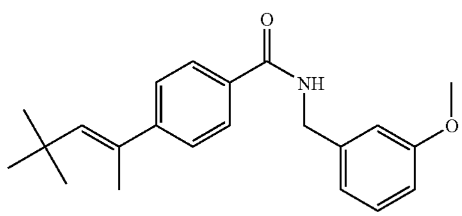 | 337.47 | 338.29 | 3.81 | 3.45 | 4.28 | |
| 303 | 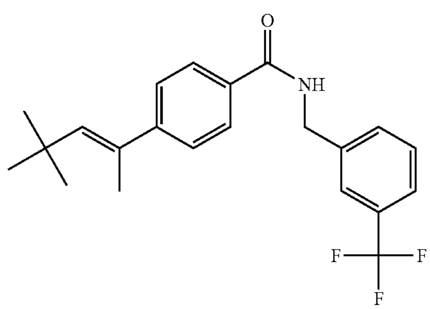 | 375.44 | 376.23 | 4.15 | 3.89 | 4.61 | |
| 304 | 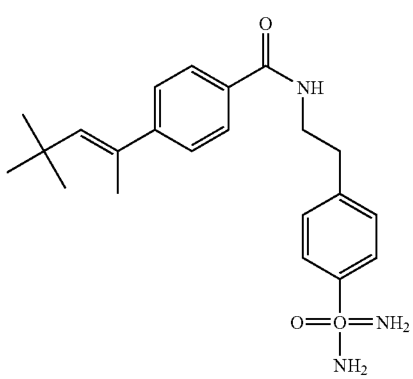 | 400.54 | 401.23 | 3.25 | 3.15 | 3.52 | + |
| 305 | 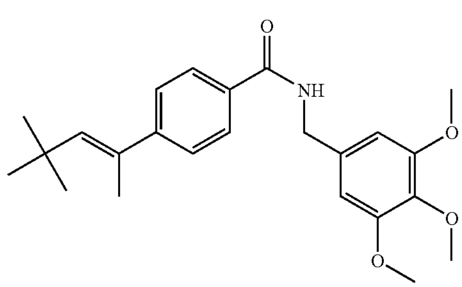 | 397.52 | 398.26 | 3.65 | 3.51 | 3.96 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 306 | 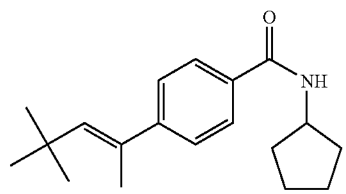 | 285.43 | 286.15 | 3.83 | 3.63 | 4.26 | |
| 307 | 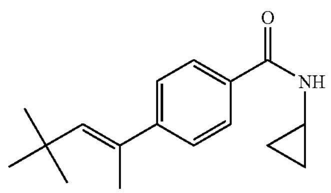 | 257.38 | 258.26 | 3.36 | 3.22 | 4.06 | |
| 308 | 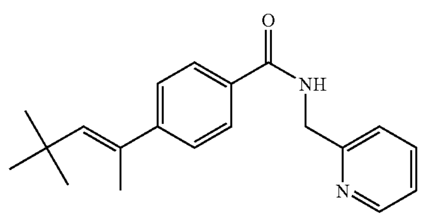 | 308.43 | 309.33 | 2.58 | 2.38 | 2.96 | + |
| 309 | 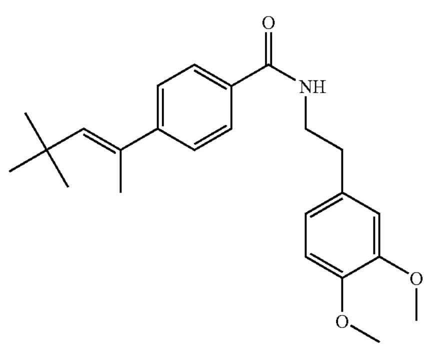 | 381.52 | 382.26 | 3.63 | 3.43 | 4.06 | |
| 310 | 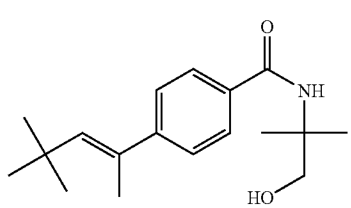 | 289.42 | 290.21 | 3.32 | 3.24 | 3.59 | |
| 311 | 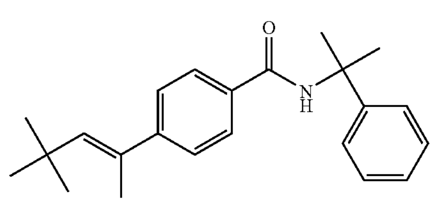 | 335.49 | 336.47 | 4.14 | 3.89 | 4.52 | |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 312 | 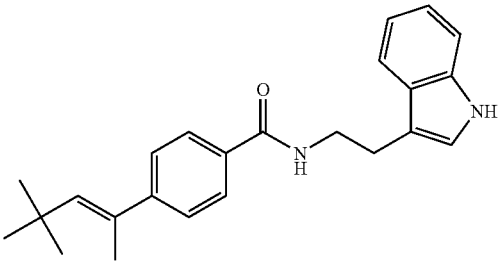 | 360.50 | 361.34 | 3.79 | 3.66 | 4.35 | |
| 313 | 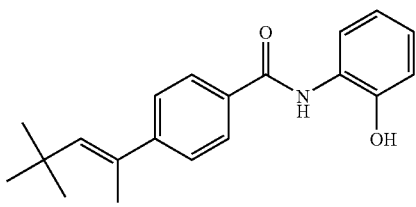 | 309.41 | 310.37 | 3.81 | 3.49 | 4.11 | + |
| 314 | 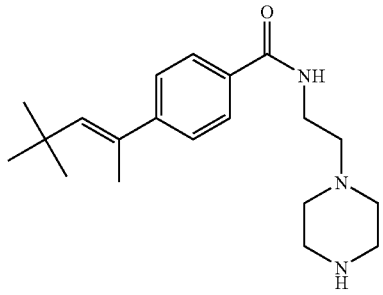 | 329.49 | 330.28 | 2.19 | 2.13 | 2.48 | |
| 315 | 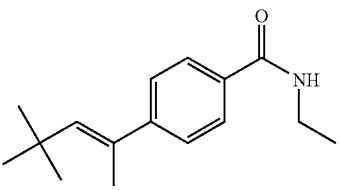 | 245.37 | 246.22 | 3.36 | 3.26 | 3.72 | + |
| 316 | 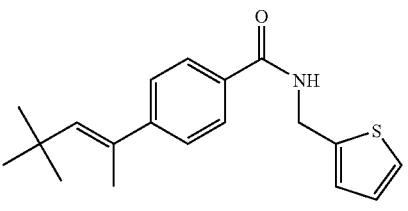 | 313.47 | 314.10 | 3.78 | 3.68 | 4.12 | ++ |
| 317 | 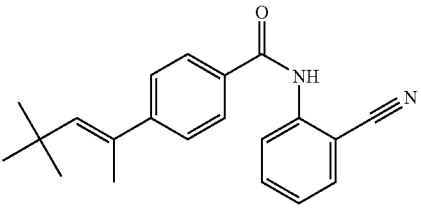 | 318.42 | 319.05 | 3.78 | 3.71 | 4.18 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 318 | 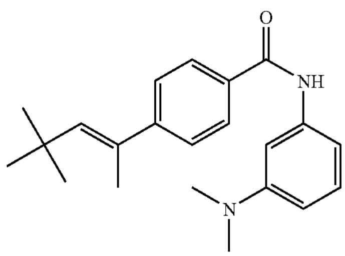 | 336.48 | 337.40 | 2.92 | 2.75 | 3.29 | |
| 319 | 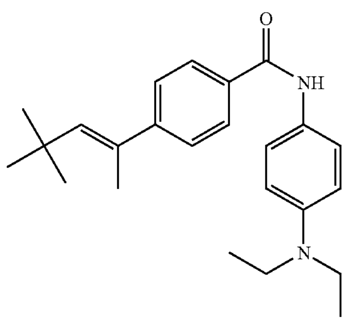 | 364.54 | 365.28 | 3.02 | 2.63 | 3.32 | |
| 320 | 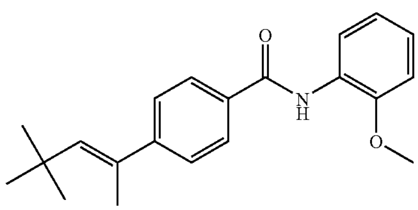 | 323.44 | 324.38 | 4.29 | 4.06 | 4.69 | |
| 321 | 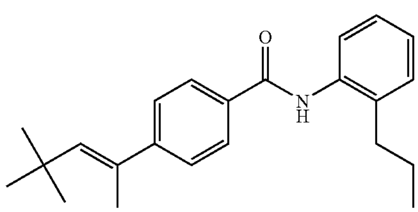 | 335.49 | 336.48 | 4.25 | 4.02 | 4.75 | |
| 322 | 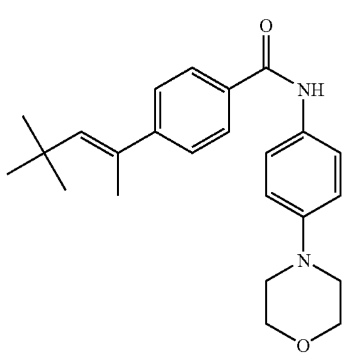 | 378.52 | 379.35 | 3.16 | 3.02 | 3.45 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 323 | 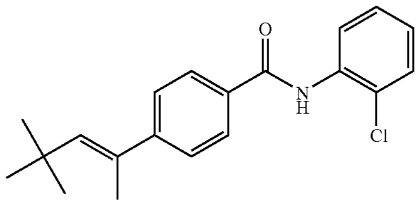 | 327.86 | 328.28 | 4.35 | 4.18 | 4.67 | |
| 324 | 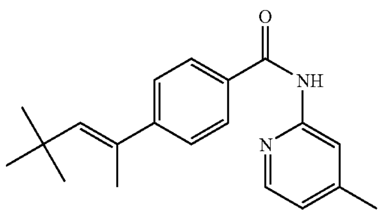 | 308.43 | 309.33 | 2.89 | 2.72 | 3.24 | + |
| 325 | 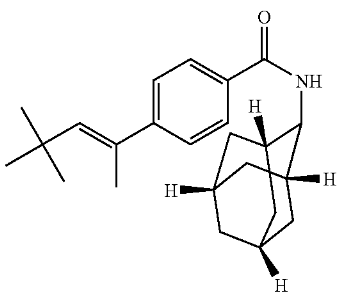 | 351.54 | 352.39 | 4.61 | 4.32 | 5.07 | |
| 326 | 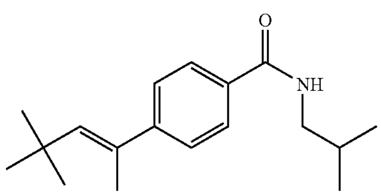 | 273.42 | 274.17 | 3.81 | 3.68 | 4.15 | |
| 327 | 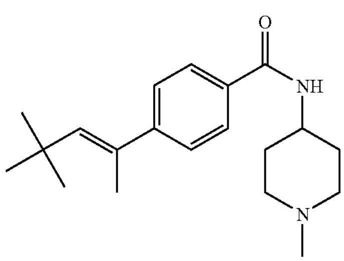 | 314.47 | 315.21 | 2.54 | 2.39 | 2.78 | |
| 328 | 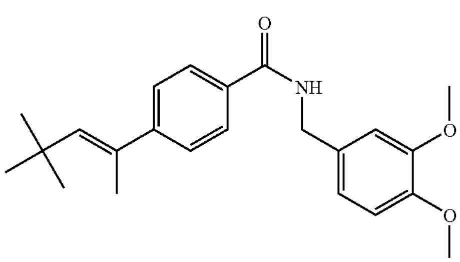 | 367.49 | 368.21 | 3.59 | 3.51 | 3.91 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 329 | 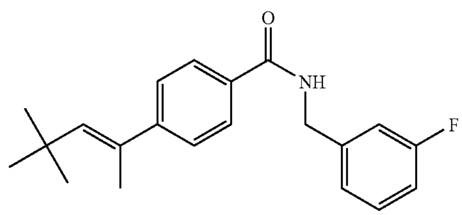 | 325.43 | 326.28 | 3.89 | 3.72 | 4.28 | |
| 330 | 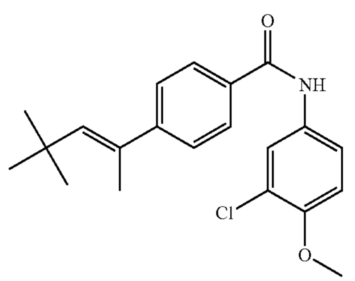 | 357.88 | 358.17 | 4.11 | 3.96 | 4.55 | + |
| 331 | 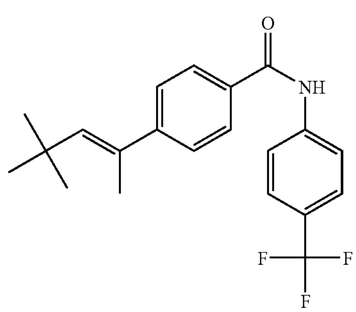 | 361.41 | 362.30 | 4.41 | 4.21 | 4.66 | +++ |
| 332 | 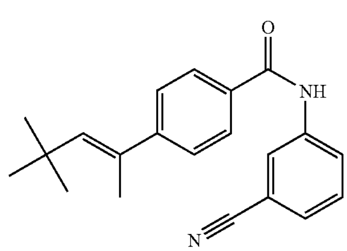 | 318.42 | 319.02 | 4.01 | 3.86 | 4.29 | +++ |
| 333 | 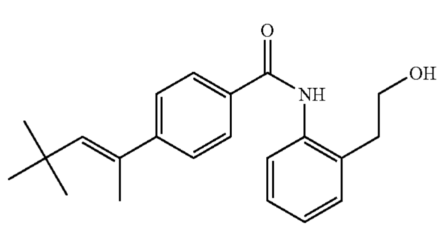 | 337.47 | 338.29 | 3.63 | 3.45 | 3.99 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 334 | 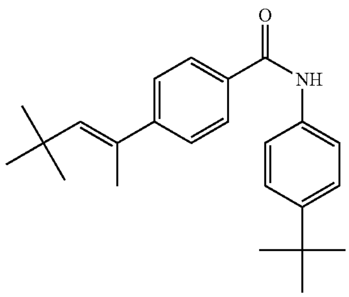 | 349.52 | 350.44 | 4.54 | 4.38 | 4.95 | +++ |
| 335 | 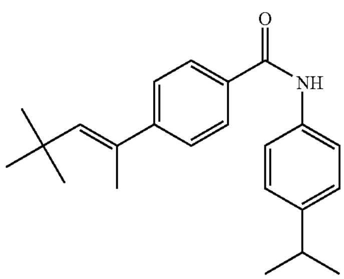 | 335.49 | 336.48 | 4.48 | 4.26 | 4.91 | |
| 336 | 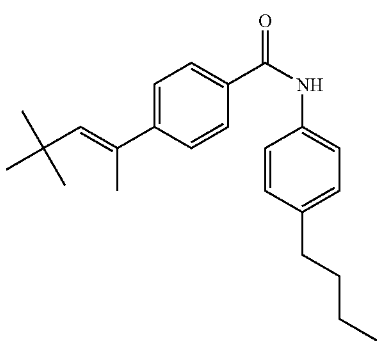 | 349.52 | 350.44 | 4.69 | 4.54 | 5.07 | ++ |
| 337 | 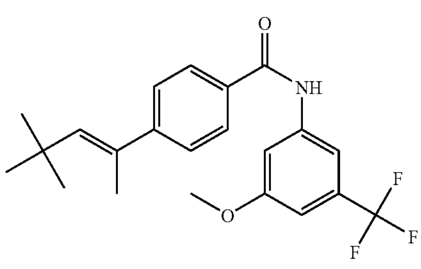 | 391.44 | 392.21 | 4.45 | 4.29 | 4.78 | + |
| 338 | 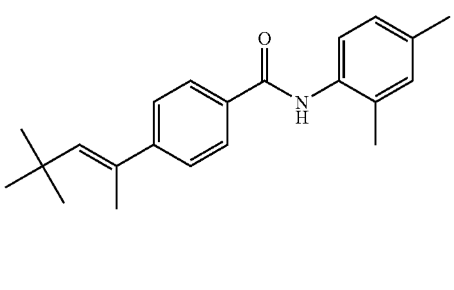 | 321.47 | 322.28 | 4.11 | 3.92 | 4.59 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 339 | 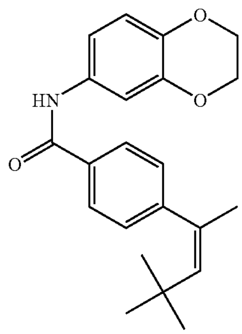 | 351.45 | 352.28 | 3.91 | 3.69 | 4.44 | |
| 340 | 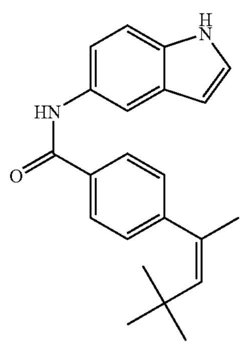 | 332.45 | 333.28 | 3.72 | 3.61 | 4.02 | |
| 341 | 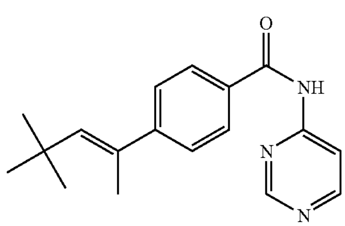 | 295.39 | 296.26 | 3.15 | 3.05 | 3.48 | + |
| 342 | 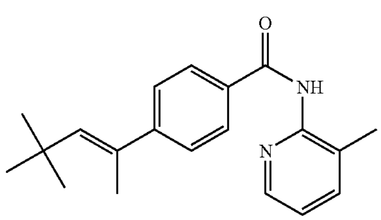 | 308.43 | 309.31 | 2.85 | 2.66 | 3.06 | |
| 343 | 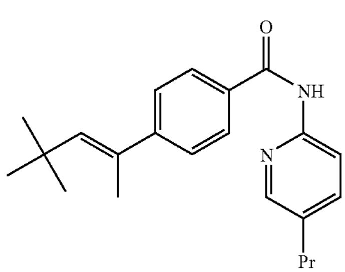 | 373.30 | 375.06 | 4.32 | 3.96 | 4.74 | |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 344 | 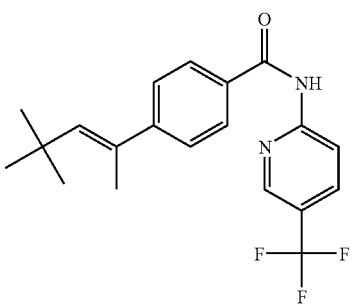 | 362.40 | 363.35 | 4.39 | 4.18 | 4.64 | + |
| 345 | 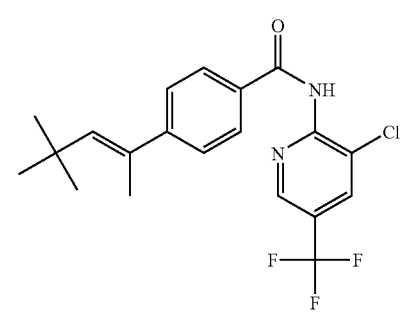 | 396.84 | 397.12 | 4.10 | 3.94 | 4.45 | + |
| 346 | 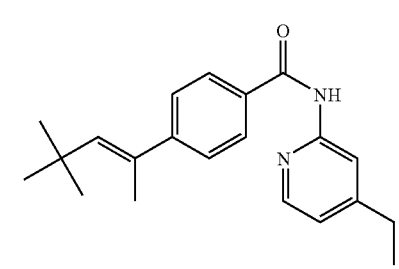 | 322.45 | 323.22 | 3.05 | 2.86 | 3.32 | |
| 347 | 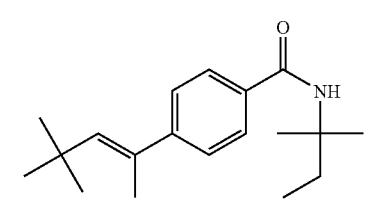 | 287.45 | 288.05 | 4.12 | 3.88 | 4.55 | |
| 348 | 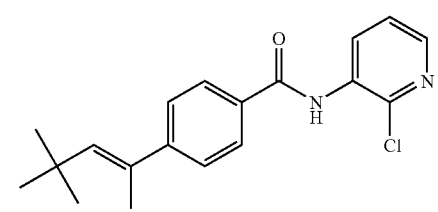 | 328.85 | 329.25 | 3.95 | 3.88 | 4.25 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 349 | 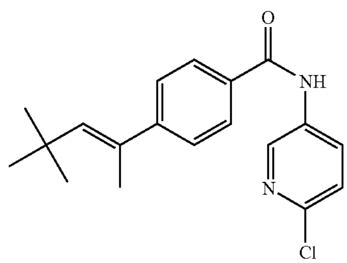 | 328.85 | 329.24 | 3.88 | 3.69 | 4.58 | |
| 350 | 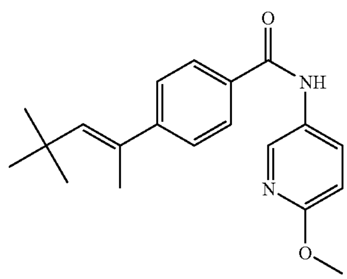 | 324.43 | 325.32 | 3.51 | 3.23 | 3.79 | |
| 351 | 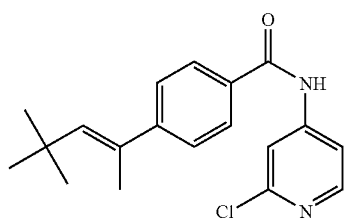 | 328.85 | 329.24 | 3.92 | 3.79 | 4.25 | + |
| 352 | 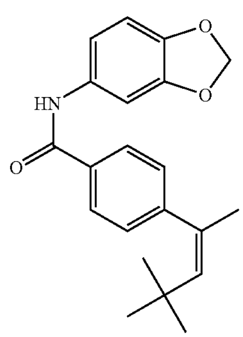 | 337.42 | 338.29 | 3.88 | 3.62 | 4.26 | |
| 353 | 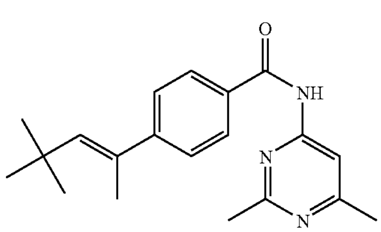 | 323.44 | 324.39 | 2.95 | 2.86 | 3.11 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 354 | 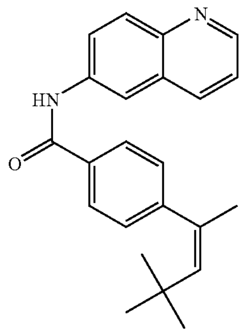 | 344.46 | 345.09 | 2.92 | 2.62 | 3.28 | |
| 355 | 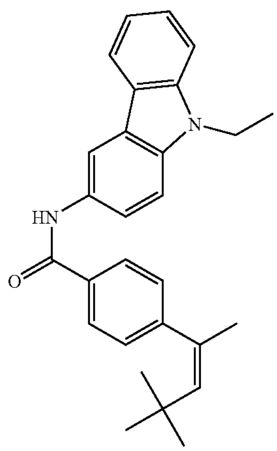 | 410.56 | 411.28 | 4.48 | 4.21 | 4.92 | |
| 356 | 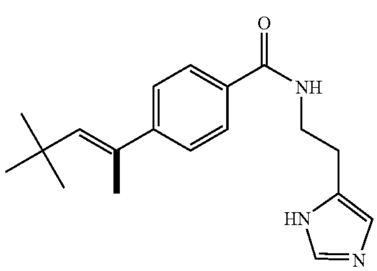 | 311.43 | 312.18 | 2.52 | 2.39 | 2.88 | + |
| 357 | 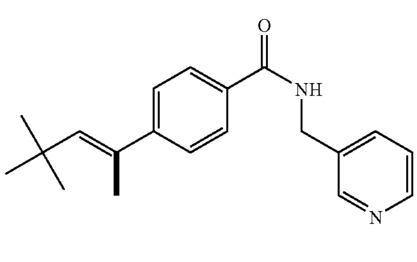 | 308.43 | 309.32 | 2.55 | 2.42 | 2.85 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 358 | 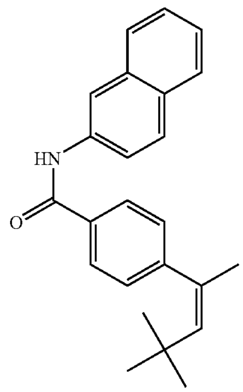 | 343.47 | 344.18 | 4.36 | 4.06 | 4.66 | ++++ |
| 359 | 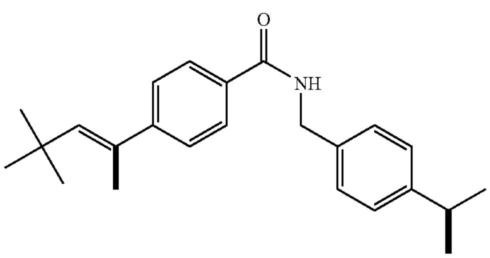 | 349.52 | 350.45 | 4.36 | 4.14 | 4.75 | |
| 360 | 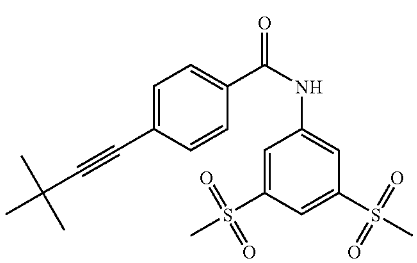 | 433.55 | 437.92 | 3.49 | 3.43 | 3.61 | |
| 361 | 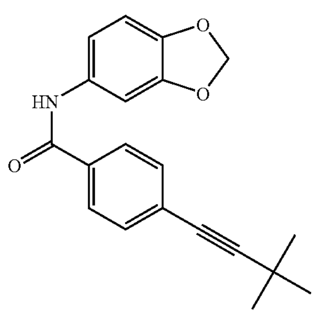 | 321.38 | 322.26 | 3.78 | 3.45 | 4.22 | ++++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 362 | 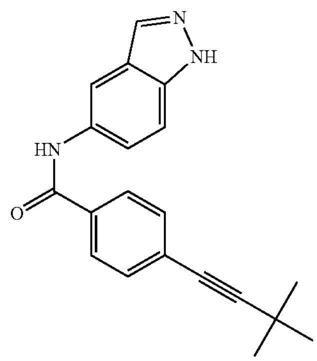 | 317.39 | 318.16 | 3.35 | 3.19 | 3.61 | |
| 363 | 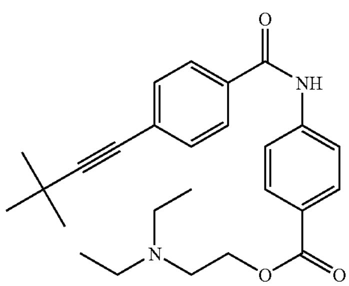 | 420.56 | 421.28 | 3.14 | 3.09 | 3.51 | +++ |
| 364 | 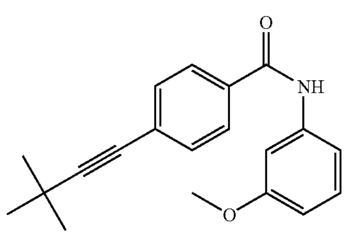 | 307.40 | 308.37 | 3.92 | 3.78 | 4.16 | ++++ |
| 365 | 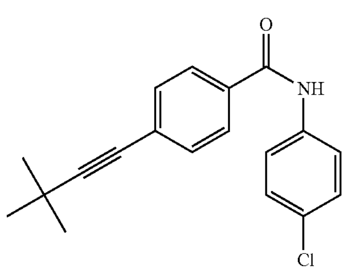 | 311.81 | 309.08 | 3.76 | 3.73 | 3.88 | + |
| 366 | 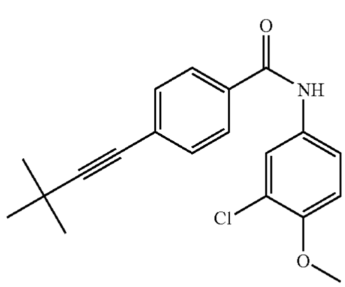 | 341.84 | 342.18 | 3.99 | 3.93 | 4.38 | ++ |

TABLE 1-continued
AMIDE COMPOUNDS
| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 367 | 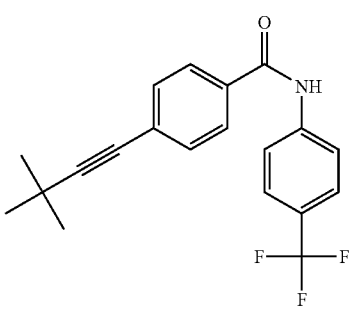 | 345.37 | 346.23 | 4.21 | 3.92 | 4.52 | ++ |
| 368 | 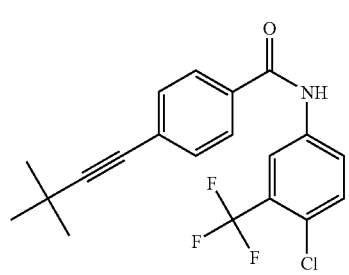 | 379.81 | 380.22 | 4.41 | 4.26 | 4.52 | ++++ |
| 369 | 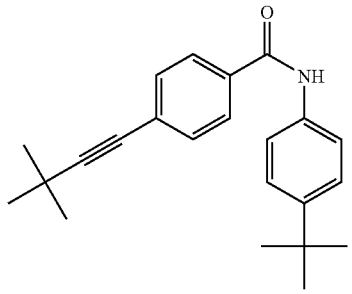 | 333.48 | 334.42 | 4.36 | 4.11 | 4.67 | |
| 370 | 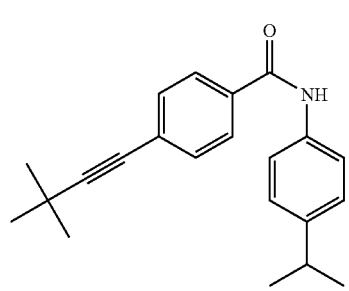 | 319.45 | 320.28 | 4.26 | 4.02 | 4.48 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 371 | 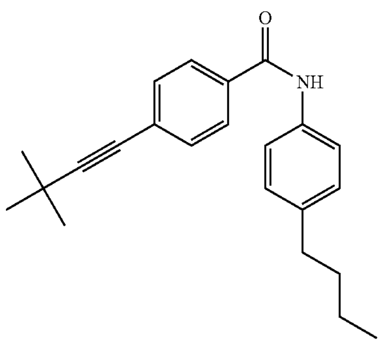 | 333.48 | 334.41 | 4.45 | 4.39 | 4.74 | |
| 372 | 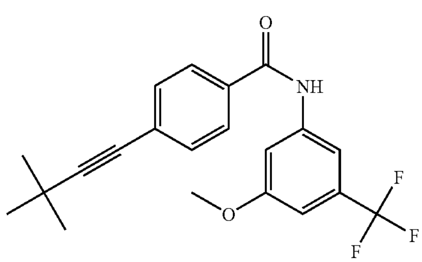 | 375.39 | 376.29 | 4.25 | 4.09 | 4.41 | ++++ |
| 373 | 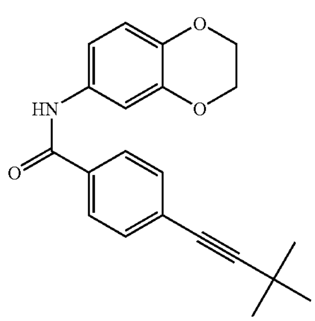 | 335.41 | 336.44 | 3.76 | 3.55 | 3.99 | ++++ |
| 374 | 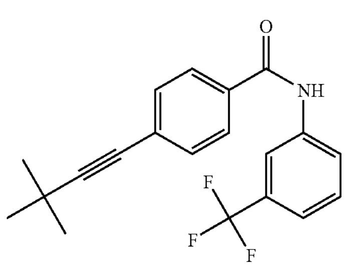 | 345.37 | 346.22 | 4.20 | 4.15 | 4.41 | ++++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 375 | 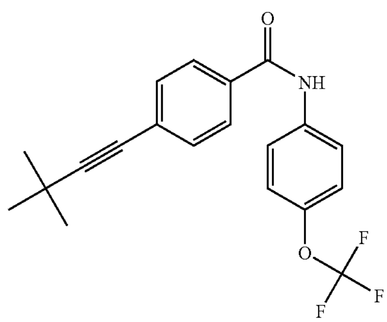 | 361.37 | 362.31 | 4.21 | 4.05 | 4.49 | |
| 376 | 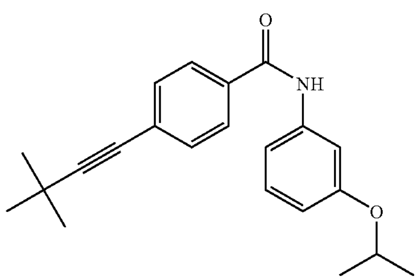 | 335.45 | 336.47 | 4.14 | 3.95 | 4.55 | +++ |
| 377 | 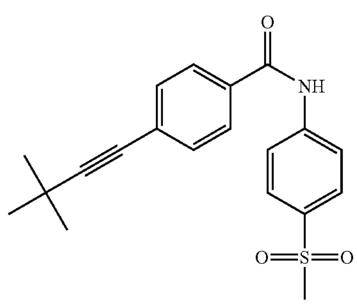 | 355.46 | 356.25 | 3.56 | 3.43 | 3.82 | ++++ |
| 378 | 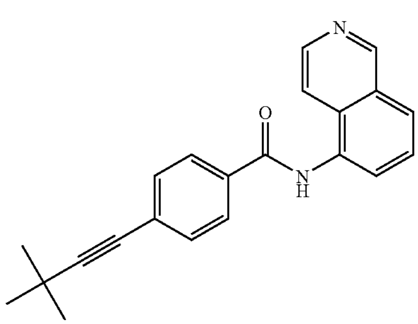 | 328.42 | 329.30 | 2.77 | 2.61 | 3.05 | ++++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 379 | 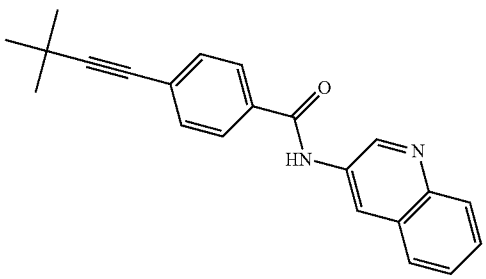 | 328.42 | 329.29 | 3.12 | 2.94 | 3.51 | ++++ |
| 380 | 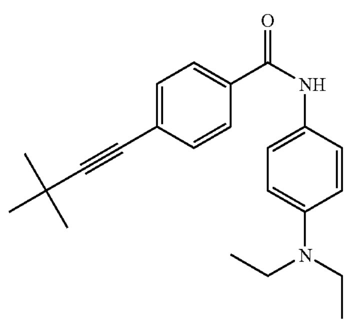 | 348.49 | 349.37 | 3.00 | 2.93 | 3.43 | ++ |
| 381 | 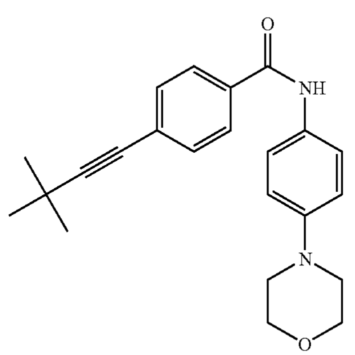 | 362.48 | 363.49 | 3.12 | 2.98 | 3.45 | |
| 382 | 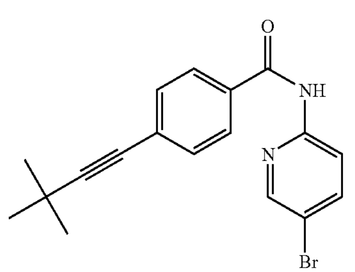 | 357.25 | 357.09 | 4.15 | 4.01 | 4.32 | ++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 383 | 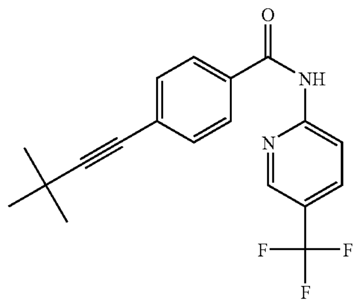 | 346.36 | 347.14 | 4.21 | 4.09 | 4.34 | +++ |
| 384 | 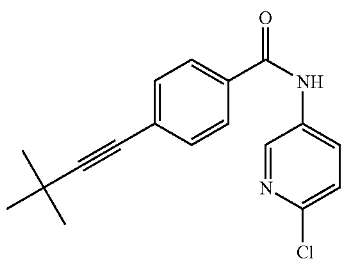 | 312.80 | 313.12 | 3.76 | 3.61 | 3.99 | ++++ |
| 385 | 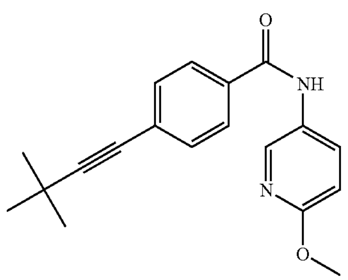 | 308.38 | 309.38 | 3.47 | 3.34 | 3.71 | ++++ |
| 386 | 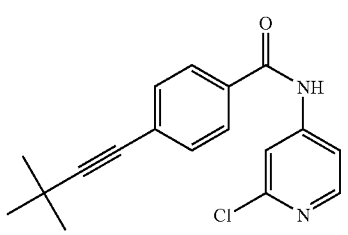 | 312.80 | 313.15 | 3.82 | 3.62 | 4.06 | |
| 387 | 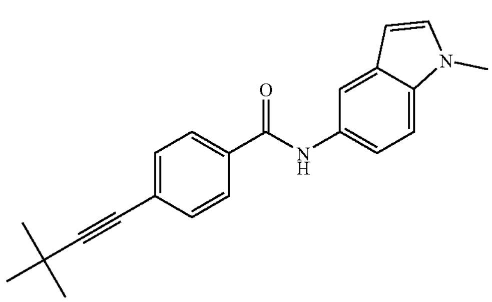 | 330.43 | 331.29 | 3.83 | 3.61 | 4.25 | ++++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 388 | 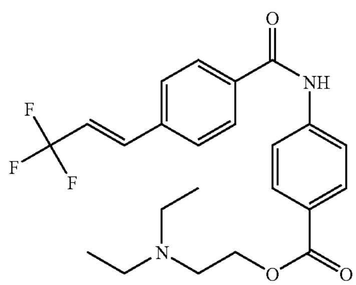 | 434.46 | 435.36 | 2.96 | 2.92 | 3.11 | |
| 389 | 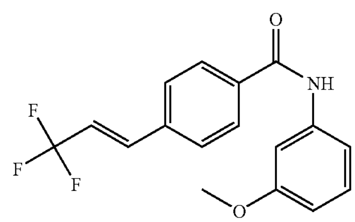 | 321.30 | 322.27 | 3.46 | 3.38 | 3.66 | ++++ |
| 390 | 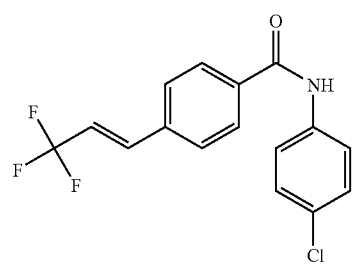 | 325.72 | 326.25 | 3.73 | 3.63 | 3.85 | ++ |
| 391 | 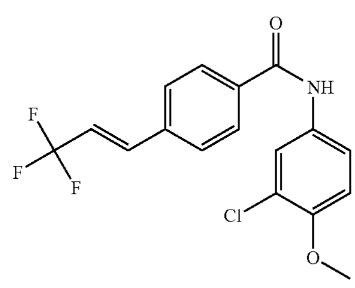 | 355.75 | 356.17 | 3.59 | 3.42 | 3.95 | + |
| 392 | 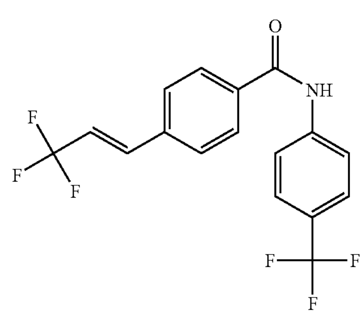 | 359.27 | 360.06 | 5.14 | 5.00 | 5.22 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 393 | 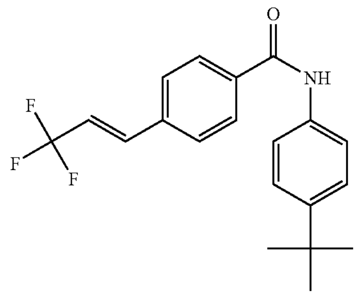 | 347.38 | 348.29 | 4.24 | 4.19 | 4.44 | |
| 394 | 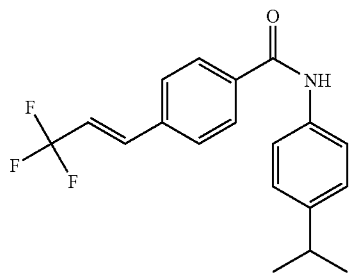 | 333.36 | 334.28 | 3.92 | 3.82 | 4.22 | ++ |
| 395 | 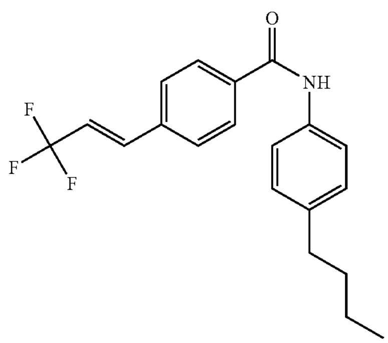 | 347.38 | 348.29 | 4.14 | 4.05 | 4.31 | + |
| 396 | 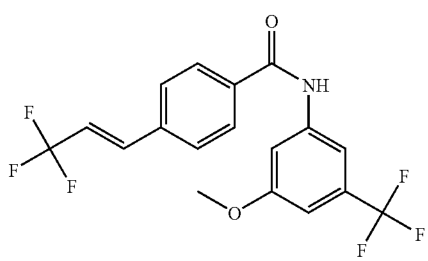 | 389.30 | 390.30 | 3.96 | 3.81 | 4.02 | |
| 397 | 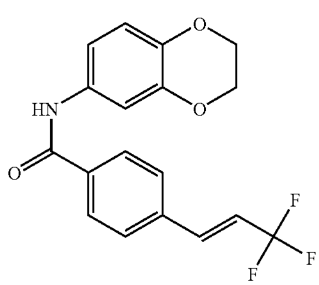 | 349.31 | 350.29 | 3.35 | 3.26 | 3.56 | +++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 398 | 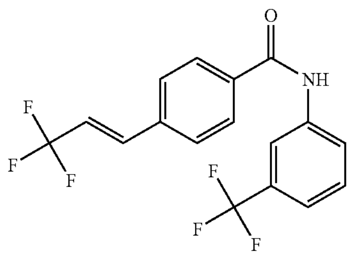 | 359.27 | 360.14 | 3.84 | 3.67 | 3.97 | ++++ |
| 399 | 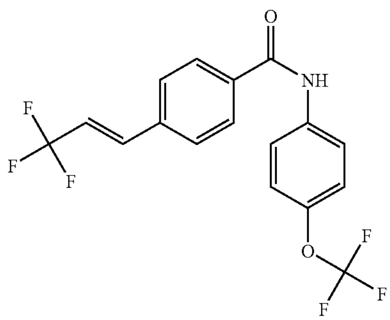 | 375.27 | 376.16 | 3.88 | 3.79 | 4.28 | ++++ |
| 400 | 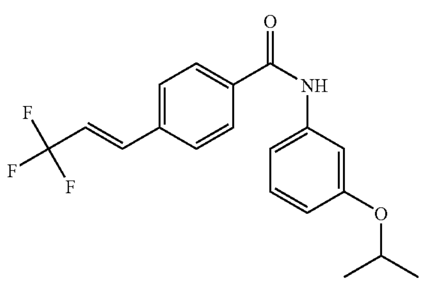 | 349.36 | 350.33 | 3.76 | 3.62 | 3.96 | |
| 401 | 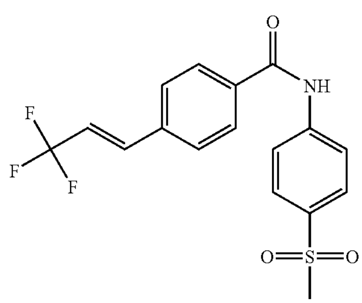 | 369.37 | 371.10 | 1.56 | 1.49 | 1.70 | |
| 402 | 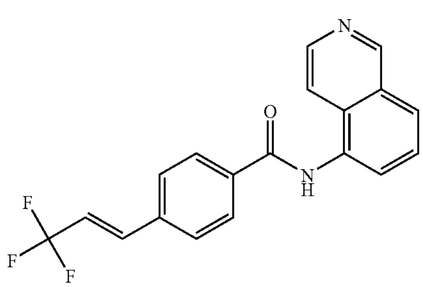 | 342.32 | 343.09 | 2.48 | 2.45 | 2.55 | |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 403 | 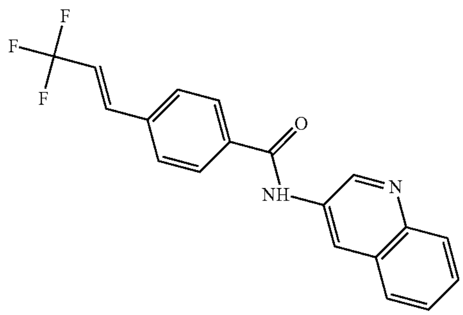 | 342.32 | 343.10 | 2.78 | 2.59 | 2.85 | |
| 404 | 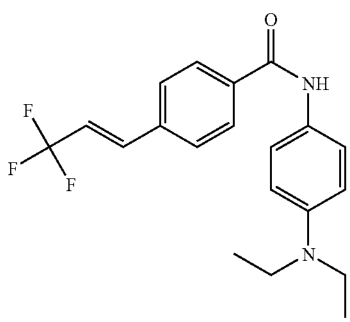 | 362.40 | 363.43 | 2.72 | 2.50 | 3.11 | |
| 405 | 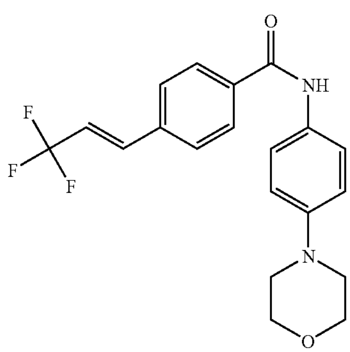 | 376.38 | 377.34 | 2.86 | 2.82 | 3.15 | |
| 406 | 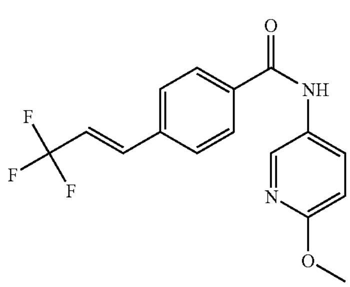 | 322.29 | 323.16 | 3.04 | 2.85 | 3.09 | ++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 407 | 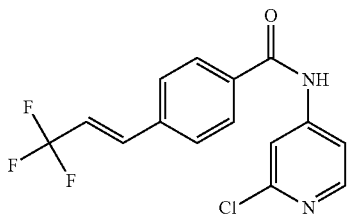 | 326.71 | 327.08 | 3.46 | 3.39 | 3.58 | |
| 408 | 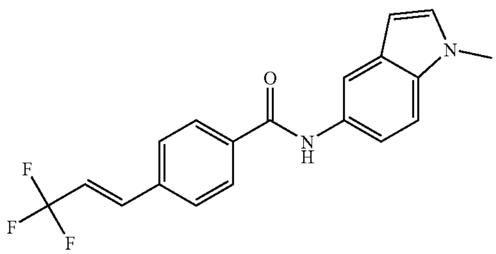 | 344.34 | 345.09 | 3.43 | 3.18 | 3.72 | |
| 409 | 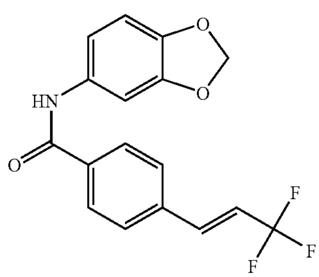 | 335.29 | 336.39 | 3.34 | 3.25 | 3.44 | |
| 410 | 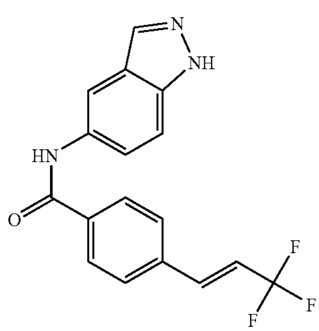 | 331.30 | 332.28 | 3.06 | 3.00 | 3.25 | |
| 411 | 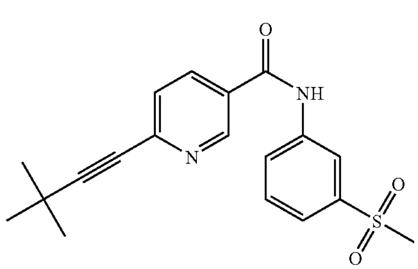 | 356.45 | 357.11 | 3.05 | 2.98 | 3.62 | ++++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 412 | 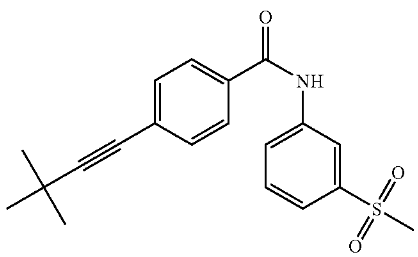 | 355.46 | 356.25 | 4.32 | 3.74 | 4.75 | ++++ |
| 413 | 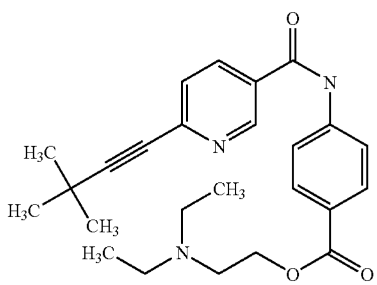 | 421.54 | 422.12 | 2.68 | 2.62 | 3.05 | + |
| 414 | 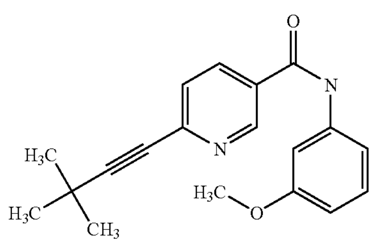 | 308.38 | 309.35 | 3.32 | 3.26 | 3.68 | ++++ |
| 415 | 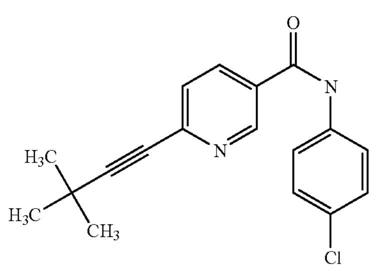 | 312.80 | 313.11 | 3.59 | 3.43 | 3.91 | |
| 416 | 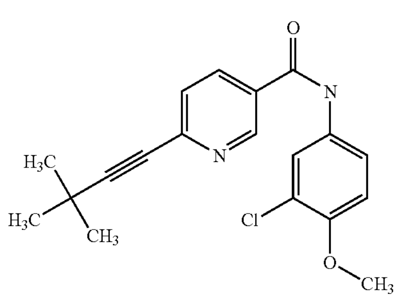 | 342.83 | 343.15 | 3.48 | 3.39 | 3.72 | ++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 417 | 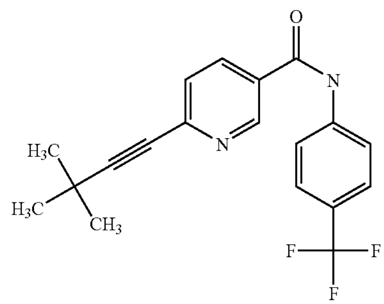 | 346.36 | 347.17 | 3.76 | 3.65 | 4.04 | ++++ |
| 418 | 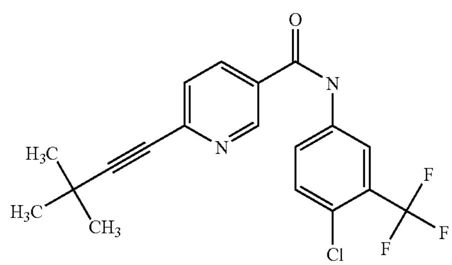 | 380.80 | 381.24 | 3.96 | 3.88 | 4.31 | ++++ |
| 419 | 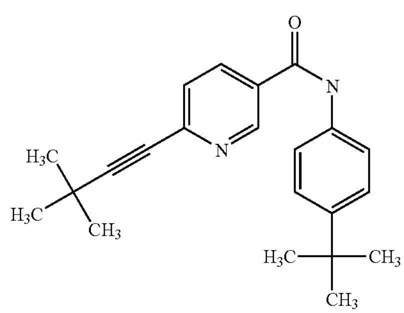 | 334.47 | 335.39 | 3.89 | 3.82 | 4.21 | ++++ |
| 420 | 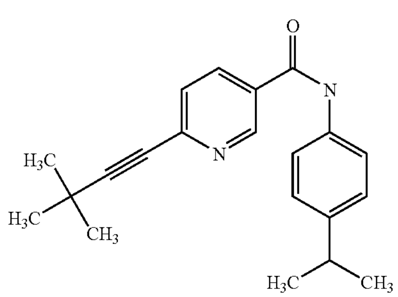 | 320.44 | 321.28 | 3.78 | 3.32 | 4.18 | +++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 421 | 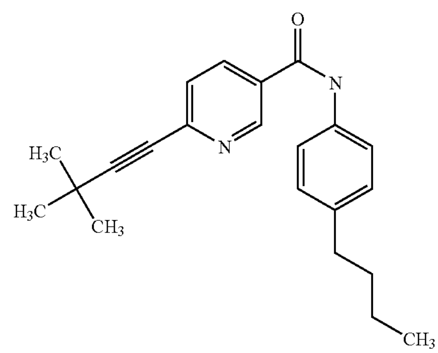 | 334.47 | 335.41 | 4.01 | 3.93 | 4.31 | ++ |
| 422 | 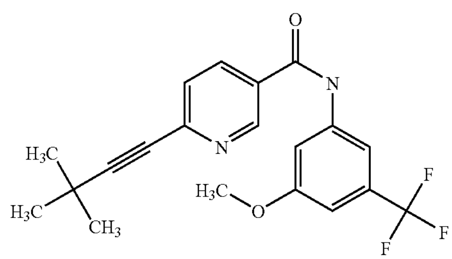 | 376.38 | 377.32 | 3.82 | 3.74 | 4.18 | ++++ |
| 423 | 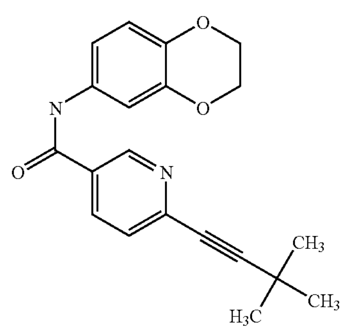 | 336.39 | 337.39 | 3.21 | 3.00 | 3.43 | ++++ |
| 424 | 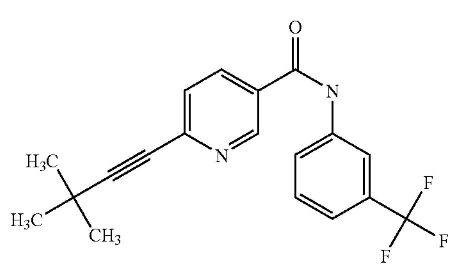 | 346.36 | 347.16 | 3.75 | 3.51 | 4.02 | +++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 425 | 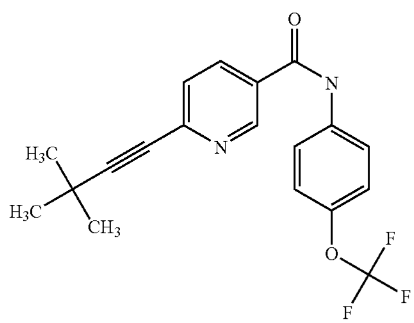 | 362.35 | 363.35 | 3.76 | 3.66 | 4.02 | + |
| 426 | 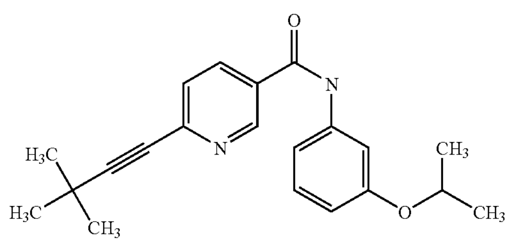 | 336.44 | 337.43 | 3.64 | 3.46 | 3.91 | |
| 427 | 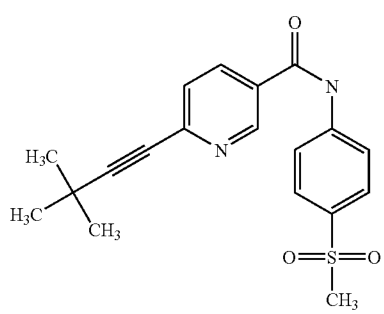 | 356.45 | 357.09 | 3.03 | 2.98 | 3.26 | ++ |
| 428 | 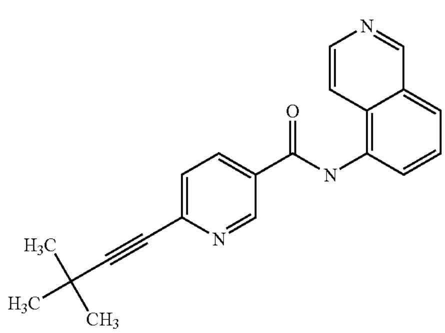 | 329.41 | 330.27 | 2.38 | 2.23 | 2.62 | ++++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 429 | 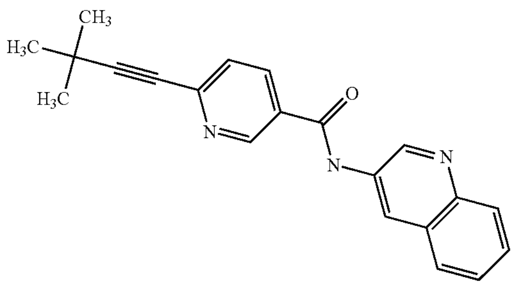 | 329.41 | 330.26 | 2.70 | 2.63 | 2.99 | ++++ |
| 430 | 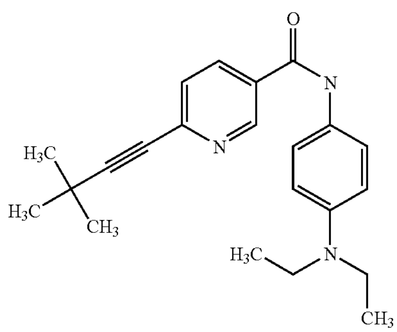 | 349.48 | 350.44 | 2.58 | 2.42 | 2.98 | + |
| 431 | 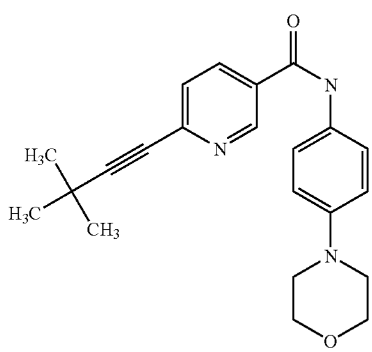 | 363.46 | 364.39 | 2.66 | 2.59 | 2.95 | |
| 432 | 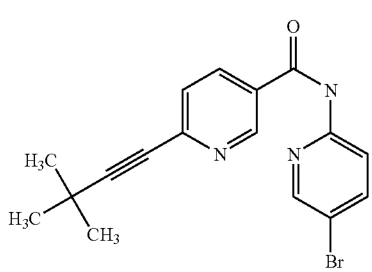 | 358.24 | 358.12 | 3.55 | 3.48 | 3.71 | + |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 433 | 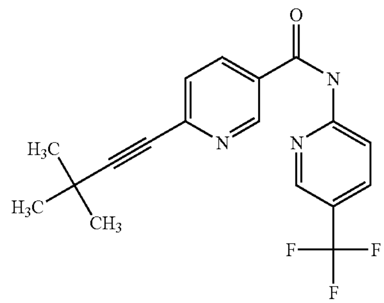 | 347.34 | 348.22 | 3.66 | 3.59 | 3.91 | ++ |
| 434 | 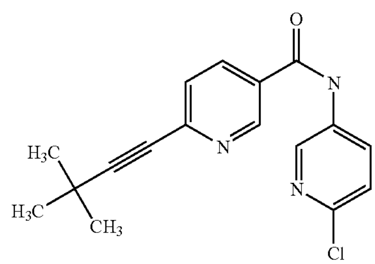 | 313.79 | 314.12 | 3.22 | 3.12 | 3.49 | + |
| 435 | 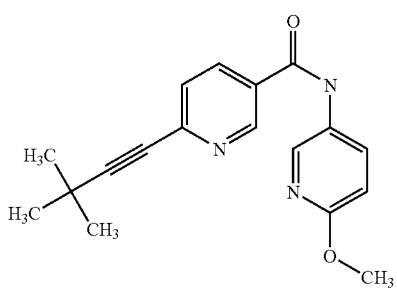 | 309.37 | 310.39 | 2.92 | 2.79 | 3.15 | + |
| 436 | 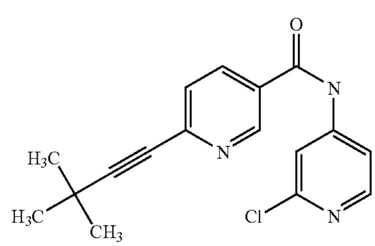 | 313.79 | 314.13 | 3.26 | 3.16 | 3.39 | |
| 437 | 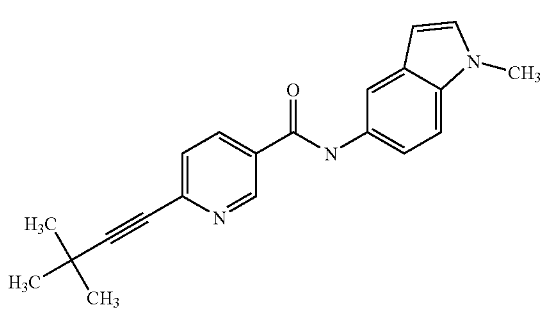 | 331.42 | 332.28 | 3.29 | 3.03 | 3.51 | ++++ |

TABLE 1-continued

AMIDE COMPOUNDS

| ID | STRUCTURE | MW (calc) | MS (Obs) | HPLC RT (Min) | HPLC START TIME (Min) | HPLC END TIME (Min) | % Inhibition @ 1 uM |
|---|---|---|---|---|---|---|---|
| 438 | 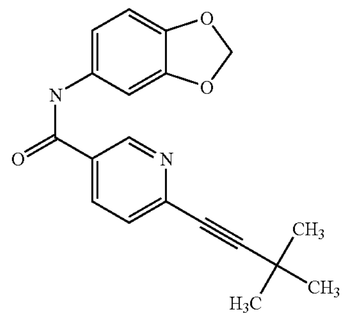 | 322.37 | 323.19 | 3.22 | 3.11 | 3.45 | ++++ |
| 439 | 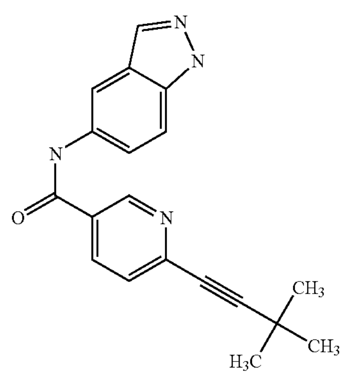 | 318.38 | 319.08 | 2.89 | 2.85 | 3.16 | |
| 440 | 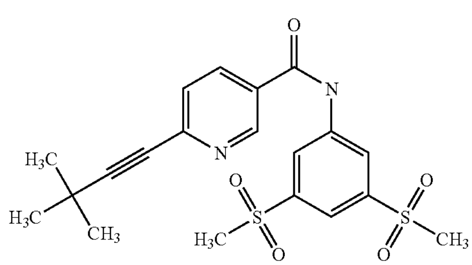 | 434.54 | 435.15 | 3.03 | 2.93 | 3.16 | |

In addition to the amide compounds listed in Table I above, the following recited below, which comprise vinyl- and ethynyl-substituted amides of this wherein $R^1$ and $R^{2'}$ are as described before, can be prepared using the procedure above for Example 1 or 2 and the corresponding benzoic acids, appropriate and purification methods known to those skilled in the art.

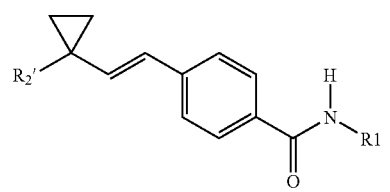

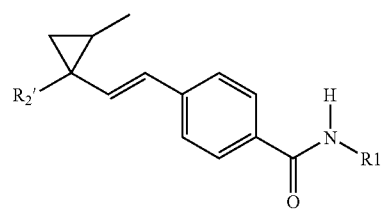

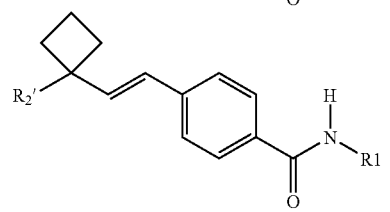

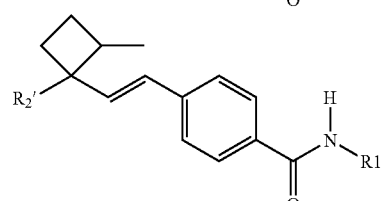

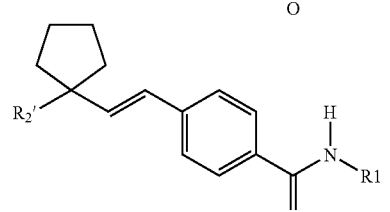

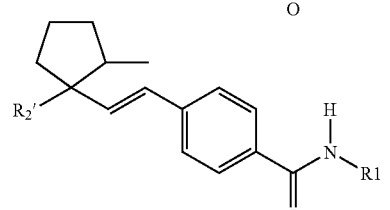

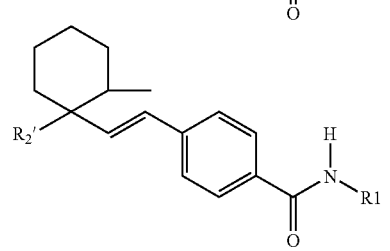

-continued

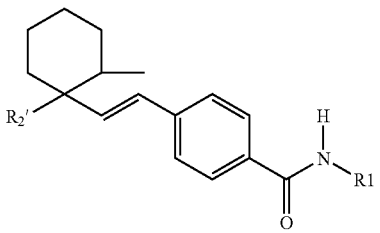

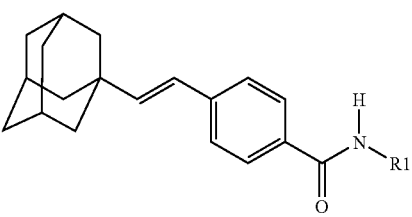

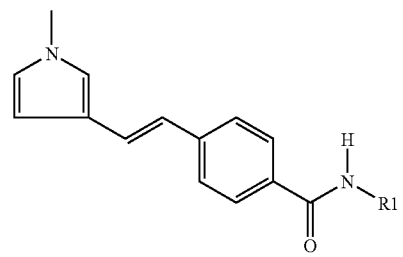

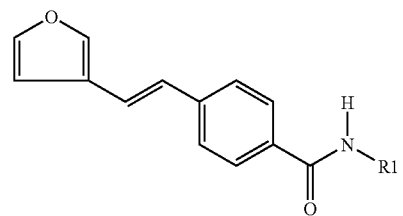

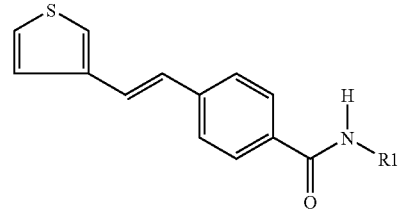

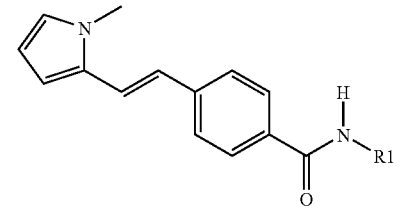

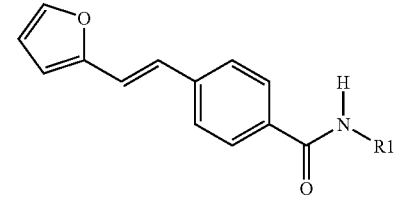

201
-continued
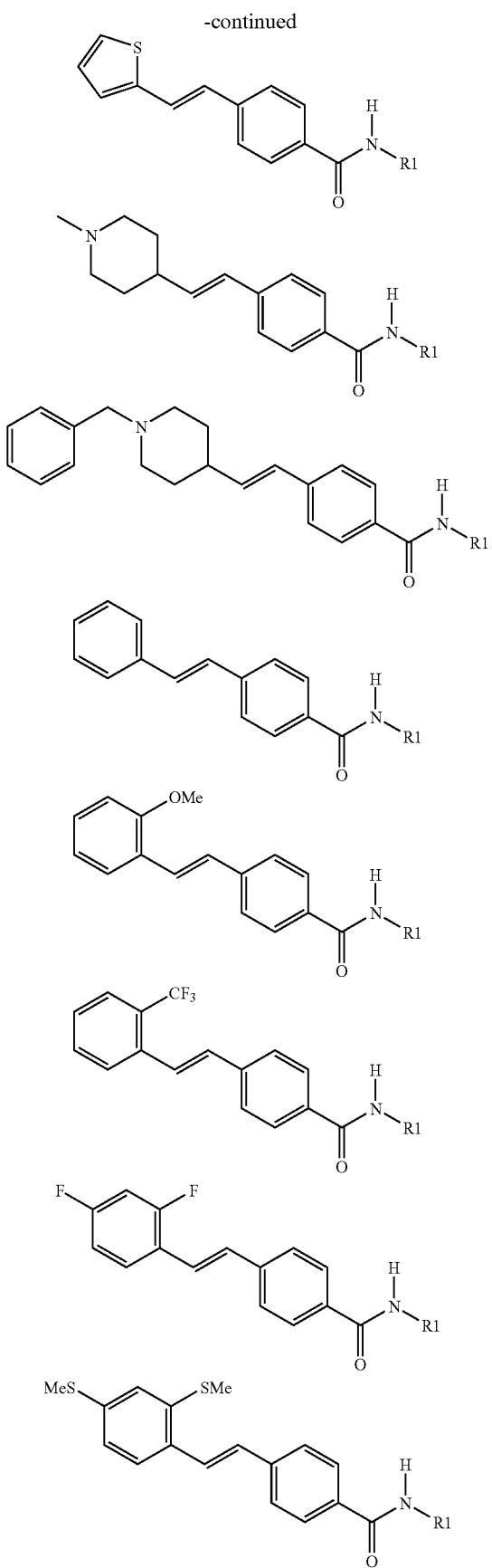
202
-continued
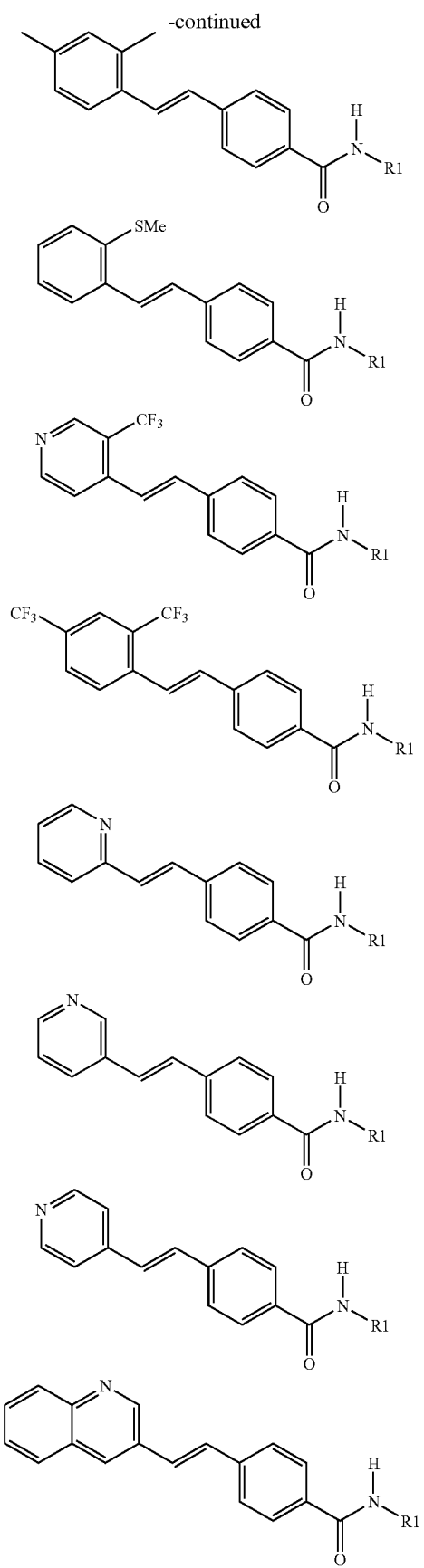

203
-continued
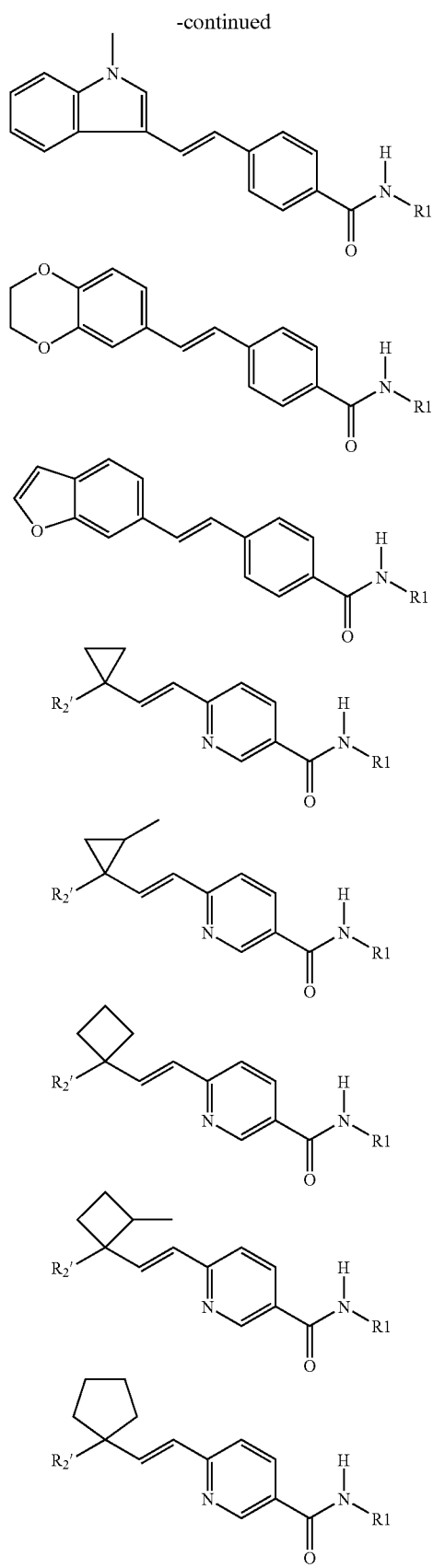
204
-continued
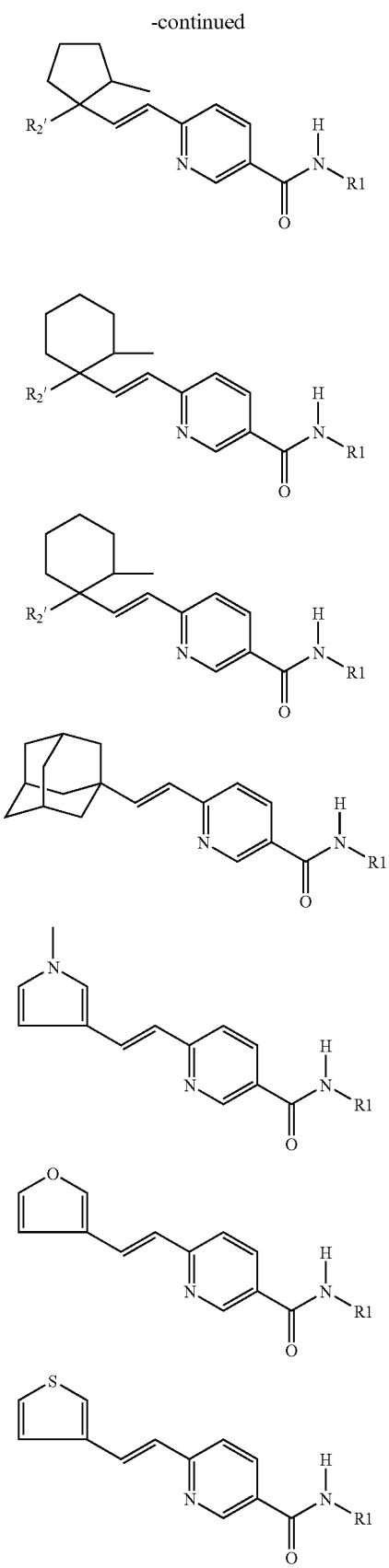

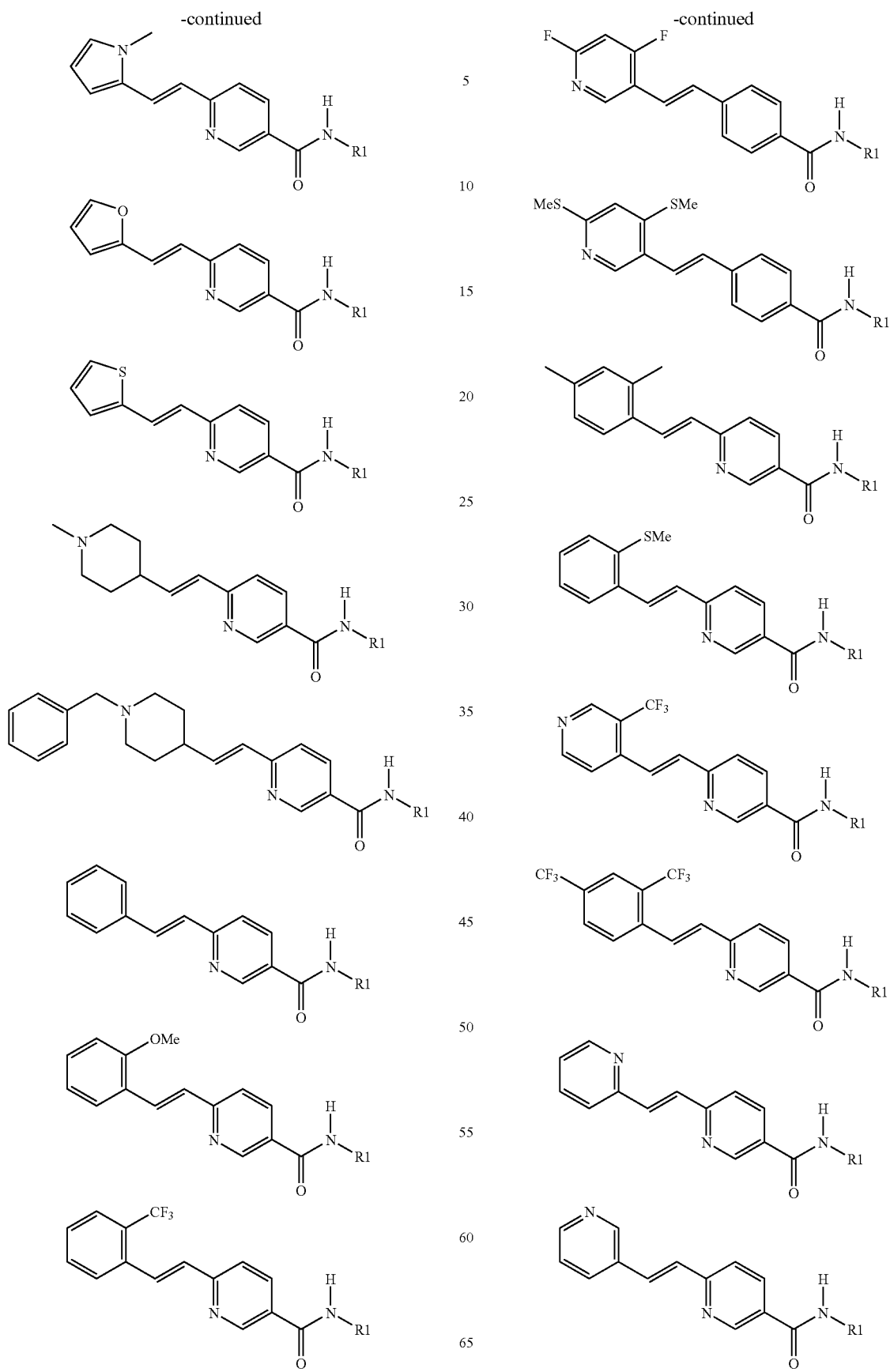

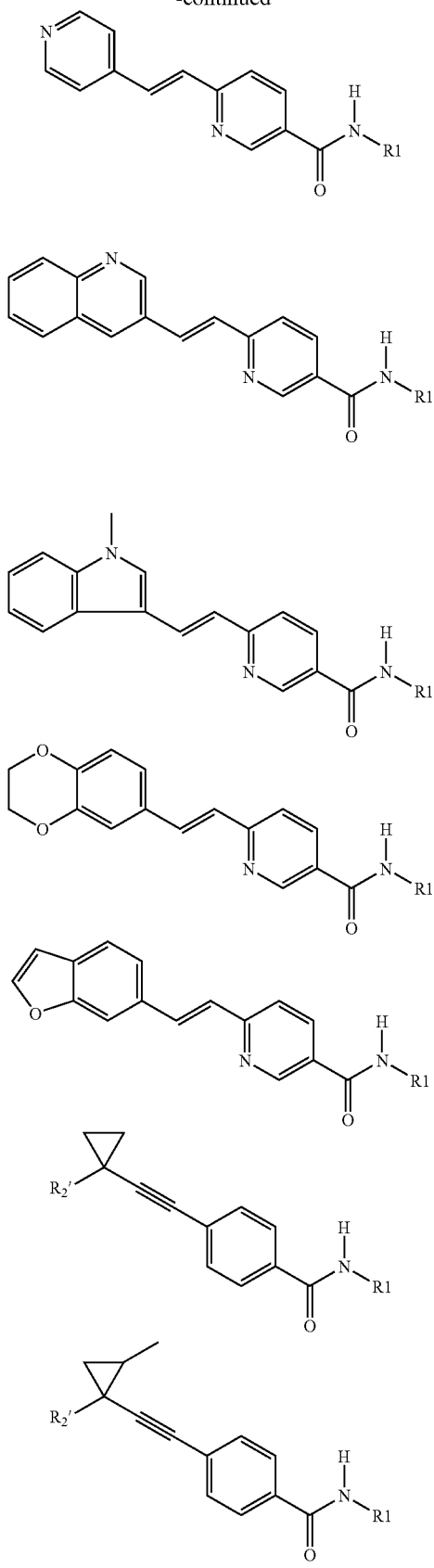
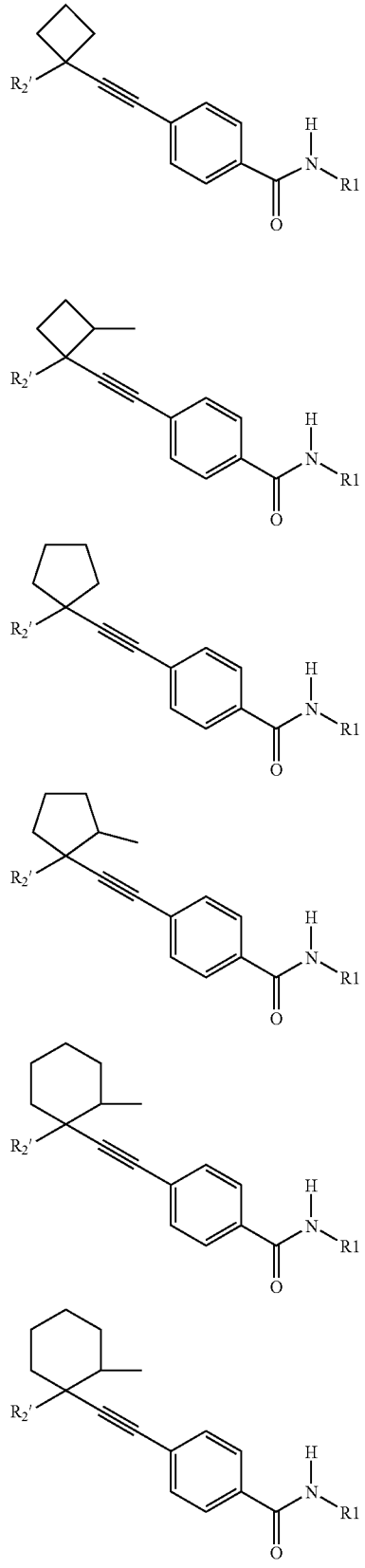

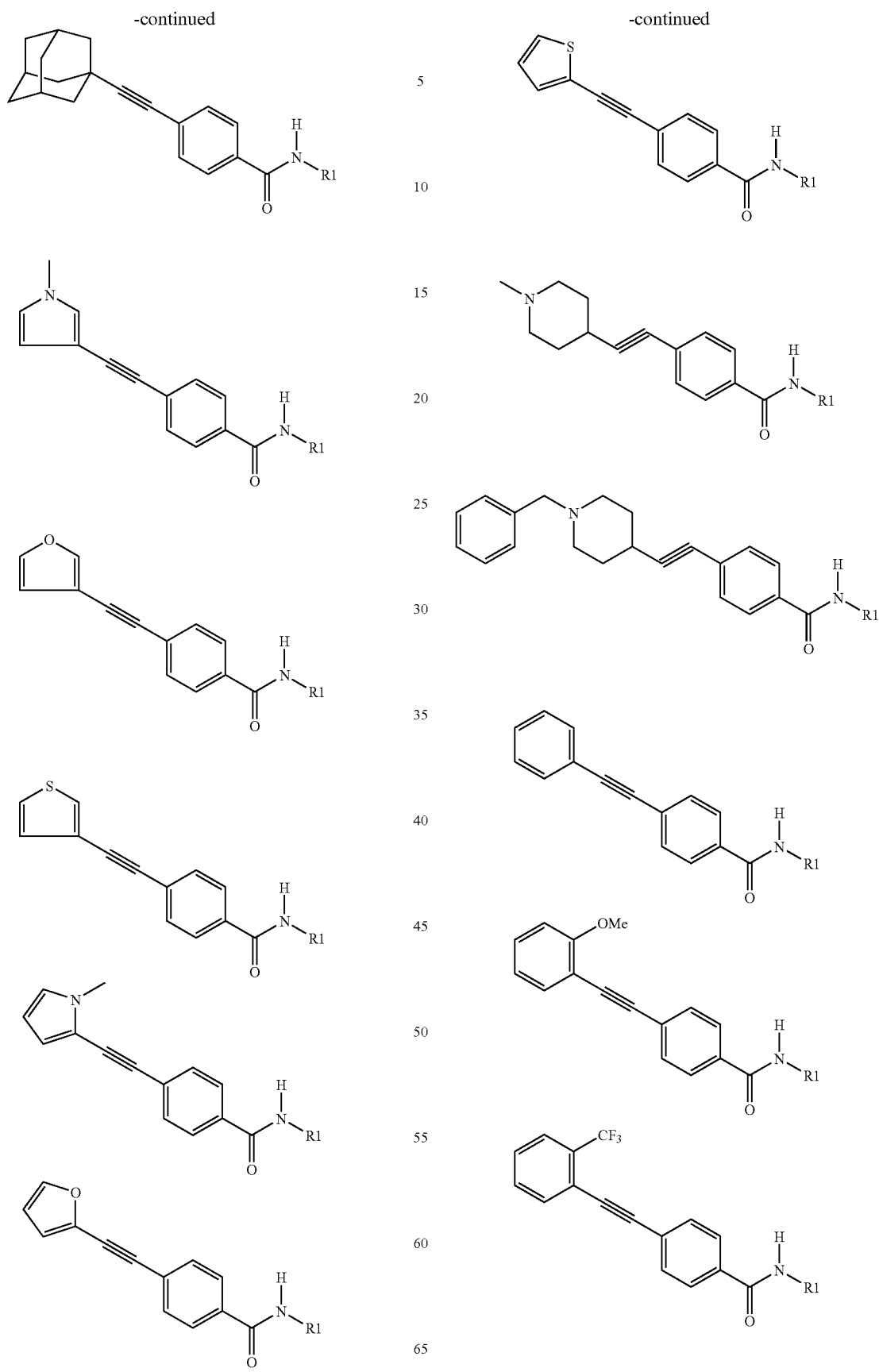

211
-continued
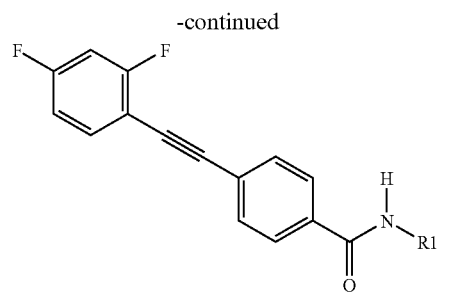
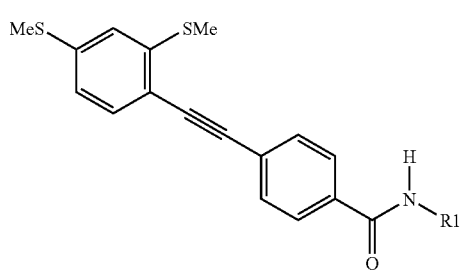
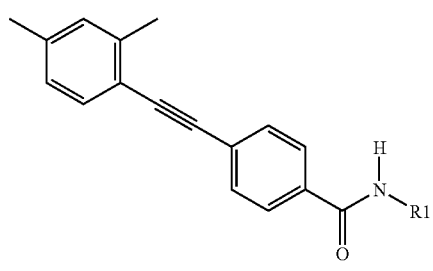
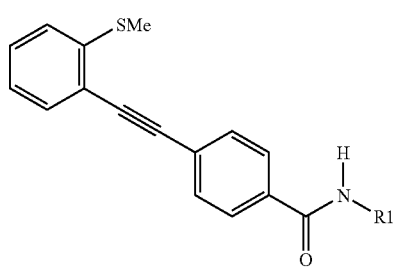
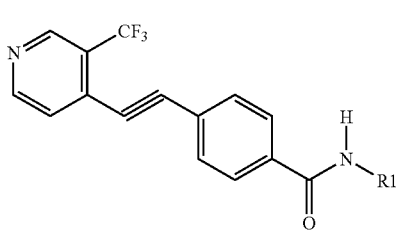
212
-continued
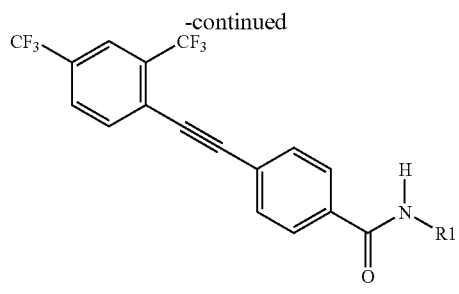
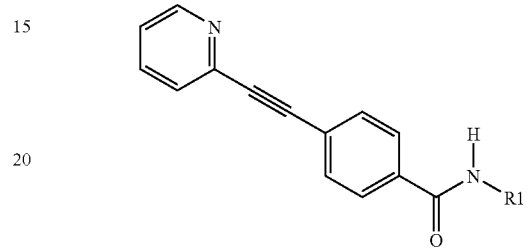
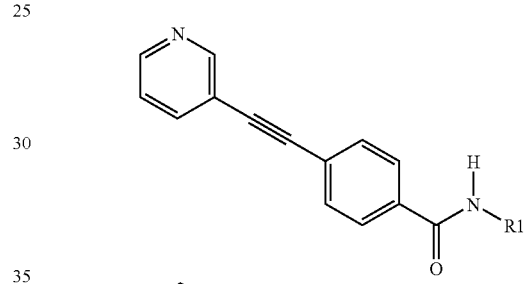
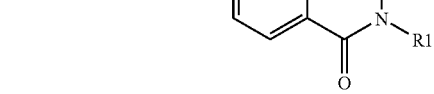
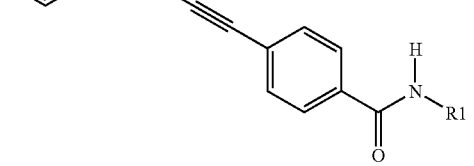

-continued
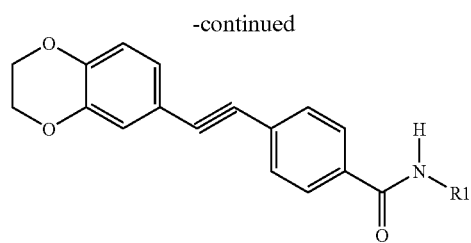
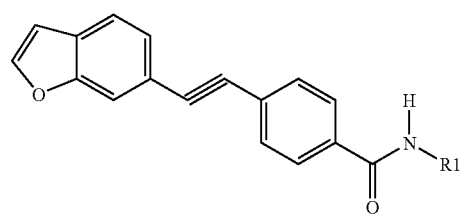
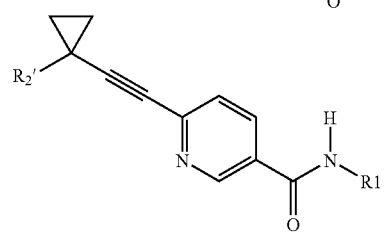
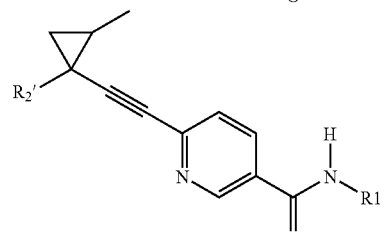
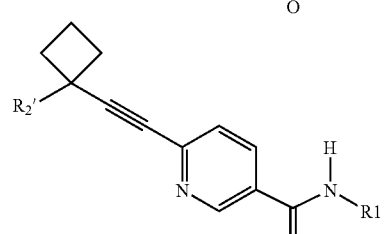
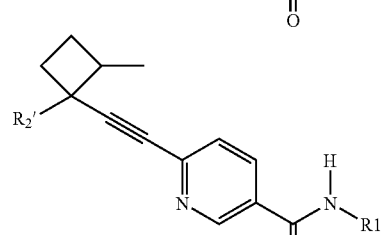
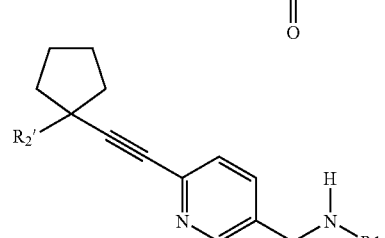
-continued
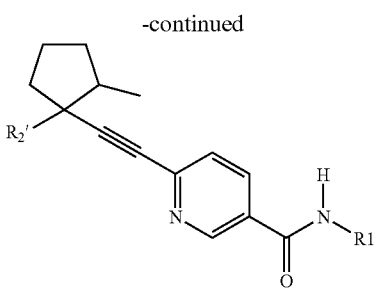
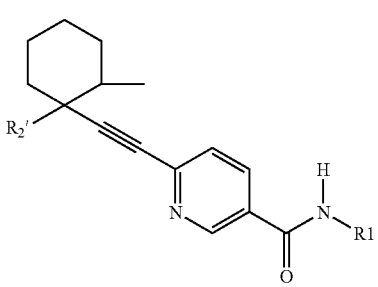
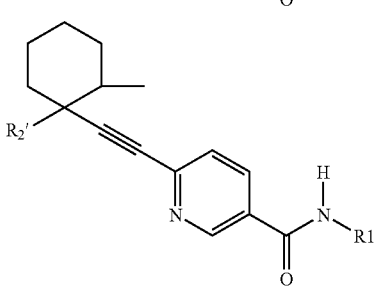
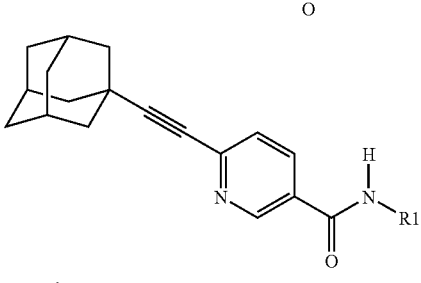
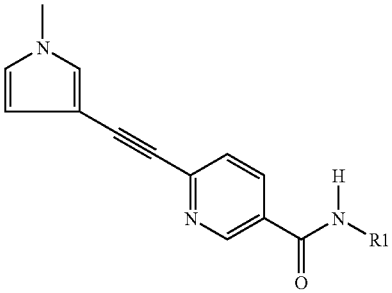
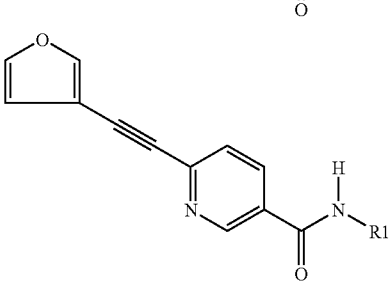

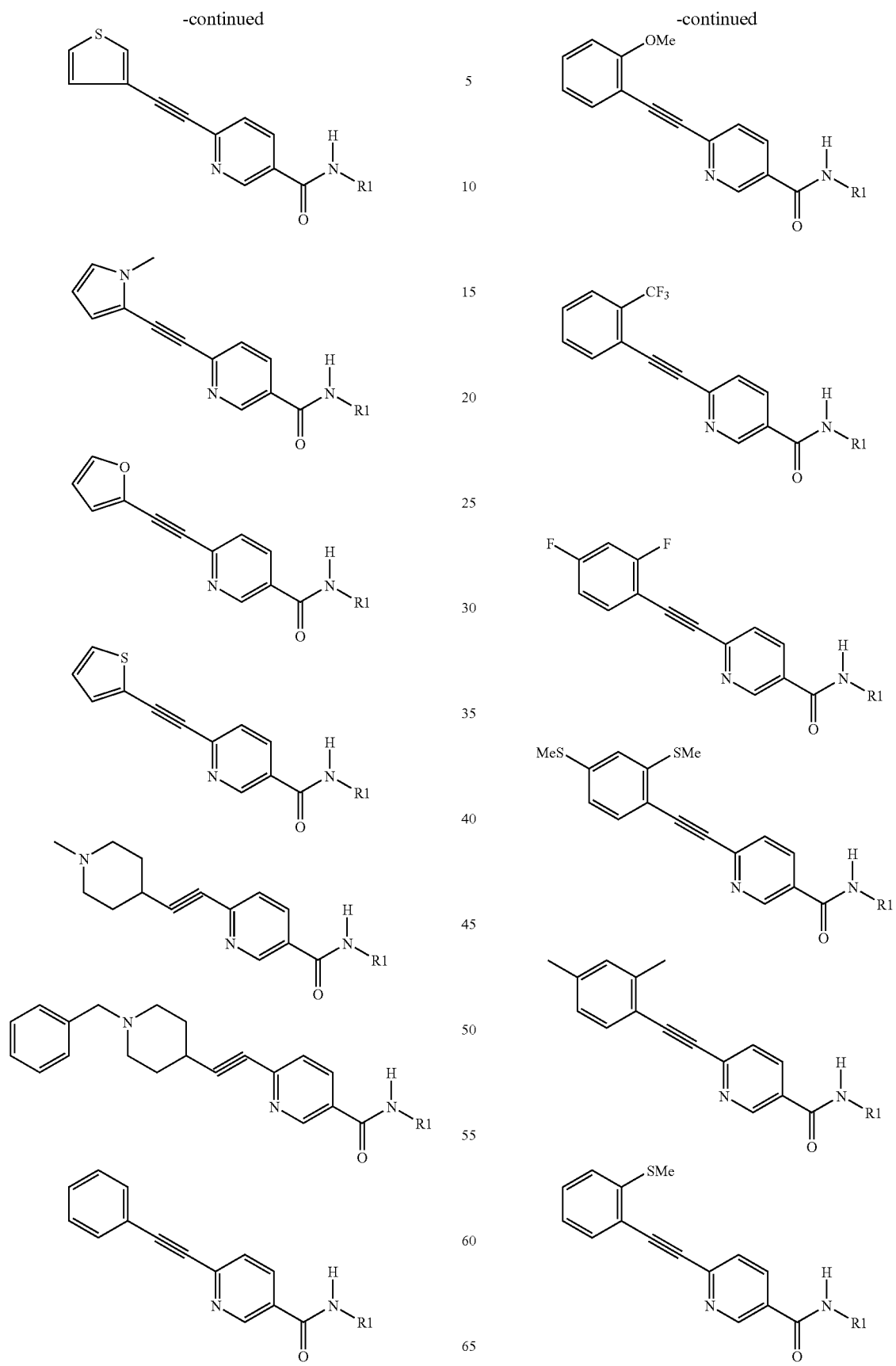

-continued

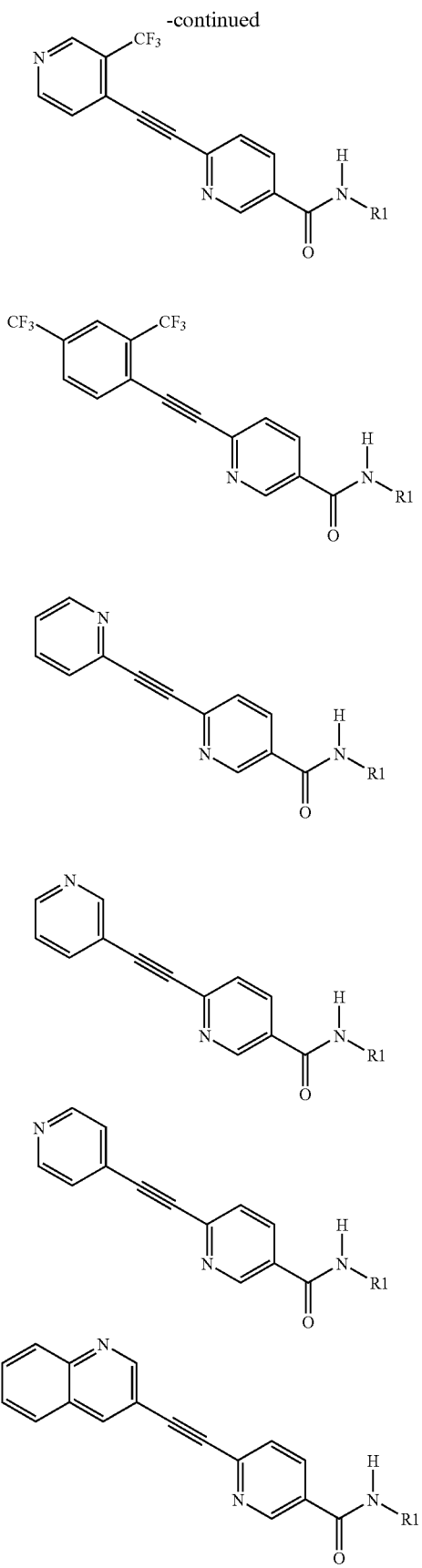

-continued

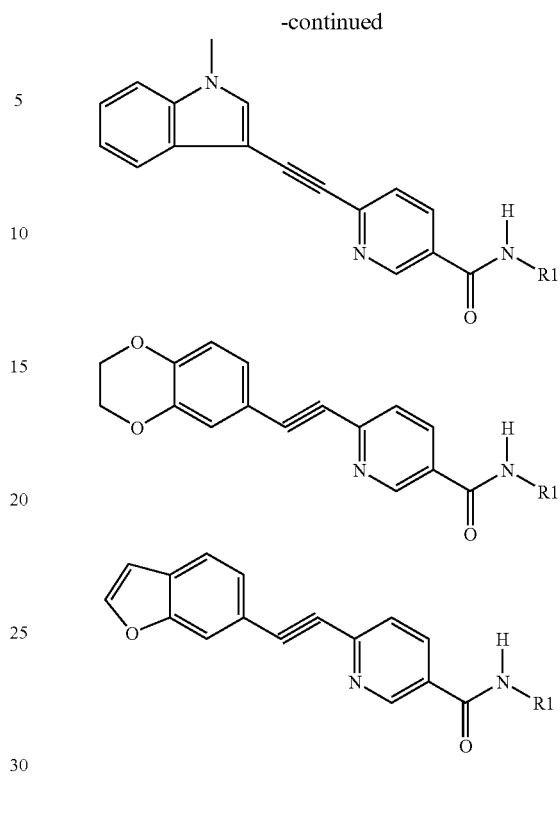

EXAMPLE 4

Calcium Imaging Assay

VR1 protein is a heat-gated cation channel that exchanges approximately ten calcium ions for every sodium ion resulting in neuronal membrane depolarization and elevated intracellular calcium levels. Therefore the functional activity of compounds at the VR1 receptor may be determined by measuring changes in intracellular calcium levels in neurons such as the dorsal root ganglion.

DRG neurons were grown on PDL coated 96-well black-walled plates, in the presence of DMEM medium containing 5% Penstrep, 5% Glutamax, 200 µg/ml hygromycin, µg/ml blasticide and 10% heat inactivated FBS. Prior to assay, cells were loaded with 5 µg/ml Fura2 in normal saline solution at 37° C. for 40 minutes. Cells were then washed with normal saline to remove dye before commencement of the experiment.

The plated neurons were transferred into a chamber on the stage of a Nikon eclipse TE300 microscope after which neurons were allowed to attain a stable fluorescence for about 10 minutes before beginning the experiment. The assay consists of two stages, a pretreatment phase followed by a treatment phase. First, a solution of the test compound was added from a multivalve perfusion system to the cells for 1 minute (pretreatment). Immediately following, capsaicin (250 nM) was added in the presence of the test compound (treatment) for a specific period between 20 and 60 seconds.

Fura2 was excited at 340 and 380 nM to indicate relative calcium ion concentration. Changes in wavelength measurements were made throughout the course of the experiment. The fluorescence ratio was calculated by dividing fluorescence measured at 340 nM by that at 380 nM. Data was collected using Intelligent Imaging's Slidebook software. All compounds that inhibited capsaicin induced calcium influx greater than 75% were considered positives.

Figure 3:
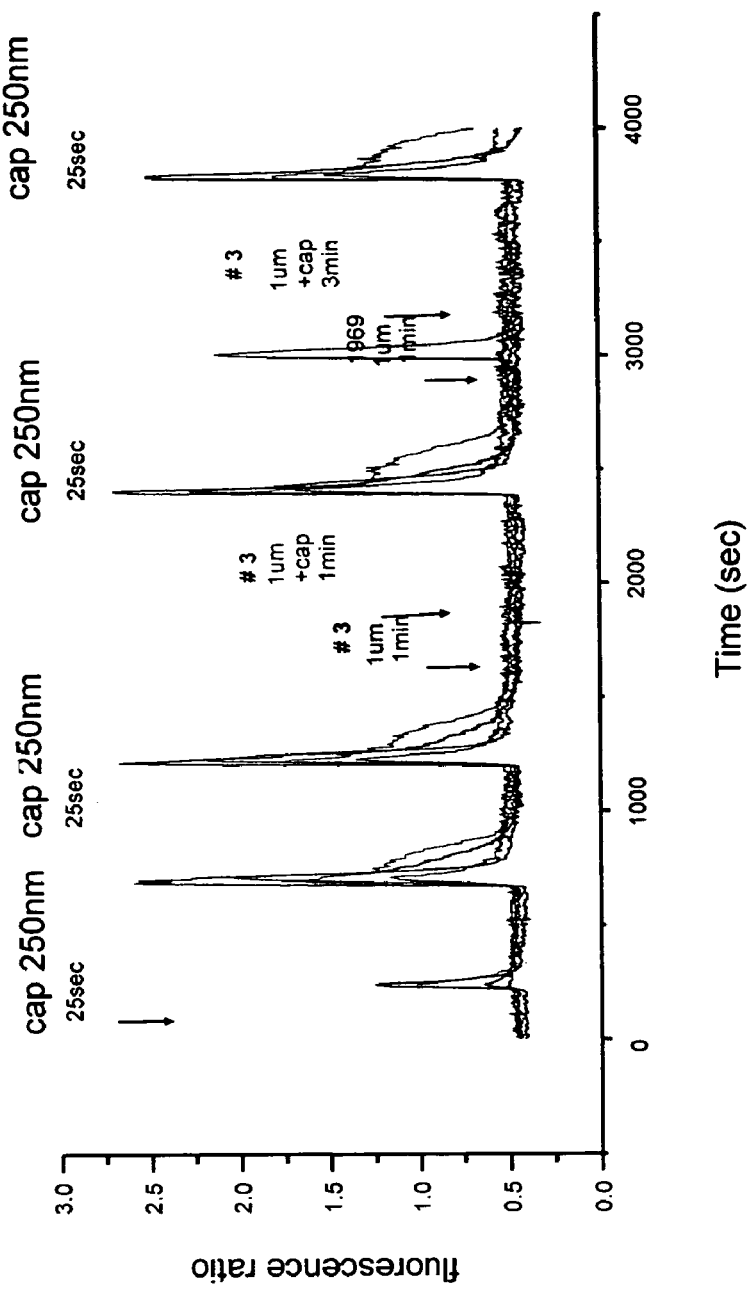
FIG. 3: A graph demonstrating the activity of compound 3 in inhibiting a capsaicin induced intracellular calcium current.
Figure 4:
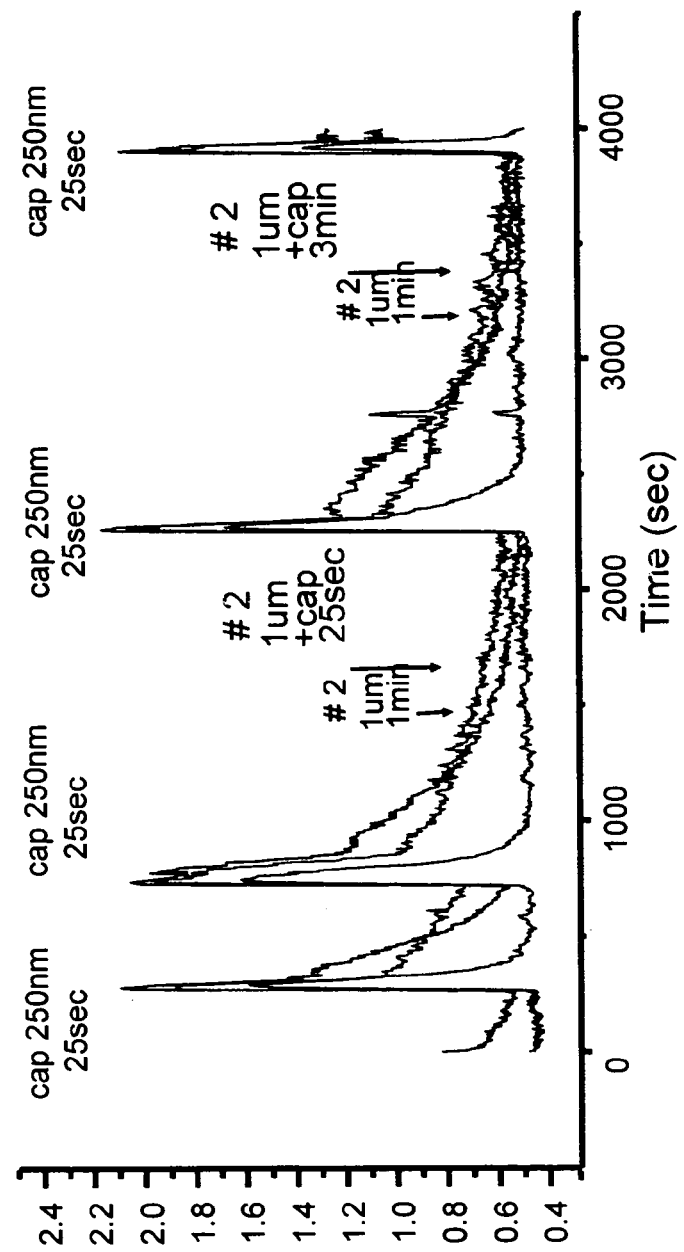
FIG. 4: A graph demonstrating the activity of compound 2 in inhibiting a capsaicin induced intracellular calcium current.

Table 2 provides the data obtained. FIG. 1 demonstrates results obtained when compound 155 is administered with capsaicin. Fluorescence reflecting calcium ion influx is reduced. FIG. 3 and FIG. 4 demonstrate the results of administering compounds 3 and 2 with capsaicin respectively.

TABLE 2

| Compound ID | Concentration | Treatment time (sec) | % inhibition of capsaicin induced calcium influx |
|---|---|---|---|
| 155 | 300 nM | 20 | <75 |
| 3 | 1 µM | 60 | 100 |
| 2 | 1 µM | 25 | 100 |

EXAMPLE 5

High Throughput Analysis of VR1 Antagonists for Determination of In Vitro Efficacy Using a Calcium Imaging Assay A dual wavelength ratiometric dye, Fura2, was used as an indicator of relative levels of calcium ions in a 96 well format using a bench top scanning fluorometer with integrated fluidics and temperature control (Flex Station, Molecular Devices).

neurons were grown on PDL coated 96-well black-walled plates, in the presence of a DMEM medium containing 5% Penstrep, 5% Glutamax, 200 µg/ml Hygromycin, 5 µg/ml Blasticide and 10% heat inactivated FBS. Prior to assay, the cells were loaded with 5 µg/ml Fura2 in normal saline solution at 37° C. for 40 minutes. Cells were then washed with normal saline to remove the dye.

The assay consists of two stages: a pre-treatment phase followed by a treatment phase. 50 µl of a compound solution was added to the cells (Pre-treatment). Immediately following, 50 µl of the test compound in a saline solution at pH 5.1 was added. Fura2 was excited at 340 and 380 nM to indicate relative calcium concentration. Changes in wavelength measurements were made throughout the course of the experiment in 4 second intervals over a period of 3 minutes. Responses were measured as peak fluorescence ratio after test compound addition minus baseline fluorescence ratio prior to pre-treatment with test compound and were calculated using SoftMaxPro software. Data were expressed as percentage inhibition calculated using Excel as follows:

$$\text{Percentage inhibition} = \frac{(\text{Compound Response} - \text{Control Response})}{(\text{Agonist Response} - \text{Control Response})} \times 100$$

All compounds with percentage inhibition values greater than 75% were considered positives. The relative strength of each compound in inhibiting calcium ion influx is set forth in Table 2.

EXAMPLE 6

Whole-Cell Patch Clamp Electrophysiology

Dorsal root ganglion (DRG) neurons were recovered from either neonatal or adult rats and plated onto poly-D-lysine coated glass coverslips. The plated neurons were transferred into a chamber to allow drug solutions to be added to the cells using a computer-controlled solenoid-valve based perfusion system. The cells were imaged using standard DIC optics. Cells were patched using finely-pulled glass electrodes. Voltage-clamp electrophysiology experiments were carried out using an Axon Instruments Multiclamp amplified controlled by pCLAMP8 software.

The cells were placed into a whole-cell voltage clamp and held at a voltage of −80 mV while monitoring the membrane current in gap-free recording mode. 500 nM capsaicin was added for 30 seconds as a control. Test compounds at various concentrations were added to the cells for 1 minute prior to a 30 second capsaicin application. Differences between control experiments and drug positive capsaicin experiments were used to determine the efficacy of each test compound. All compounds that inhibited capsaicin induced current greater than 50% were considered positives. The data obtained for compound 155 is set forth in Table 3.

TABLE 3

| Compound ID | Concentration | Treatment time (seconds) | % inhibition of capsaicin induced current |
|---|---|---|---|
| 155 | 100 nM | 20 | 50 |

Figure 2:
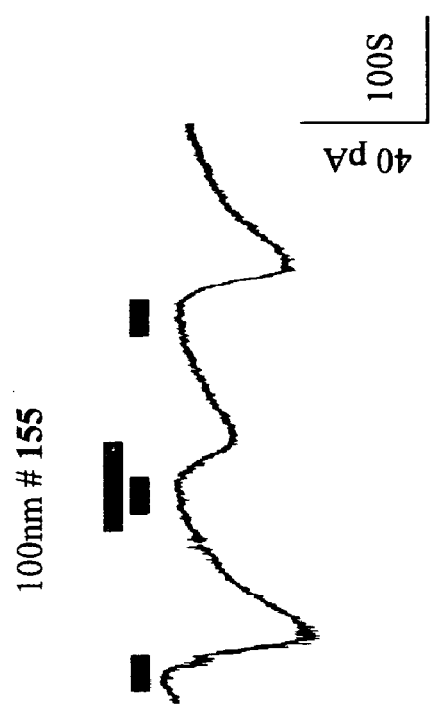
FIG. 2: A graph demonstrating the activity of compound 155 in inhibiting a capsaicin induced intracellular calcium current. Capsaicin administered in the presence of compound 155 produces less calcium influx in neurons than capsaicin administered to the same neurons alone.

FIG. 2 demonstrates the activity of compound 155 in inhibiting the capsaicin-induced calcium current.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:

1. A compound having a formula:

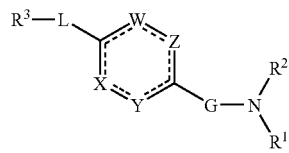

or a pharmaceutically acceptable salt, or a stereoisomer thereof, wherein:

each of W, X, Y and Z is independently selected from N and $CR^4$;

L is $-(CR^5{=}CR^6)-$;

G is $C{=}O$;

$R^1$ is substituted or unsubstituted cycloheteroalkyl, or heteroaryl;

R² is hydrogen;

R³ is CF₃, n-propyl, or a group of formula:

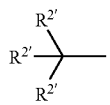

wherein each of R²' is hydrogen or alkyl provided at least two of R²' are alkyl; and wherein two R²' that are alkyl may join together to form a cycloalkyl ring of 3-8 atoms;

each R⁴ is independently hydrogen, alkyl, substituted or unsubstituted alkyl, acyl, acylamino, alkylamino, alkylthio, alkoxy, alkoxycarbonyl, alkylarylamino, arylalkyloxy, amino, aryl, arylalkyl, sulfinyl, sulfonyl, sulfanyl, aminosulfonyl, arylsulfonyl, sulfo, dihydroxyphosphoryl, aminohydroxyphosphoryl, azido, carboxy, carbamoyl, carboxyl, cyano, cycloheteroalkyl, dialkylamino, halo, heteroaryloxy, heteroaryl, heteroalkyl, hydroxyl, nitro or thiol; and each of R⁵ and R⁶ is independently H, halo, or $C_{1-6}$alkyl.

2. A compound having a formula:

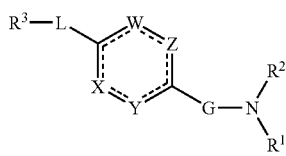

or a pharmaceutically acceptable salt, or a stereoisomer thereof, each of W, X, Y and Z is independently selected from N and CR⁴;

L is —(C≡C)—;

G is C=O;

R¹ is substituted or unsubstituted cycloheteroalkyl, or heteroaryl;

R² is hydrogen;

R³ is CF₃, n-propyl, or a group of formula:

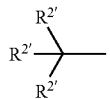

wherein each of R²' is hydrogen or alkyl provided at least two of R²' are alkyl; and wherein two R²' that are alkyl may join together to form a cycloalkyl or cycloheteroalkyl ring of 3-8 atoms; and each R⁴ is independently hydrogen, alkyl, substituted or unsubstituted alkyl, acyl, alkylthio, alkoxy, alkoxycarbonyl, arylalkyloxy, aryl, arylalkyl, sulfinyl, sulfonyl, sulfanyl, aminosulfonyl, arylsulfonyl, sulfo, dihydroxyphosphoryl, aminohydroxyphosphoryl, azido, carboxy, carbamoyl, carboxyl, cyano, cycloheteroalkyl, dialkylamino, halo, heteroaryloxy, heteroaryl, heteroalkyl, hydroxyl, nitro or thiol.

3. The compound of claim 1 or 2 wherein each of W, Z, X and Y represents CH.

4. The compound of claim 1 or 2 wherein R¹ is substituted or unsubstituted pyrrolidinyl, piperidinyl, or morpholinyl.

5. The compound of claim 1 or 2 wherein R¹ is substituted or unsubstituted pyridinyl or pyrimidinyl.

6. The compound of claim 1 or 2 wherein R¹ is substituted or unsubstituted furanyl, imidazolyl, thiophenyl, pyrazolyl, or thiazolyl.

7. The compound of claim 1 or 2 wherein R¹ is substituted or unsubstituted benzodioxanyl, benzopyranyl, indolyl, indazolyl, methylenedioxyphenyl, quinolinyl, isoquinolinyl, tetrahydroquinolinyl, tetrahydroisoquinolinyl, dihydroquinolinyl, or dihydroisoquinolinyl.

8. The compound of claim 1 or 2 wherein R¹ is substituted or unsubstituted quinolinyl or isoquinolinyl.

9. The compound of claim 1 or 2 wherein each of W, X, Y and Z is CR⁴.

10. The compound of claim 1 or 2 wherein W is N and each of X, Y and Z is CR⁴.

11. The compound of claim 1 or 2 wherein Y is N and each of W, X and Z is CR⁴.

12. The compound of claim 1 or 2 wherein any two of W, X, Y and Z are Ns.

13. The compound of claim 1 wherein one of R⁵ and R⁶ is methyl and the other is hydrogen.

14. The compound of claim 1 wherein each of R⁵ and R⁶ is hydrogen.

15. The compound of claim 1 or 2 wherein R³ is t-Bu, i-Pr, cyclopropyl or cyclobutyl.

16. The compound of claim 1 or 2 wherein R³ is CF₃.

17. A compound having a formula:

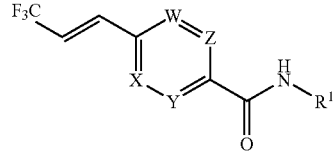

or a pharmaceutically acceptable salt, or a stereoisomer thereof;

wherein:

each of W, X, Y and Z is independently selected from CR⁴;

R¹ is substituted or unsubstituted cycloheteroalkyl or heteroaryl;

each R⁴ is independently hydrogen, alkyl, substituted or unsubstituted alkyl, acyl, alkylthio, alkoxy, alkoxycarbonyl, arylalkyloxy, aryl, arylalkyl, sulfinyl, sulfonyl, sulfanyl, aminosulfonyl, arylsulfonyl, sulfo, dihydroxyphosphoryl, aminohydroxyphosphoryl, azido, carboxy, carbamoyl, carboxyl, cyano, cycloheteroalkyl, dialkylamino, halo, heteroaryloxy, heteroaryl, heteroalkyl, hydroxyl, nitro or thiol.

18. The compound of claim 17 wherein each of W, X, Y and Z is CH.

19. The compound of claim 17 or 18 wherein R¹ is selected from substituted or unsubstituted pyrrolyl, pyridinyl, pyrimidinyl, furanyl, imidazolyl, thiophenyl, pyrazolyl, or thiazolyl.

20. The compound of claim 17 or 18 wherein R¹ is selected from substituted or unsubstituted benzodioxanyl, benzopyranyl, indolyl, indazolyl, methylenedioxyphenyl, quinolinyl, isoquinolinyl, tetrahydroquinolinyl, tetrahydroisoquinolinyl, dihydroquinolinyl, or dihydroisoquinolinyl.

21. The compound of claim 1 selected from the group consisting of:

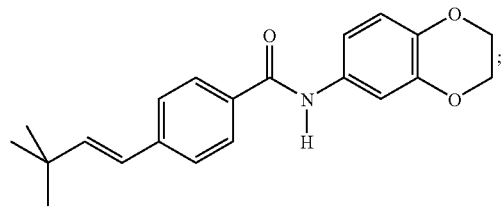
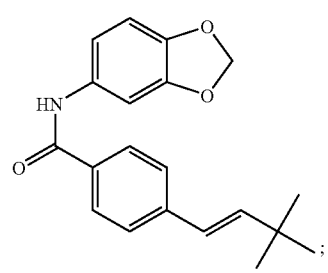
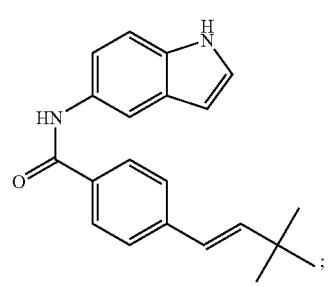
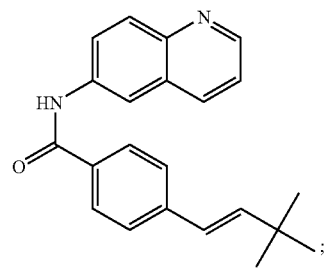
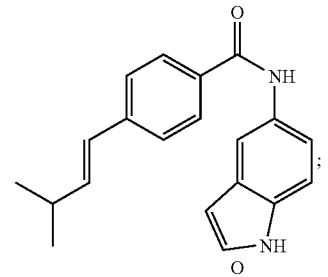
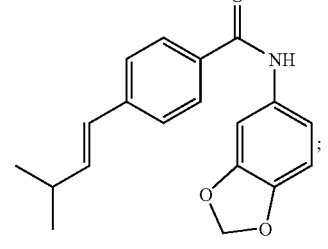
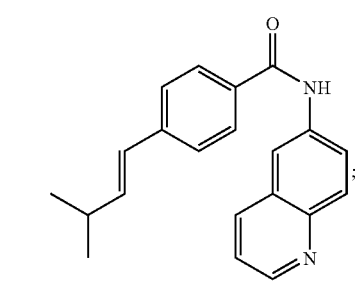
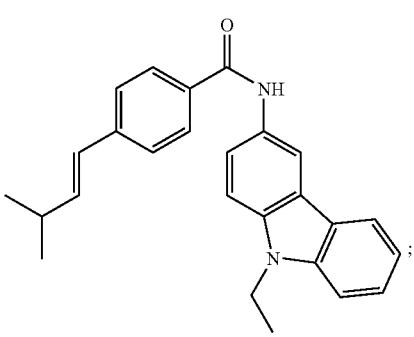
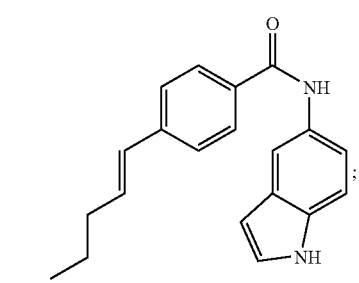
and pharmaceutically acceptable salts and stereoisomers thereof.
22. The compound of claim 1 selected from the group consisting of:
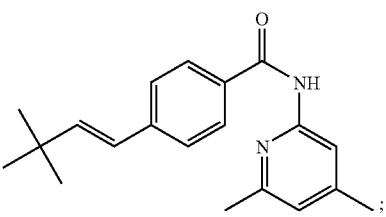
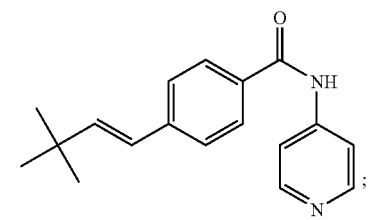

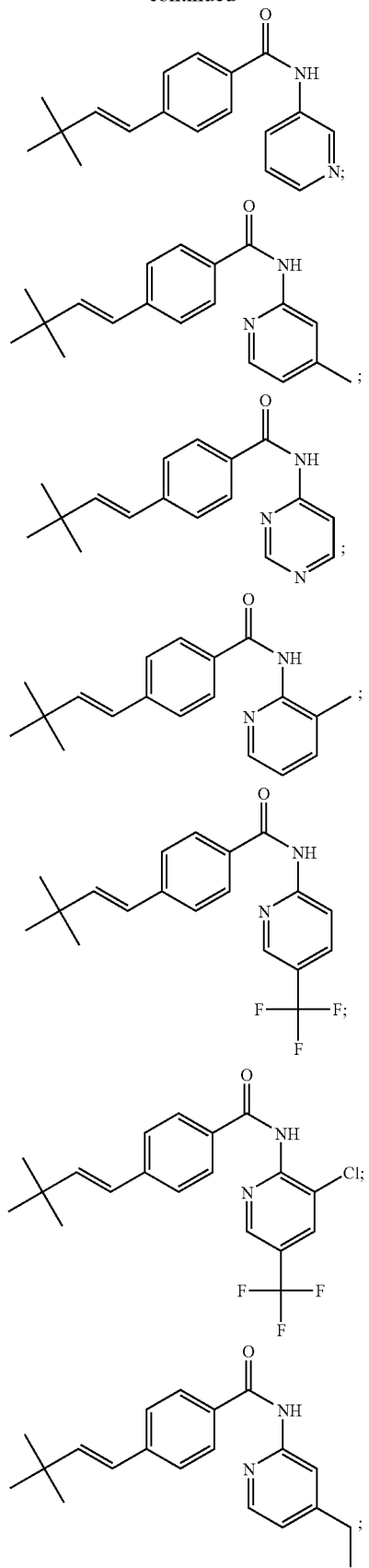
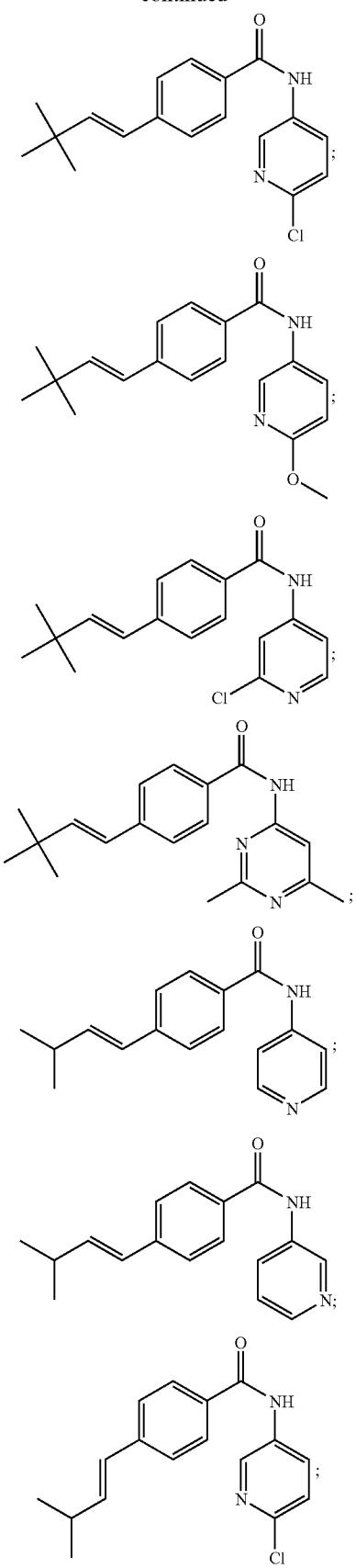

-continued
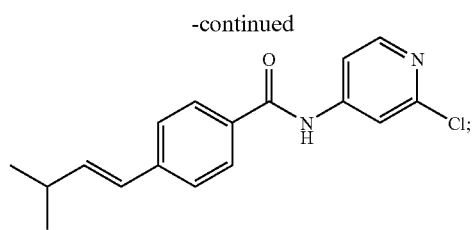
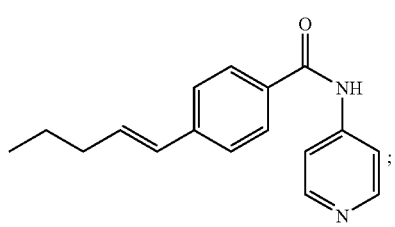
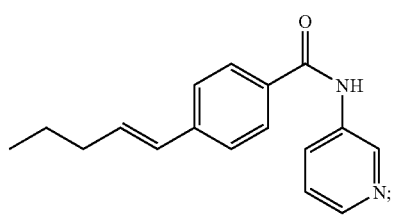
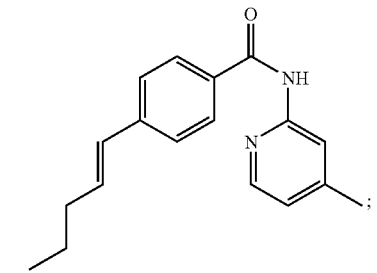
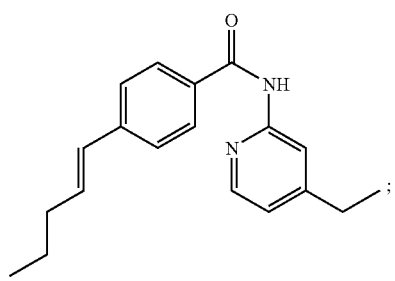
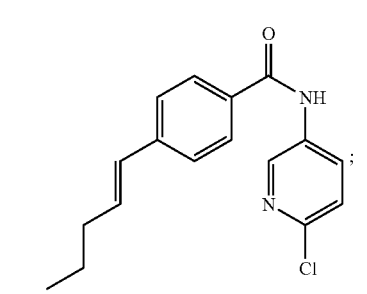
-continued
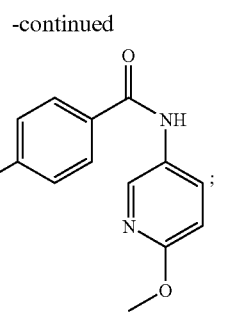
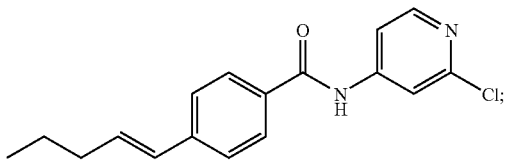
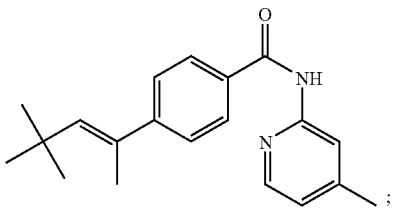
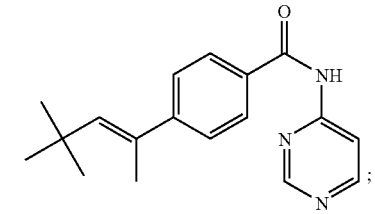
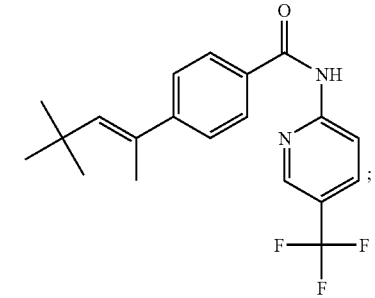
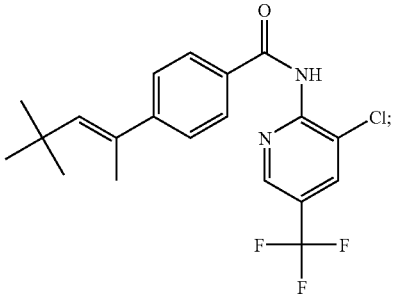

-continued

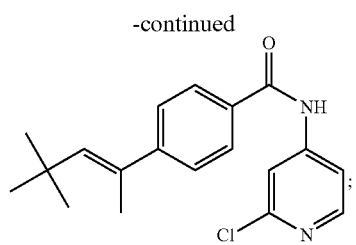

and pharmaceutically acceptable salts and stereoisomers thereof.

23. The compound of claim 1 selected from the group consisting of:

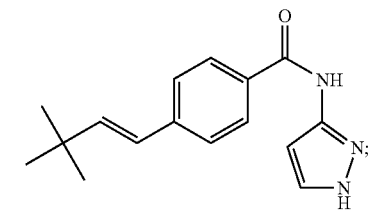

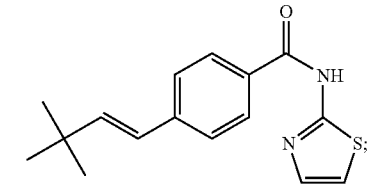

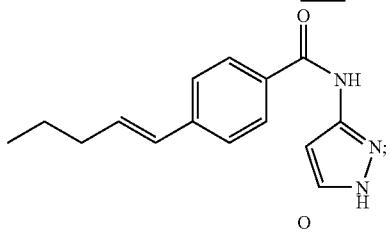

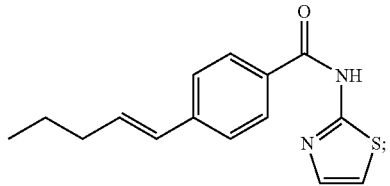

and pharmaceutically acceptable salts and stereoisomers thereof.

24. The compound of claim 1 selected from the group consisting of:

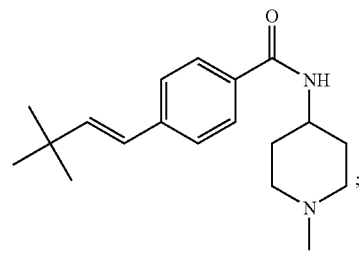

-continued

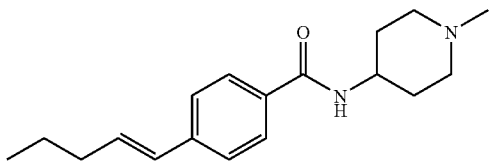

and pharmaceutically acceptable salts and stereoisomers thereof.

25. The compound of claim 2 selected from the group consisting of:

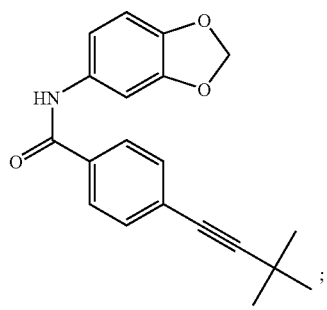

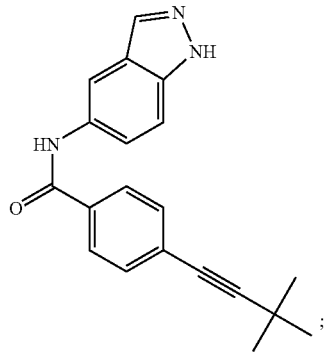

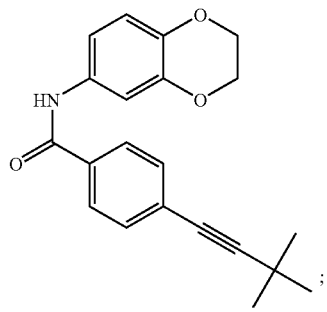

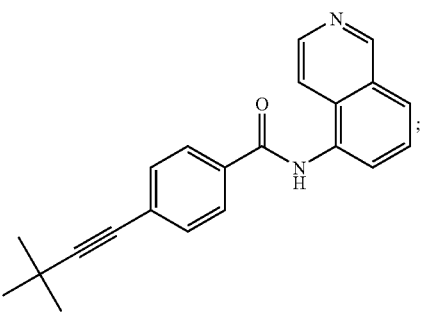

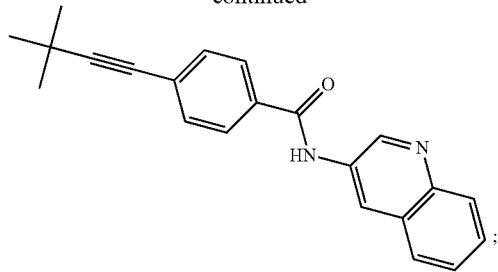
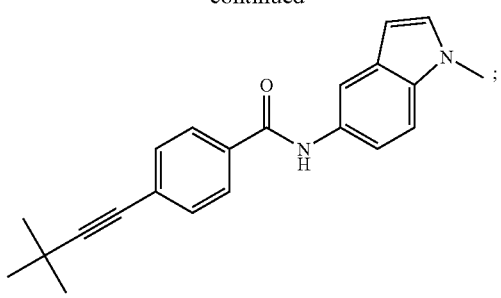
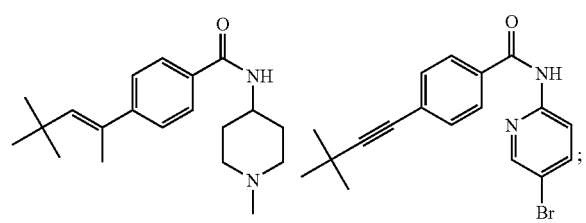
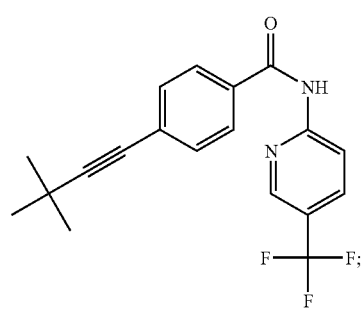
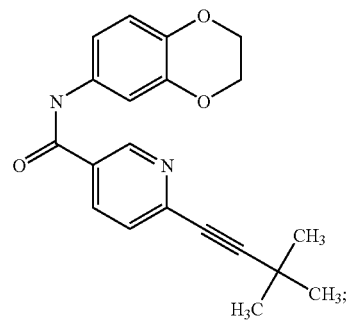
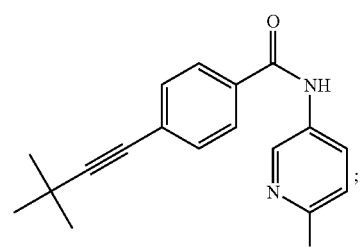
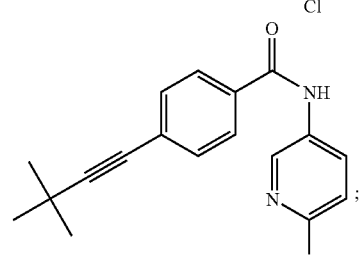
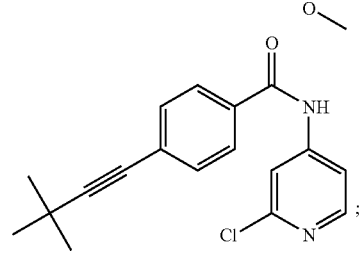
and pharmaceutically acceptable salts and stereoisomers thereof.
26. The compound of claim 2 selected from the group consisting of:
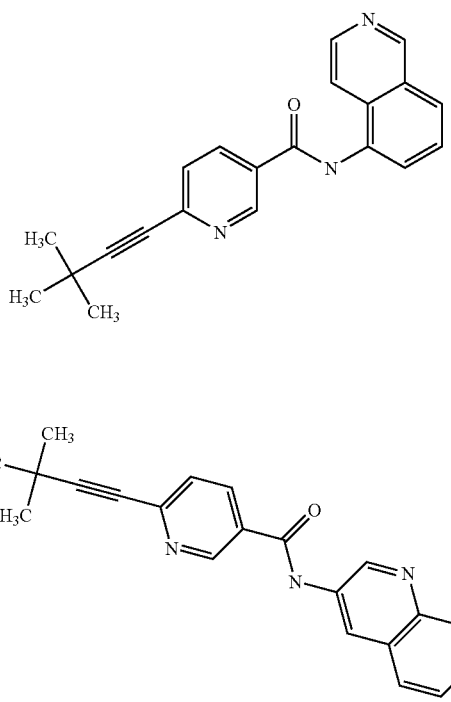

-continued
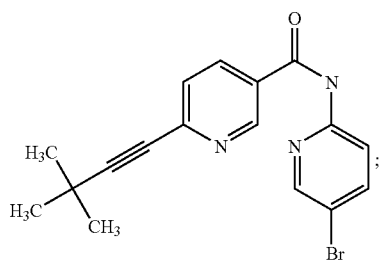
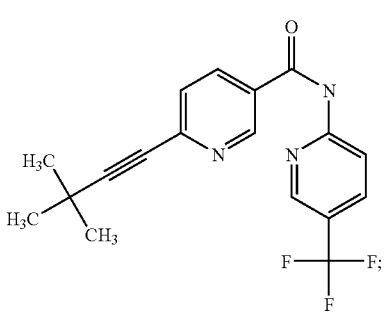
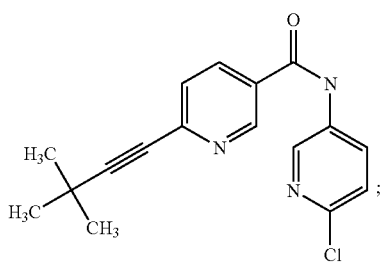
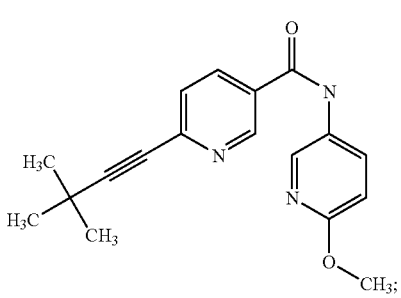
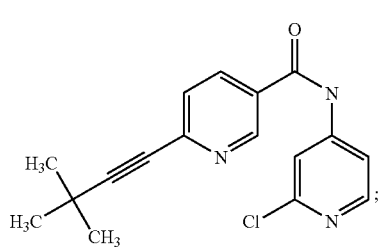
-continued
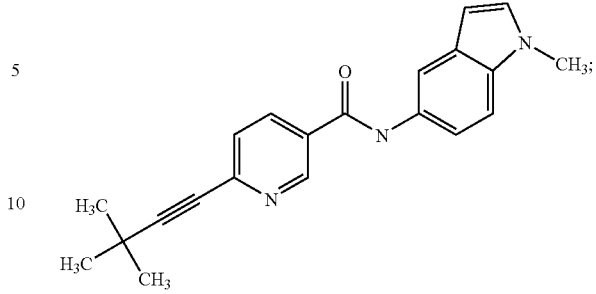
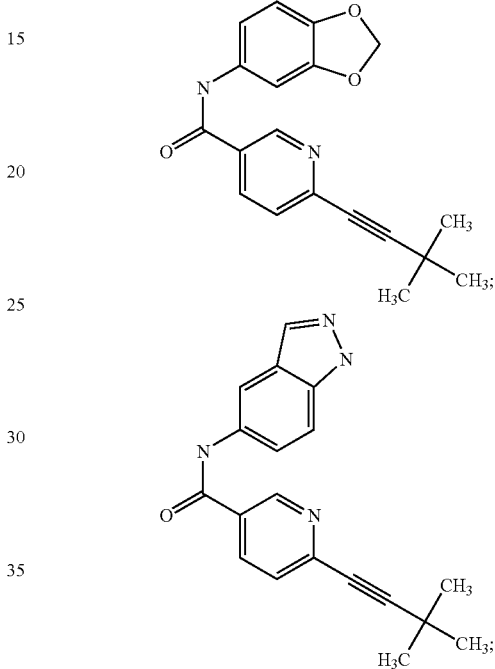
and pharmaceutically acceptable salts and stereoisomers thereof.
27. The compound of claim 1 selected from the group consisting of:
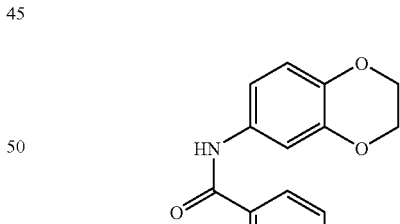
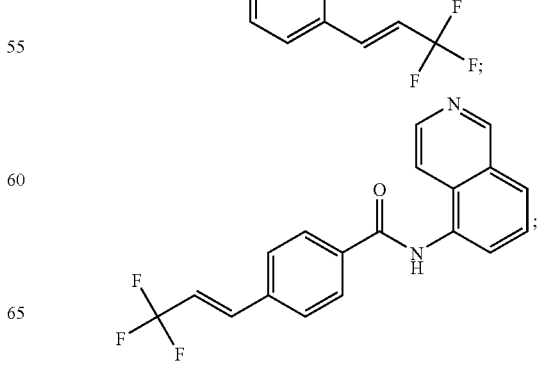

-continued

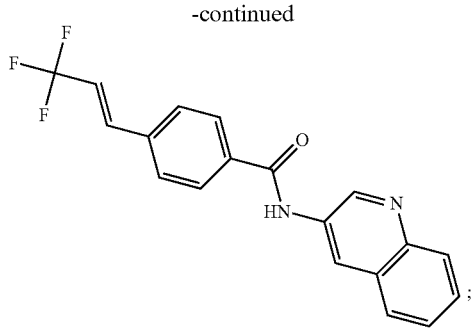

and pharmaceutically acceptable salts and stereoisomers thereof.

28. A pharmaceutical composition comprising a pharmaceutically acceptable carrier and a pharmaceutically effective amount of the compound of claim 1.

29. A pharmaceutical composition comprising a pharmaceutically acceptable carrier and a pharmaceutically effective amount of the compound of claim 2.

30. The pharmaceutical composition of claim 28 or 29 wherein the carrier is a parenteral carrier.

31. The pharmaceutical composition of claim 28 or 29 wherein the carrier is an oral carrier.

32. The pharmaceutical composition of claim 28 or 29 wherein the carrier is a topical carrier.

33. A method for treating a disease or condition, which comprises administering to a patient in need of such treatment a therapeutically effective amount of the compound of claim 1, wherein the disease or condition is: pain, acute pain, inflammatory pain, neuropathic pain, chronic pain, dental pain, headache, migraine, cluster headache, or tension headache.

34. A method for treating a disease or condition, which comprises administering to a patient in need of such treatment a therapeutically effective amount of the compound of claim 2, wherein the disease or condition is: pain, acute pain, inflammatory pain, neuropathic pain, chronic pain, dental pain, headache, migraine, cluster headache, or tension headache.

35. A method for treating a disease or condition, which comprises administering to a patient in need of such treatment a therapeutically effective amount of the pharmaceutical composition of claim 28, wherein the disease or condition is: pain, acute pain, inflammatory pain, neuropathic pain, chronic pain, dental pain, headache, migraine, cluster headache, or tension headache.

36. A method for treating a disease or condition, which comprises administering to a patient in need of such treatment a therapeutically effective amount of the pharmaceutical composition of claim 29, wherein the disease or condition is: pain, acute pain, inflammatory pain, neuropathic pain, chronic pain, dental pain, headache, migraine, cluster headache, or tension headache.

37. A method for preparing the compound of claim 1 or 2 which comprises contacting a compound of the formula

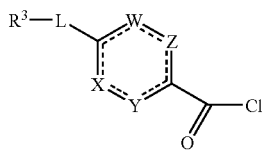

with a compound of the formula $R^1R^2NH$ under conditions sufficient to form said compound of claim 1 or 2.

* * * * *

UNITED STATES PATENT AND TRADEMARK OFFICE
CERTIFICATE OF CORRECTION

| | | |
|---|---|---|
| PATENT NO. | : 7,432,281 B2 | Page 1 of 1 |
| APPLICATION NO. | : 10/961483 | |
| DATED | : October 7, 2008 | |
| INVENTOR(S) | : Kelly et al. | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 449 days Delete the phrase "by 449 days" and insert -- by 886 days --

Signed and Sealed this

Fourth Day of May, 2010

David J. Kappos
*Director of the United States Patent and Trademark Office*